(12) United States Patent
Hinuma et al.

US007074761B1

(10) Patent No.: US 7,074,761 B1
(45) Date of Patent: Jul. 11, 2006

(54) PEPTIDES AND PRODUCTION AND USE THEREOF

(75) Inventors: Shuji Hinuma, Tsukuba (JP); Shoji Fukusumi, Tsukuba (JP); Chieko Kitada, Sakai (JP)

(73) Assignee: Takeda Chemical Ind., Ltd., Osaka (JP)

( * ) Notice: Subject to any disclaimer, the term of this patent is extended or adjusted under 35 U.S.C. 154(b) by 0 days.

(21) Appl. No.: 09/207,168

(22) Filed: Dec. 7, 1998

Related U.S. Application Data

(63) Continuation-in-part of application No. PCT/JP97/01911, filed on Jun. 5, 1997.

(30) Foreign Application Priority Data

| Jun. 7, 1996 | (JP) | ................................... 8/146052 |
| Sep. 19, 1996 | (JP) | ................................... 8/247710 |
| Oct. 15, 1996 | (JP) | ................................... 8/272422 |

(51) Int. Cl.
*A61K 38/10* (2006.01)
*A61K 38/31* (2006.01)
*C07K 14/655* (2006.01)
*C07K 4/12* (2006.01)
*C07K 14/46* (2006.01)

(52) U.S. Cl. ............................. 514/12; 514/12; 514/13; 514/806; 530/311; 530/324; 530/326; 530/327; 530/350; 930/160

(58) Field of Classification Search ................... 514/13, 514/14, 12; 530/311, 350
See application file for complete search history.

(56) References Cited

U.S. PATENT DOCUMENTS 6,074,872 A * 6/2000 Sutcliffe et al. .......... 435/320.1
6,232,100 B1 * 5/2001 Olsen et al. ................ 435/69.4

FOREIGN PATENT DOCUMENTS

WO    WO 97/43417    11/1997

OTHER PUBLICATIONS

Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Sherman F; Stewart J W; Tsunasawa S. Methionine or not methionine at the beginning of a protein. Bioessays, (Jul. 1985) 3 (1) 27-31.*
P.C. Andrews, et al., *Isolation and Characterization of a Variant Somatostatin-14 and Two Related Somatostatins of 34 and 37 Residues from Lamprey (Petromyzon marinus)*, The Journal of Biological Chemistry, vol. 263, No. 30, 1998, pp. 15809-15814.
J. Michael Conlon, et al., *Somatostatin-Related and Glucagon-Related Peptides with Unusual Structural Features from the European Eel (Anguilla anguilla)*, General and Comparative Endocrinology 72, 1998, pp. 181-189.
Luis de Lecea, et al., *A Cortical Neuropeptide with Neuronal Depressant and Sleep-Modulating Properties*, Letters to Nature, 1996, vol. 381, pp. 242-245.
Ronald M. Lechan, et al., *Prosomatostatin-specific antigen in rat brain; Localization by immunocytochemical staining with an antiserum to a synthetic sequence of preprosomatostatin*, Proc. Natl. Acad. Sci. USA, vol. 80, 1983, pp. 2780-2784.
Fukusumi,S., et al., *Identification and Characterization of a Novel Human Cortistain-like Peptide*, Biochemical and Biophysical Research Communications, Academic Press, Inc., Orland, FL, US, vol. 232, No. 1, Mar. 6, 1997, pp. 157-163.
Fukusumi,S., et al., *Identification of a Novel Cortistain-like Peptide in Human*, Pepuchido Kagaku Toronkai Koen Yoshishu, 1996 vol. 34, pp. 9, Retrieved from STN Database accession No. 970321252 (Abstract).
Lecea de,L., et al., *Cloning, mRNA Expression, and Chromosonal Mapping of Mouse and Human Preprocortistain*, Genomics, Academic Press, San Diego, US, vol. 42, No. 3, Jun. 15, 1997, pp. 499-506.

(Continued)

*Primary Examiner*—David Romeo
(74) *Attorney, Agent, or Firm*—Edwards Angell Palmer & Dodge LLP; David G. Conlin, Esq.; Peter C. Lauro, Esq.

(57) ABSTRACT

The peptides and precursors thereof, inclusive salts thereof, of the present invention are useful as a pharmaceutical composition, for example as therapeutic or prophylactic agents for hormone-producing tumors, acromegaly, gigantism, dementia, gastric ulcer and the like, hormone secretion inhibitors, tumor growth inhibitors, neural activity or sleep modulators, etc. The DNAs coding for the peptides or precursors of the invention are useful as a pharmaceutical composition, for example as agents for the gene therapy or prevention of hormone-producing tumors, acromegaly, gigantism, dementia, gastric ulcer and the like, hormone secretion inhibitors, tumor growth inhibitors, neural activity or sleep modulators, etc. Furthermore, the DNAs coding for the peptides or precursors of the invention are useful as agents for the gene diagnosis of various diseases, for example, hormone-producing tumors, acromegaly, gigantism, dementia, gastric ulcer, etc. The antibodies against the peptides, precursors or salts of the invention can be used for assaying the peptides, precursors or salts of the invention in test solutions. The peptides, precursors or salts of the invention are useful as reagents for screening for compounds, or salts thereof, capable of modifying the binding of the peptides, precursors or salts of the invention to certain receptors.

11 Claims, 11 Drawing Sheets

OTHER PUBLICATIONS

Totstivint, H., et al., *Un deuxiéme gene codant pour la somatostatine est exprimé dans le cerveau*, M/S Médecine Sciences, Societe des Periodiques Flammarion, Paris, FR, vol. 12, No. 10, Oct. 1, 1996, pp. 1131-1133.

O. Prospero-Garcia, et al., *Cortistatin Modulates Cortical and Hippocampal Electrophysiological Activity and Sleep*, Society for Neuroscience Abstracts, Society for Neuroscience, US, vol. 22, No. 1/3, Nov. 16, 1996, pp 1152 (Abstract).

Totstivint, H., et al., *Occurrence of two somatostatin variants in the frog brain: Characterization of the cDNAs, distribution of the mRNAs, and receptor-binding affinites of the peptides*, Proceedings of the National Academy of Science, Washington, US, vol. 93, Oct. 1996, pp. 12605-12610.

Fukusumi, S., et al., Bioch and Biphysical Research, 232(1): pp 157-163 (Mar. 6, 1997).

DeLecea, L., et al., Letters to Nature, 381: 242-245 (May 16, 1996).

* cited by examiner

Figure 1

```
         10         20         30         40         50         60
   ACAAGATGCC ATTGTCCCCC GGCCTCCTGC TGCTGCTGCT CTCCGGGGCC ACGGCCACCG
         70         80         90        100        110        120
   CTGCCCTGCC CCTGGAGGGT GGCCCCACCG GCCGAGACAG CGAGCATATG CAGGAAGCGG
        130        140        150        160        170        180
   CAGGAATAAG GAAAAGCAGC CTCCTGACTT TCCTCGCTTG GTGGTTTGAG TGGACCTCCC
        190        200        210        220        230        240
   AGGCCAGTGC CGGGCCCCTC ATAGGAGAGG AAGCTCGGGA GGTGGCCAGG CGGCAGGAAG
        250        260        270        280        290        300
   GCGCACCCCC CCAGCAATCC GCGCGCCGGG ACAGAATGCC CTGCAGGAAC TTCTTCTGGA
        310        320        330        340        350        360
   AGACCTTCTC CTCCTGCAAA TAAAACCTCA CCCATGAATG CTCACGCAAG TTTAATTACA
        370        380        390        400        410        420
   GACCTGAA..  ........   ........   ........   ........   ........
```

Figure 2

```
  3  AAGATGCCATTGTCCCCCGGCCTCCTGCTGCTGCTCCTGTCCGGGGCCACCGCT   62
  1      MetProLeuSerProGlyLeuLeuLeuLeuLeuSerGlyAlaThrAla     19

63  GCCCTGCCCCTGGAGGGTGGCCCCACCGGCCGAGACAGGCATATGCAGGAAGGCA  122
 19   AlaLeuProLeuGluGlyGlyProThrGlyArgAspSerGluHisMetGlnGluAlaAla  39

123  GGAATAAGGAAAAGCAGCCCTCCCTGACTTTCCCTCGCTTGGTTGAGTGGACTCCCAG  182
 39   GlyIleArgLysSerSerLeuLeuThrPheLeuAlaTrpTrpPheGluTrpThrSerGln  59

183  GCCAGTGCCGGGCCCCTCATAGGAGAGGAAGCTCGGGAGGTGGCAGGGGCAGGAAGGC  242
 59   AlaSerAlaGlyProLeuIleGlyGluAlaArgGluValAlaArgArgGlnGluGly    79

243  GCACCCCCCAGCAATCCGGGGACAGAATGCCCGGACTTCTCTGGAAG  302
 79   AlaProProGlnSerAlaArgArgAspArgMetProCysArgAsnPheTrpLys    99

303  ACCTTCTCCTCTGCAAATAAAACCTCACGCAAGTTTAATTACAGA  362
 99    ThrPheSerSerCysLys***                          106

363  CCTGAA  368
106
```

Figure 3

```
  1 ATGCCATTGTCCCCCGGCCTCCCCTGCTGCTCCTCCTGGGCCACGGCCACCGGCTGCC      60
  1 MetProLeuSerProGlyLeuLeuLeuLeuLeuSerGlyAlaThrAlaThrAlaAla        20

61 CTGCCCCTGAGGTGGCCCCACCGGCCCGAGACAGGCGAGCATATGCAGGAAGCGGCAGA    120
 21 LeuProLeuGluGlyGlyProThrGlyArgAspSerGluHisMetGlnGluAlaAlaGly     40

121 ATAAGGAAAAGCCAGCTCCCTGACTTCCTCCGCTTGGTGTTGAGTGGACCTCCAGGCC     180
 41 IleArgLysSerSerLeuLeuThrPheLeuAlaTrpTrpPheGluTrpThrSerGlnAla     60

181 AGTGCCGGGCCCCTCATAGGAGAGGAAGCTCGGGAGGTGGCCAGGCGCAGGAAGGCCA     240
 61 SerAlaGlyProLeuIleGlyGluGluAlaArgGluValAlaArgArgGlnGluGlyAla     80

241 CCCCCCCAGCAATCTGCGCGGGACAGAATGCCCTGCAGGAACTTCTCTGAAGACC       300
 81 ProProGlnSerAlaArgArgAspArgArgMetProCysArgAsnPhePheTrpLysThr    100

301 TTCTCCTCCTGCAAATAA                                             318
101 PheSerSerCysLys***                                             106
```

*P<0.05, compared with vehicle control

*P<0.05, compared with vehicle control

*P<0.05, compared with vehicle control

*P<0.05, compared with vehicle control

SEQUENCE LISTING

<160> NUMBER OF SEQ ID NOS: 121

<210> SEQ ID NO 1
<211> LENGTH: 17
<212> TYPE: PRT
<213> ORGANISM: Homo sapiens

-continued

```
<400> SEQUENCE: 1

Asp Arg Met Pro Cys Arg Asn Phe Phe Trp Lys Thr Phe Ser Ser Cys
 1               5                  10                  15

Lys

<210> SEQ ID NO 2
<211> LENGTH: 15
<212> TYPE: PRT
<213> ORGANISM: Homo sapiens

<400> SEQUENCE: 2

Met Pro Cys Arg Asn Phe Phe Trp Lys Thr Phe Ser Ser Cys Lys
 1               5                  10                  15

<210> SEQ ID NO 3
<211> LENGTH: 13
<212> TYPE: PRT
<213> ORGANISM: Homo sapiens

<400> SEQUENCE: 3

Cys Arg Asn Phe Phe Trp Lys Thr Phe Ser Ser Cys Lys
 1               5                  10

<210> SEQ ID NO 4
<211> LENGTH: 29
<212> TYPE: PRT
<213> ORGANISM: Homo sapiens

<400> SEQUENCE: 4

Gln Glu Gly Ala Pro Pro Gln Gln Ser Ala Arg Arg Asp Arg Met Pro
 1               5                  10                  15

Cys Arg Asn Phe Phe Trp Lys Thr Phe Ser Ser Cys Lys
                 20                  25

<210> SEQ ID NO 5
<211> LENGTH: 62
<212> TYPE: PRT
<213> ORGANISM: Homo sapiens

<400> SEQUENCE: 5

Ser Ser Leu Leu Thr Phe Leu Ala Trp Trp Phe Glu Trp Thr Ser Gln
 1               5                  10                  15

Ala Ser Ala Gly Pro Leu Ile Gly Glu Glu Ala Arg Glu Val Ala Arg
                 20                  25                  30

Arg Gln Glu Gly Ala Pro Pro Gln Gln Ser Ala Arg Arg Asp Arg Met
         35                  40                  45

Pro Cys Arg Asn Phe Phe Trp Lys Thr Phe Ser Ser Cys Lys
         50                  55                  60

<210> SEQ ID NO 6
<211> LENGTH: 85
<212> TYPE: PRT
<213> ORGANISM: Homo sapiens

<400> SEQUENCE: 6

Leu Pro Leu Glu Gly Gly Pro Thr Gly Arg Asp Ser Glu His Met Gln
 1               5                  10                  15

Glu Ala Ala Gly Ile Arg Lys Ser Ser Leu Leu Thr Phe Leu Ala Trp
                 20                  25                  30

Trp Phe Glu Trp Thr Ser Gln Ala Ser Ala Gly Pro Leu Ile Gly Glu
```

-continued

```
                35                  40                  45
Glu Ala Arg Glu Val Ala Arg Gln Glu Gly Ala Pro Pro Gln Gln
     50                  55                  60
Ser Ala Arg Arg Asp Arg Met Pro Cys Arg Asn Phe Phe Trp Lys Thr
 65                  70                  75                  80
Phe Ser Ser Cys Lys
             85

<210> SEQ ID NO 7
<211> LENGTH: 105
<212> TYPE: PRT
<213> ORGANISM: Homo sapiens

<400> SEQUENCE: 7

Met Pro Leu Ser Pro Gly Leu Leu Leu Leu Ser Gly Ala Thr
  1               5                  10                  15
Ala Thr Ala Ala Leu Pro Leu Glu Gly Gly Pro Thr Gly Arg Asp Ser
                 20                  25                  30
Glu His Met Gln Glu Ala Ala Gly Ile Arg Lys Ser Ser Leu Leu Thr
             35                  40                  45
Phe Leu Ala Trp Trp Phe Glu Trp Thr Ser Gln Ala Ser Ala Gly Pro
     50                  55                  60
Leu Ile Gly Glu Glu Ala Arg Glu Val Ala Arg Arg Gln Glu Gly Ala
 65                  70                  75                  80
Pro Pro Gln Gln Ser Ala Arg Arg Asp Arg Met Pro Cys Arg Asn Phe
                 85                  90                  95
Phe Trp Lys Thr Phe Ser Ser Cys Lys
            100                 105

<210> SEQ ID NO 8
<211> LENGTH: 12
<212> TYPE: PRT
<213> ORGANISM: Homo sapiens

<400> SEQUENCE: 8

Gln Glu Gly Ala Pro Pro Gln Gln Ser Ala Arg Arg
  1               5                  10

<210> SEQ ID NO 9
<211> LENGTH: 33
<212> TYPE: PRT
<213> ORGANISM: Homo sapiens

<400> SEQUENCE: 9

Ser Ser Leu Leu Thr Phe Leu Ala Trp Trp Phe Glu Trp Thr Ser Gln
  1               5                  10                  15
Ala Ser Ala Gly Pro Leu Ile Gly Glu Glu Ala Arg Glu Val Ala Arg
                 20                  25                  30
Arg

<210> SEQ ID NO 10
<211> LENGTH: 23
<212> TYPE: PRT
<213> ORGANISM: Homo sapiens

<400> SEQUENCE: 10

Leu Pro Leu Glu Gly Gly Pro Thr Gly Arg Asp Ser Glu His Met Gln
  1               5                  10                  15
Glu Ala Ala Gly Ile Arg Lys
```

<210> SEQ ID NO 11
<211> LENGTH: 20
<212> TYPE: PRT
<213> ORGANISM: Homo sapiens

<400> SEQUENCE: 11

Met Pro Leu Ser Pro Gly Leu Leu Leu Leu Leu Ser Gly Ala Thr
 1               5                  10                  15
Ala Thr Ala Ala
            20

<210> SEQ ID NO 12
<211> LENGTH: 88
<212> TYPE: PRT
<213> ORGANISM: Homo sapiens

<400> SEQUENCE: 12

Met Pro Leu Ser Pro Gly Leu Leu Leu Leu Leu Ser Gly Ala Thr
 1               5                  10                  15
Ala Thr Ala Ala Leu Pro Leu Glu Gly Gly Pro Thr Gly Arg Asp Ser
            20                  25                  30
Glu His Met Gln Glu Ala Ala Gly Ile Arg Lys Ser Ser Leu Leu Thr
        35                  40                  45
Phe Leu Ala Trp Trp Phe Glu Trp Thr Ser Gln Ala Ser Ala Gly Pro
    50                  55                  60
Leu Ile Gly Glu Glu Ala Arg Glu Val Ala Arg Arg Gln Glu Gly Ala
65                  70                  75                  80
Pro Pro Gln Gln Ser Ala Arg Arg
                85

<210> SEQ ID NO 13
<211> LENGTH: 51
<212> TYPE: DNA
<213> ORGANISM: Homo sapiens

<400> SEQUENCE: 13
gacagaatgc cctgcaggaa cttcttctgg aagaccttct cctcctgcaa a         51

<210> SEQ ID NO 14
<211> LENGTH: 45
<212> TYPE: DNA
<213> ORGANISM: Homo sapiens

<400> SEQUENCE: 14
atgccctgca ggaacttctt ctggaagacc ttctcctcct gcaaa              45

<210> SEQ ID NO 15
<211> LENGTH: 39
<212> TYPE: DNA
<213> ORGANISM: Homo sapiens

<400> SEQUENCE: 15
tgcaggaact tcttctggaa gaccttctcc tcctgcaaa                    39

<210> SEQ ID NO 16
<211> LENGTH: 87
<212> TYPE: DNA
<213> ORGANISM: Homo sapiens

<400> SEQUENCE: 16

```
caggaaggcg cacccccca gcaatccgcg cgccgggaca gaatgccctg caggaacttc      60
ttctggaaga ccttctcctc ctgcaaa                                         87

<210> SEQ ID NO 17
<211> LENGTH: 87
<212> TYPE: DNA
<213> ORGANISM: Homo sapiens

<400> SEQUENCE: 17
caggaaggcg cacccccca gcaatctgcg cgccgggaca gaatgccctg caggaacttc      60
ttctggaaga ccttctcctc ctgcaaa                                         87

<210> SEQ ID NO 18
<211> LENGTH: 186
<212> TYPE: DNA
<213> ORGANISM: Homo sapiens

<400> SEQUENCE: 18
agcagcctcc tgactttcct cgcttggtgg tttgagtgga cctcccaggc cagtgccggg     60
cccctcatag gagaggaagc tcgggaggtg gccaggcggc aggaaggcgc acccccccag   120
caatccgcgc gccgggacag aatgccctgc aggaacttct tctggaagac cttctcctcc   180
tgcaaa                                                              186

<210> SEQ ID NO 19
<211> LENGTH: 186
<212> TYPE: DNA
<213> ORGANISM: Homo sapiens

<400> SEQUENCE: 19
agcagcctcc tgactttcct cgcttggtgg tttgagtgga cctcccaggc cagtgccggg     60
cccctcatag gagaggaagc tcgggaggtg gccaggcggc aggaaggcgc acccccccag   120
caatctgcgc gccgggacag aatgccctgc aggaacttct tctggaagac cttctcctcc   180
tgcaaa                                                              186

<210> SEQ ID NO 20
<211> LENGTH: 255
<212> TYPE: DNA
<213> ORGANISM: Homo sapiens

<400> SEQUENCE: 20
ctgcccctgg agggtggccc caccggccga gacagcgagc atatgcagga agcggcagga     60
ataaggaaaa gcagcctcct gactttcctc gcttggtggt ttgagtggac ctcccaggcc   120
agtgccgggc ccctcatagg agaggaagct cgggaggtgg ccaggcggca ggaaggcgca   180
cccccccagc aatccgcgcg ccgggacaga atgccctgca ggaacttctt ctggaagacc   240
ttctcctcct gcaaa                                                    255

<210> SEQ ID NO 21
<211> LENGTH: 255
<212> TYPE: DNA
<213> ORGANISM: Homo sapiens

<400> SEQUENCE: 21
ctgcccctgg agggtggccc caccggccga gacagcgagc atatgcagga agcggcagga     60
ataaggaaaa gcagcctcct gactttcctc gcttggtggt ttgagtggac ctcccaggcc   120
```
agtgccgggc ccctcatagg agaggaagct cgggaggtgg ccaggcggca ggaaggcgca    180
cccccccagc aatctgcgcg ccgggacaga atgccctgca ggaacttctt ctggaagacc    240
ttctcctcct gcaaa    255

<210> SEQ ID NO 22
<211> LENGTH: 315
<212> TYPE: DNA
<213> ORGANISM: Homo sapiens

<400> SEQUENCE: 22
atgccattgt cccccggcct cctgctgctg ctgctctccg gggccacggc caccgctgcc     60
ctgcccctgg agggtggccc caccggccga dacagcgagc atatgcagga agcggcagga    120
ataaggaaaa gcagcctcct gactttcctc gcttggtggt ttgagtggac ctcccaggcc    180
agtgccgggc ccctcatagg agaggaagct cgggaggtgg ccaggcggca ggaaggcgca    240
cccccccagc aatccgcgcg ccgggacaga atgccctgca ggaacttctt ctggaagacc    300
ttctcctcct gcaaa    315

<210> SEQ ID NO 23
<211> LENGTH: 315
<212> TYPE: DNA
<213> ORGANISM: Homo sapiens

<400> SEQUENCE: 23
atgccattgt cccccggcct cctgctgctg ctgctctccg gggccacggc caccgctgcc     60
ctgcccctgg agggtggccc caccggccga dacagcgagc atatgcagga agcggcagga    120
ataaggaaaa gcagcctcct gactttcctc gcttggtggt ttgagtggac ctcccaggcc    180
agtgccgggc ccctcatagg agaggaagct cgggaggtgg ccaggcggca ggaaggcgca    240
cccccccagc aatctgcgcg ccgggacaga atgccctgca ggaacttctt ctggaagacc    300
ttctcctcct gcaaa    315

<210> SEQ ID NO 24
<211> LENGTH: 36
<212> TYPE: DNA
<213> ORGANISM: Homo sapiens

<400> SEQUENCE: 24
caggaaggcg cacccccca gcaatccgcg cgccgg    36

<210> SEQ ID NO 25
<211> LENGTH: 36
<212> TYPE: DNA
<213> ORGANISM: Homo sapiens

<400> SEQUENCE: 25
caggaaggcg cacccccca gcaatctgcg cgccgg    36

<210> SEQ ID NO 26
<211> LENGTH: 99
<212> TYPE: DNA
<213> ORGANISM: Homo sapiens

<400> SEQUENCE: 26
agcagcctcc tgactttcct cgcttggtgg tttgagtgga cctcccaggc cagtgccggg     60
cccctcatag gagaggaagc tcgggaggtg gccaggcgg    99

<210> SEQ ID NO 27
<211> LENGTH: 69
<212> TYPE: DNA
<213> ORGANISM: Homo sapiens

<400> SEQUENCE: 27
ctgcccctgg agggtggccc caccggccga gacagcgagc atatgcagga agcggcagga    60
ataaggaaa                                                            69

<210> SEQ ID NO 28
<211> LENGTH: 60
<212> TYPE: DNA
<213> ORGANISM: Homo sapiens

<400> SEQUENCE: 28
atgccattgt cccccggcct cctgctgctg ctgctctccg gggccacggc caccgctgcc    60

<210> SEQ ID NO 29
<211> LENGTH: 264
<212> TYPE: DNA
<213> ORGANISM: Homo sapiens

<400> SEQUENCE: 29
atgccattgt cccccggcct cctgctgctg ctgctctccg gggccacggc caccgctgcc    60
ctgcccctgg agggtggccc caccggccga gacagcgagc atatgcagga agcggcagga   120
ataaggaaaa gcagcctcct gactttcctc gcttggtggt ttgagtggac ctcccaggcc   180
agtgccgggc ccctcatagg agaggaagct cgggaggtgg ccaggcggca ggaaggcgca   240 ccccccagc aatccgcgcg ccgg                                           264

<210> SEQ ID NO 30
<211> LENGTH: 264
<212> TYPE: DNA
<213> ORGANISM: Homo sapiens

<400> SEQUENCE: 30
atgccattgt cccccggcct cctgctgctg ctgctctccg gggccacggc caccgctgcc    60
ctgcccctgg agggtggccc caccggccga gacagcgagc atatgcagga agcggcagga   120
ataaggaaaa gcagcctcct gactttcctc gcttggtggt ttgagtggac ctcccaggcc   180
agtgccgggc ccctcatagg agaggaagct cgggaggtgg ccaggcggca ggaaggcgca   240 ccccccagc aatctgcgcg ccgg                                           264

<210> SEQ ID NO 31
<211> LENGTH: 14
<212> TYPE: PRT
<213> ORGANISM: Rattus sp.

<400> SEQUENCE: 31

Pro Cys Lys Asn Phe Phe Trp Lys Thr Phe Ser Ser Cys Lys
 1               5                  10

<210> SEQ ID NO 32
<211> LENGTH: 14
<212> TYPE: PRT
<213> ORGANISM: Rattus sp.

<400> SEQUENCE: 32

Ala Gly Cys Lys Asn Phe Phe Trp Lys Thr Phe Thr Ser Cys
 1               5                  10

<210> SEQ ID NO 33
<211> LENGTH: 42
<212> TYPE: DNA
<213> ORGANISM: Rattus sp.

<400> SEQUENCE: 33
ccctgcaaga acttcttctg gaaaaccttc tcctcgtgca ag                               42

<210> SEQ ID NO 34
<211> LENGTH: 42
<212> TYPE: DNA
<213> ORGANISM: Rattus sp.

<400> SEQUENCE: 34
gctggctgca agaacttctt ctggaagaca ttcacatcct gt                               42

<210> SEQ ID NO 35
<211> LENGTH: 16
<212> TYPE: PRT
<213> ORGANISM: Homo sapiens

<400> SEQUENCE: 35

Asp Arg Met Pro Cys Arg Asn Phe Phe Trp Lys Thr Phe Ser Ser Cys
 1               5                  10                  15

<210> SEQ ID NO 36
<211> LENGTH: 14
<212> TYPE: PRT
<213> ORGANISM: Homo sapiens

<400> SEQUENCE: 36

Met Pro Cys Arg Asn Phe Phe Trp Lys Thr Phe Ser Ser Cys
 1               5                  10

<210> SEQ ID NO 37
<211> LENGTH: 12
<212> TYPE: PRT
<213> ORGANISM: Homo sapiens

<400> SEQUENCE: 37

Cys Arg Asn Phe Phe Trp Lys Thr Phe Ser Ser Cys
 1               5                  10

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Met Pro Cys Lys Asn Phe Phe Trp Lys Thr Phe Ser Ser Cys
 1               5                  10                  15

Lys

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

-continued

Met Pro Cys Lys Asn Phe Phe Trp Lys Thr Phe Ser Ser Cys Lys
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Lys Asn Phe Phe Trp Lys Thr Phe Ser Ser Cys Lys
 1               5                  10

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Arg Met Pro Cys Lys Asn Phe Phe Trp Lys Thr Phe Ser Ser Cys
 1               5                  10                  15

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Pro Cys Lys Asn Phe Phe Trp Lys Thr Phe Ser Ser Cys
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Lys Asn Phe Phe Trp Lys Thr Phe Ser Ser Cys
 1               5                  10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Met Pro Cys Arg Asn Phe Phe Trp Lys Thr Phe Thr Ser Cys
 1               5                  10                  15

Lys

<210> SEQ ID NO 45
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Pro Cys Arg Asn Phe Phe Trp Lys Thr Phe Thr Ser Cys Lys
 1               5                  10                  15

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Arg Asn Phe Phe Trp Lys Thr Phe Thr Ser Cys Lys
 1               5                  10

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Arg Met Pro Cys Arg Asn Phe Phe Trp Lys Thr Phe Thr Ser Cys
 1               5                  10                  15

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Pro Cys Arg Asn Phe Phe Trp Lys Thr Phe Thr Ser Cys
 1               5                  10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Arg Asn Phe Phe Trp Lys Thr Phe Thr Ser Cys
 1               5                  10

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Arg Met Pro Cys Lys Asn Phe Phe Trp Lys Thr Phe Thr Ser Cys
```

```
                1               5                  10                 15
Lys

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Pro Cys Lys Asn Phe Phe Trp Lys Thr Phe Thr Ser Cys Lys
 1               5                  10                  15

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Lys Asn Phe Phe Trp Lys Thr Phe Thr Ser Cys Lys
 1               5                  10

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Met Pro Cys Lys Asn Phe Phe Trp Lys Thr Phe Thr Ser Cys
 1               5                  10                  15

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Pro Cys Lys Asn Phe Phe Trp Lys Thr Phe Thr Ser Cys
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Lys Asn Phe Phe Trp Lys Thr Phe Thr Ser Cys
 1               5                  10

<210> SEQ ID NO 56
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 56

Gln Glu Gly Ala Pro Pro Gln Gln Ser Ala Arg Arg Asp Arg Met Pro
 1               5                  10                  15

Cys Lys Asn Phe Phe Trp Lys Thr Phe Ser Ser Cys Lys
            20                  25

<210> SEQ ID NO 57
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Glu Gly Ala Pro Pro Gln Gln Ser Ala Arg Arg Asp Arg Met Pro
 1               5                  10                  15

Cys Arg Asn Phe Phe Trp Lys Thr Phe Thr Ser Cys Lys
            20                  25

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Glu Gly Ala Pro Pro Gln Gln Ser Ala Arg Arg Asp Arg Met Pro
 1               5                  10                  15

Cys Lys Asn Phe Phe Trp Lys Thr Phe Thr Ser Cys Lys
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Glu Gly Ala Pro Pro Gln Gln Ser Ala Arg Arg Asp Arg Met Pro
 1               5                  10                  15

Cys Lys Asn Phe Phe Trp Lys Thr Phe Ser Ser Cys
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Glu Gly Ala Pro Pro Gln Gln Ser Ala Arg Arg Asp Arg Met Pro
 1               5                  10                  15

Cys Arg Asn Phe Phe Trp Lys Thr Phe Thr Ser Cys
            20                  25
```

```
<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Glu Gly Ala Pro Pro Gln Gln Ser Ala Arg Arg Asp Arg Met Pro
  1               5                  10                  15

Cys Lys Asn Phe Phe Trp Lys Thr Phe Thr Ser Cys
             20                  25

<210> SEQ ID NO 62
<211> LENGTH: 48
<212> TYPE: DNA
<213> ORGANISM: Homo sapiens

<400> SEQUENCE: 62
gacagaatgc cctgcaggaa cttcttctgg aagaccttct cctcctgc                    48

<210> SEQ ID NO 63
<211> LENGTH: 42
<212> TYPE: DNA
<213> ORGANISM: Homo sapiens

<400> SEQUENCE: 63
atgccctgca ggaacttctt ctggaagacc ttctcctcct gc                          42

<210> SEQ ID NO 64
<211> LENGTH: 36
<212> TYPE: DNA
<213> ORGANISM: Homo sapiens

<400> SEQUENCE: 64
tgcaggaact tcttctggaa gaccttctcc tcctgc                                 36

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gacagaatgc cctgcaaraa cttcttctgg aagaccttct cctcctgcaa a                51

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atgccctgca araacttctt ctggaagacc ttctcctcct gcaaa                       45

<210> SEQ ID NO 67
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 67
tgcaaraact tcttctggaa gaccttctcc tcctgcaaa                          39

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gacagaatgc cctgcaaraa cttcttctgg aagaccttct cctcctgcaa a            51

<210> SEQ ID NO 69
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atgccctgca araacttctt ctggaagacc ttctcctcct gcaaa                   45

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgcaaraact tcttctggaa gaccttctcc tcctgcaaa                          39

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)
<223> OTHER INFORMATION: a, t, c, g, unknown or other

<400> SEQUENCE: 71
gacagaatgc cctgcaggaa cttcttctgg aagaccttct ccacntgcaa a            51

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)
<223> OTHER INFORMATION: a, t, c, g, unknown or other

<400> SEQUENCE: 72
```
atgccctgca ggaacttctt ctggaagacc ttcacntcct gcaaa                45

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)
<223> OTHER INFORMATION: a, t, c, g, unknown or other

<400> SEQUENCE: 73
tgcaggaact tcttctggaa gaccttcacn tcctgcaaa                39

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)
<223> OTHER INFORMATION: a, t, c, g, unknown or other

<400> SEQUENCE: 74
gacagaatgc cctgcaggaa cttcttctgg aagaccttct ccacntgc                48

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)
<223> OTHER INFORMATION: a, t, c, g, unknown or other

<400> SEQUENCE: 75
atgccctgca ggaacttctt ctggaagacc ttcacntcct gc                42

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)
<223> OTHER INFORMATION: a, t, c, g, unknown or other

<400> SEQUENCE: 76
tgcaggaact tcttctggaa gaccttcacn tcctgc                36

<210> SEQ ID NO 77
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (45)
<223> OTHER INFORMATION: a, t, c, g, unknown or other

<400> SEQUENCE: 77
gacagaatgc cctgcaaraa cttcttctgg aagaccttct ccacntgcaa a           51

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)
<223> OTHER INFORMATION: a, t, c, g, unknown or other

<400> SEQUENCE: 78
atgccctgca araacttctt ctggaagacc ttcacntcct gcaaa                  45

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)
<223> OTHER INFORMATION: a, t, c, g, unknown or other

<400> SEQUENCE: 79
tgcaaraact tcttctggaa gaccttcacn tcctgcaaa                         39

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)
<223> OTHER INFORMATION: a, t, c, g, unknown or other

<400> SEQUENCE: 80
gacagaatgc cctgcaaraa cttcttctgg aagaccttct ccacntgcaa a           51

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)
<223> OTHER INFORMATION: a, t, c, g, unknown or other

<400> SEQUENCE: 81
atgccctgca araacttctt ctggaagacc ttcacntcct gcaaa                  45

<210> SEQ ID NO 82
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)
<223> OTHER INFORMATION: a, t, c, g, unknown or other

<400> SEQUENCE: 82
tgcaaraact tcttctggaa gaccttcacn tcctgc                               36

<210> SEQ ID NO 83
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
caggaaggcg cacccccca gcaatccgcg cgccgggaca gaatgccctg caaraacttc     60
ttctggaaga ccttctcctc ctgcaaa                                        87

<210> SEQ ID NO 84
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
caggaaggcg cacccccca gcaatctgcg cgccgggaca gaatgccctg caaraacttc     60
ttctggaaga ccttctcctc ctgcaaa                                        87

<210> SEQ ID NO 85
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 85
caggaaggcg cacccccca gcaatccgcg cgccgggaca gaatgccctg caggaacttc     60
ttctggaaga ccttcacntc ctgcaaa                                        87

<210> SEQ ID NO 86
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 86
caggaaggcg cacccccca gcaatctgcg cgccgggaca gaatgccctg caggaacttc     60
```

```
ttctggaaga ccttcacntc ctgcaaa                                    87

<210> SEQ ID NO 87
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 87
caggaaggcg cacccccca gcaatccgcg cgccgggaca gaatgccctg caaraacttc    60
ttctggaaga ccttcacntc ctgcaaa                                      87

<210> SEQ ID NO 88
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 88
caggaaggcg cacccccca gcaatctgcg cgccgggaca gaatgccctg caaraacttc    60
ttctggaaga ccttcacntc ctgcaaa                                      87

<210> SEQ ID NO 89
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caggaaggcg cacccccca gcaatccgcg cgccgggaca gaatgccctg caaraacttc    60
ttctggaaga ccttctcctc ctgc                                         84

<210> SEQ ID NO 90
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caggaaggcg cacccccca gcaatctgcg cgccgggaca gaatgccctg caaraacttc    60
ttctggaaga ccttctcctc ctgc                                         84

<210> SEQ ID NO 91
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<221> NAME/KEY: modified_base
<222> LOCATION: (78)
<223> OTHER INFORMATION: a, t, c, g, unknown or other

<400> SEQUENCE: 91
caggaaggcg caccccccca gcaatccgcg cgccgggaca gaatgccctg caggaacttc      60
ttctggaaga ccttcacntc ctgc                                             84

<210> SEQ ID NO 92
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 92
caggaaggcg caccccccca gcaatctgcg cgccgggaca gaatgccctg caggaacttc      60
ttctggaaga ccttcacntc ctgc                                             84

<210> SEQ ID NO 93
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 93
caggaaggcg caccccccca gcaatccgcg cgccgggaca gaatgccctg caaraacttc      60
ttctggaaga ccttcacntc ctgc                                             84

<210> SEQ ID NO 94
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (78)
<223> OTHER INFORMATION: a, t, c, g, unknown or other

<400> SEQUENCE: 94
caggaaggcg caccccccca gcaatctgcg cgccgggaca gaatgccctg caaraacttc      60
ttctggaaga ccttcacntc ctgc                                             84

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
```
ggtcgacctc agctaggatg ttccccaatg                                        30

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggtcgacccg ggctcagagc gtcgtgat                                          28

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggtcgacacc atggacatgg cggatgag                                          28

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggtcgacagt tcagatactg gtttgg                                            26

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggtcgacctc aaccatggac atgcttcatc                                        30

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggtcgacttt ccccaggccc ctacaggta                                         29

<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggctcgagtc accatgagcg cccccctcg                                         28

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gggctcgagc tcctcagaag gtggtgg                                27

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
ggtcgaccac catggagccc ctgttccc                              28

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
ccgtcgacac tctcacagct tgctgg                                26

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
acaagatgcc attgtccccc ggcctcct                              28

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
ttcaggtctg taattaaact tgcgtga                               27

<210> SEQ ID NO 107
<211> LENGTH: 368
<212> TYPE: DNA
<213> ORGANISM: Homo sapiens
<220> FEATURE:
<223> OTHER INFORMATION: Description of Artificial Sequence: Synthetic oligonucleotide

<400> SEQUENCE: 107
acaagatgcc attgtccccc ggcctcctgc tgctgctgct ctccggggcc acggccaccg     60

```
ctgccctgcc cctggagggt ggccccaccg gccgagacag cgagcatatg caggaagcgg      120
caggaataag gaaaagcagc ctcctgactt tcctcgcttg gtggtttgag tggacctccc      180
aggccagtgc cgggcccctc ataggagagg aagctcggga ggtggccagg cggcaggaag      240
gcgcaccccc ccagcaatcc gcgcgccggg acagaatgcc ctgcaggaac ttcttctgga      300
agaccttctc ctcctgcaaa taaaacctca cccatgaatg ctcacgcaag tttaattaca      360
gacctgaa                                                              368
```

<210> SEQ ID NO 108
<211> LENGTH: 366
<212> TYPE: DNA
<213> ORGANISM: Homo sapiens
<220> FEATURE:
<221> NAME/KEY: CDS
<222> LOCATION: (4)..(318)

<400> SEQUENCE: 108

```
aag atg cca ttg tcc ccc ggc ctc ctg ctg ctg ctg ctc tcc ggg gcc       48
    Met Pro Leu Ser Pro Gly Leu Leu Leu Leu Leu Leu Ser Gly Ala
    1               5                  10                  15 acg gcc acc gct gcc ctg ccc ctg gag ggt ggc ccc acc ggc cga gac       96
Thr Ala Thr Ala Ala Leu Pro Leu Glu Gly Gly Pro Thr Gly Arg Asp
            20                  25                  30 agc gag cat atg cag gaa gcg gca gga ata agg aaa agc agc ctc ctg      144
Ser Glu His Met Gln Glu Ala Ala Gly Ile Arg Lys Ser Ser Leu Leu
        35                  40                  45 act ttc ctc gct tgg tgg ttt gag tgg acc tcc cag gcc agt gcc ggg      192
Thr Phe Leu Ala Trp Trp Phe Glu Trp Thr Ser Gln Ala Ser Ala Gly
    50                  55                  60 ccc ctc ata gga gag gaa gct cgg gag gtg gcc agg cgg cag gaa ggc      240
Pro Leu Ile Gly Glu Glu Ala Arg Glu Val Ala Arg Arg Gln Glu Gly
65                  70                  75 gca ccc ccc cag caa tcc gcg cgc cgg gac aga atg ccc tgc agg aac      288
Ala Pro Pro Gln Gln Ser Ala Arg Arg Asp Arg Met Pro Cys Arg Asn
    80                  85                  90                  95 ttc ttc tgg aag acc ttc tcc tcc tgc aaa taaaacctca cccatgaatg        338
Phe Phe Trp Lys Thr Phe Ser Ser Cys Lys
                100                 105 ctcacgcaag tttaattaca gacctgaa                                       366
```

<210> SEQ ID NO 109
<211> LENGTH: 105
<212> TYPE: PRT
<213> ORGANISM: Homo sapiens

<400> SEQUENCE: 109

```
Met Pro Leu Ser Pro Gly Leu Leu Leu Leu Leu Leu Ser Gly Ala Thr
1               5                  10                  15

Ala Thr Ala Ala Leu Pro Leu Glu Gly Gly Pro Thr Gly Arg Asp Ser
            20                  25                  30

Glu His Met Gln Glu Ala Ala Gly Ile Arg Lys Ser Ser Leu Leu Thr
        35                  40                  45

Phe Leu Ala Trp Trp Phe Glu Trp Thr Ser Gln Ala Ser Ala Gly Pro
    50                  55                  60

Leu Ile Gly Glu Glu Ala Arg Glu Val Ala Arg Arg Gln Glu Gly Ala
65                  70                  75                  80

Pro Pro Gln Gln Ser Ala Arg Arg Asp Arg Met Pro Cys Arg Asn Phe
                85                  90                  95
```

Phe Trp Lys Thr Phe Ser Ser Cys Lys
            100                 105

<210> SEQ ID NO 110
<211> LENGTH: 318
<212> TYPE: DNA
<213> ORGANISM: Homo sapiens
<220> FEATURE:
<221> NAME/KEY: CDS
<222> LOCATION: (1)..(315)

<400> SEQUENCE: 110

| atg cca ttg tcc ccc ggc ctc ctg ctg ctg ctc tcc ggg gcc acg | 48 |
|---|---|
| Met Pro Leu Ser Pro Gly Leu Leu Leu Leu Leu Ser Gly Ala Thr | |
| 1               5                   10                  15 | |
| gcc acc gct gcc ctg ccc ctg gag ggt ggc ccc acc ggc cga gac agc | 96 |
| Ala Thr Ala Ala Leu Pro Leu Glu Gly Gly Pro Thr Gly Arg Asp Ser | |
|                 20                  25                  30 | |
| gag cat atg cag gaa gcg gca gga ata agg aaa agc agc ctc ctg act | 144 |
| Glu His Met Gln Glu Ala Ala Gly Ile Arg Lys Ser Ser Leu Leu Thr | |
|         35                  40                  45 | |
| ttc ctc gct tgg tgg ttt gag tgg acc tcc cag gcc agt gcc ggg ccc | 192 |
| Phe Leu Ala Trp Trp Phe Glu Trp Thr Ser Gln Ala Ser Ala Gly Pro | |
|  50                  55                  60 | |
| ctc ata gga gag gaa gct cgg gag gtg gcc agg cgg cag gaa ggc gca | 240 |
| Leu Ile Gly Glu Glu Ala Arg Glu Val Ala Arg Arg Gln Glu Gly Ala | |
| 65                  70                  75                  80 | |
| ccc ccc cag caa tct gcg cgc cgg gac aga atg ccc tgc agg aac ttc | 288 |
| Pro Pro Gln Gln Ser Ala Arg Arg Asp Arg Met Pro Cys Arg Asn Phe | |
|                 85                  90                  95 | |
| ttc tgg aag acc ttc tcc tcc tgc aaa taa | 318 |
| Phe Trp Lys Thr Phe Ser Ser Cys Lys | |
|             100                 105 | |

<210> SEQ ID NO 111
<211> LENGTH: 105
<212> TYPE: PRT
<213> ORGANISM: Homo sapiens

<400> SEQUENCE: 111

Met Pro Leu Ser Pro Gly Leu Leu Leu Leu Leu Ser Gly Ala Thr
1               5                   10                  15

Ala Thr Ala Ala Leu Pro Leu Glu Gly Gly Pro Thr Gly Arg Asp Ser
                20                  25                  30

Glu His Met Gln Glu Ala Ala Gly Ile Arg Lys Ser Ser Leu Leu Thr
        35                  40                  45

Phe Leu Ala Trp Trp Phe Glu Trp Thr Ser Gln Ala Ser Ala Gly Pro
 50                  55                  60

Leu Ile Gly Glu Glu Ala Arg Glu Val Ala Arg Arg Gln Glu Gly Ala
65                  70                  75                  80

Pro Pro Gln Gln Ser Ala Arg Arg Asp Arg Met Pro Cys Arg Asn Phe
                85                  90                  95

Phe Trp Lys Thr Phe Ser Ser Cys Lys
            100                 105

<210> SEQ ID NO 112
<211> LENGTH: 105
<212> TYPE: PRT
<213> ORGANISM: Homo sapiens

<400> SEQUENCE: 112

-continued

```
Met Pro Leu Ser Pro Gly Arg Asp Ser Glu His Met Gln Glu Ala Ala
  1               5                  10                  15

Gly Ile Arg Lys Ser Ser Glu Ala Arg Glu Val Ala Arg Arg Gln Glu
             20                  25                  30

Gly Ala Pro Pro Gln Gln Ser Gly Leu Leu Leu Leu Leu Leu Ser Gly
         35                  40                  45

Ala Thr Ala Thr Ala Ala Leu Pro Leu Glu Gly Gly Pro Thr Leu Leu
     50                  55                  60

Thr Phe Leu Ala Trp Trp Phe Glu Trp Thr Ser Gln Ala Ser Ala Gly
 65                  70                  75                  80

Pro Leu Ile Gly Glu Ala Arg Arg Asp Arg Met Pro Cys Arg Asn Phe
                 85                  90                  95

Phe Trp Lys Thr Phe Ser Ser Cys Lys
                100                 105

<210> SEQ ID NO 113
<211> LENGTH: 112
<212> TYPE: PRT
<213> ORGANISM: Rattus sp.

<400> SEQUENCE: 113

Met Gly Gly Cys Ser Thr Arg Gly Lys Arg Pro Ser Pro Thr Gly Gln
  1               5                  10                  15

Asp Ser Val Gln Asp Ala Thr Gly Gly Arg Arg Thr Gly Gly Thr Pro
             20                  25                  30

Glu Leu Ser Lys Arg Gln Glu Arg Pro Pro Leu Gln Gln Pro Ala Leu
         35                  40                  45

Ser Leu Leu Leu Leu Leu Leu Ser Gly Ile Ala Ala Ser Ala Leu
     50                  55                  60

Pro Leu Glu Ser Gly Leu Leu Thr Phe Leu Ala Trp Trp His Glu Trp
 65                  70                  75                  80

Ala Ser Gln Asp Ser Ser Thr Ala Phe Glu Gly Pro His Arg Asp
                 85                  90                  95

Lys Lys Pro Cys Lys Asn Phe Phe Trp Lys Thr Phe Ser Ser Cys Lys
                100                 105                 110

<210> SEQ ID NO 114
<211> LENGTH: 116
<212> TYPE: PRT
<213> ORGANISM: Rattus sp.

<400> SEQUENCE: 114

Met Leu Ser Cys Arg Leu Gln Cys Ala Leu Ala Ala Leu Cys Ile Val
  1               5                  10                  15

Leu Ala Ala Thr Gly Lys Gln Glu Leu Ala Lys Tyr Phe Leu Ala Glu
             20                  25                  30

Leu Leu Glu Met Arg Leu Glu Leu Gln Arg Ser Ala Asn Ser Asn Pro
         35                  40                  45

Ala Met Ala Ala Leu Gly Gly Val Thr Gly Ala Pro Ser Asp Pro Arg
     50                  55                  60

Leu Arg Gln Phe Leu Gln Lys Ser Leu Ala Ser Glu Pro Asn Gln Thr
 65                  70                  75                  80

Glu Asn Asp Ala Leu Glu Pro Glu Asp Leu Pro Gln Ala Ala Glu Gln
                 85                  90                  95

Asp Pro Arg Glu Arg Lys Ala Gly Cys Lys Asn Phe Phe Trp Lys Thr
                100                 105                 110
```

Phe Thr Ser Cys
        115

<210> SEQ ID NO 115
<211> LENGTH: 17
<212> TYPE: PRT
<213> ORGANISM: Artificial sequence
<220> FEATURE:
<223> OTHER INFORMATION: Description of Artificial Sequence: Formula
      peptide
<220> FEATURE:
<221> NAME/KEY: MISC_FEATURE
<222> LOCATION: (1)
<223> OTHER INFORMATION: may or may not be present
<220> FEATURE:
<221> NAME/KEY: MISC_FEATURE
<222> LOCATION: (1-2)
<223> OTHER INFORMATION: may or may not be present
<220> FEATURE:
<221> NAME/KEY: MISC_FEATURE
<222> LOCATION: (1-3)
<223> OTHER INFORMATION: may or may not be present
<220> FEATURE:
<221> NAME/KEY: MISC_FEATURE
<222> LOCATION: (1-4)
<223> OTHER INFORMATION: may or may not be present
<220> FEATURE:
<221> NAME/KEY: MISC_FEATURE
<222> LOCATION: (6)
<223> OTHER INFORMATION: Arg or Lys
<220> FEATURE:
<221> NAME/KEY: MISC_FEATURE
<222> LOCATION: (14)
<223> OTHER INFORMATION: Ser or Thr
<220> FEATURE:
<221> NAME/KEY: MISC_FEATURE
<222> LOCATION: (17)
<223> OTHER INFORMATION: may or may not be present

<400> SEQUENCE: 115

Asp Arg Met Pro Cys Xaa Asn Phe Phe Trp Lys Thr Phe Xaa Ser Cys
 1               5                  10                  15
Lys

<210> SEQ ID NO 116
<211> LENGTH: 5
<212> TYPE: PRT
<213> ORGANISM: Homo sapiens

<400> SEQUENCE: 116

Asp Arg Met Pro Cys
 1               5

<210> SEQ ID NO 117
<211> LENGTH: 4
<212> TYPE: PRT
<213> ORGANISM: Homo sapiens

<400> SEQUENCE: 117

Arg Met Pro Cys
 1

<210> SEQ ID NO 118
<211> LENGTH: 14
<212> TYPE: PRT
<213> ORGANISM: Artificial sequence
<220> FEATURE:
<223> OTHER INFORMATION: Description of Artificial Sequence: Synthetic
      peptide

<400> SEQUENCE: 118

Pro Cys Lys Asn Phe Phe Trp Lys Thr Phe Ser Ser Cys Lys
 1               5                  10

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asp(OcHex)
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Cys(MeBzl)
<220> FEATURE:
<221> NAME/KEY: MOD_RES
<222> LOCATION: (6)
<223> OTHER INFORMATION: Arg(Tos)
<220> FEATURE:
<221> NAME/KEY: MOD_RES
<222> LOCATION: (10)
<223> OTHER INFORMATION: Trp(CHO)
<220> FEATURE:
<221> NAME/KEY: MOD_RES
<222> LOCATION: (11)
<223> OTHER INFORMATION: Lys(Cl-Z)
<220> FEATURE:
<221> NAME/KEY: MOD_RES
<222> LOCATION: (12)
<223> OTHER INFORMATION: Thr(Bzl)
<220> FEATURE:
<221> NAME/KEY: MOD_RES
<222> LOCATION: (14)..(15)
<223> OTHER INFORMATION: Ser(Bzl)
<220> FEATURE:
<221> NAME/KEY: MOD_RES
<222> LOCATION: (16)
<223> OTHER INFORMATION: Cys(MeBzl)
<220> FEATURE:
<221> NAME/KEY: MOD_RES
<222> LOCATION: (17)
<223> OTHER INFORMATION: Lys(Cl-Z)

<400> SEQUENCE: 119

Asp Arg Met Pro Cys Arg Asn Phe Phe Trp Lys Thr Phe Ser Ser Cys
 1               5                  10                  15

Lys

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Cys(MeBzl)
<220> FEATURE:
<221> NAME/KEY: MOD_RES
<222> LOCATION: (4)
<223> OTHER INFORMATION: Arg(Tos)
<220> FEATURE:
<221> NAME/KEY: MOD_RES
<222> LOCATION: (8)

```
<223> OTHER INFORMATION: Trp(CHO)
<220> FEATURE:
<221> NAME/KEY: MOD_RES
<222> LOCATION: (9)
<223> OTHER INFORMATION: Lys(Cl-Z)
<220> FEATURE:
<221> NAME/KEY: MOD_RES
<222> LOCATION: (10)
<223> OTHER INFORMATION: Thr(Bzl)
<220> FEATURE:
<221> NAME/KEY: MOD_RES
<222> LOCATION: (12)..(13)
<223> OTHER INFORMATION: Ser(Bzl)
<220> FEATURE:
<221> NAME/KEY: MOD_RES
<222> LOCATION: (14)
<223> OTHER INFORMATION: Cys(MeBzl)
<220> FEATURE:
<221> NAME/KEY: MOD_RES
<222> LOCATION: (15)
<223> OTHER INFORMATION: Lys(CL-Z)

<400> SEQUENCE: 120

Met Pro Cys Arg Asn Phe Phe Trp Lys Thr Phe Ser Ser Cys Lys
 1               5                  10                  15

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys(MeBzl)
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (6)
<223> OTHER INFORMATION: Trp(CHO)
<220> FEATURE:
<221> NAME/KEY: MOD_RES
<222> LOCATION: (7)
<223> OTHER INFORMATION: Lys(CL-Z)
<220> FEATURE:
<221> NAME/KEY: MOD_RES
<222> LOCATION: (8)
<223> OTHER INFORMATION: Thr(Bzl)
<220> FEATURE:
<221> NAME/KEY: MOD_RES
<222> LOCATION: (10)..(11)
<223> OTHER INFORMATION: Ser(Bzl)
<220> FEATURE:
<221> NAME/KEY: MOD_RES
<222> LOCATION: (12)
<223> OTHER INFORMATION: Cys(MeBzl)
<220> FEATURE:
<221> NAME/KEY: MOD_RES
<222> LOCATION: (13)
<223> OTHER INFORMATION: Lys(Cl-Z)

<400> SEQUENCE: 121

Cys Arg Asn Phe Phe Trp Lys Thr Phe Ser Ser Cys Lys
 1               5                  10
```

PEPTIDES AND PRODUCTION AND USE THEREOF

This application is a continuation in part of PCT/JP97/01911, filed on Jun. 5, 1997, claiming priority from JP146052 (filed on Jun. 7, 1996), JP247710 (filed on Sep. 19, 1996) and JP272422 (filed on Oct. 15, 1996).

TECHNICAL FIELD

The present invention relates to novel physiologically active peptides, particularly peptides having human somatostatin-like or cortistatin-like activity, and precursors thereof.

BACKGROUND ART

Somatostatin was isolated from ovine hypothalamus and identified as a growth hormone inhibiting factor (Guillemin, R. et al., Science, vol. 179, pp. 77–79, 1973). Somatostatin is composed of 14 amino acid residues and has a cyclic structure resulting from the S—S bond between Cys in position 3 and Cys in position 14 (somatostatin-14). Somatostatin-28, which is composed of somatostatin-14 and 14 amino acid residues added to the N-terminus of the somatostatin-14 molecule, has also been identified.

Somatostatin is broadly distributed in the central nervous system and, peripherally, occurs in such organs as the spleen and gastrointestinal tract, and further in the peripheral nerves. It is now known that this substance inhibits not only secretion of growth hormone but also secretion of pituitary hormones such as thyroid-stimulating hormone and prolactin and digestive tract hormones such as gastrin and insulin and that it also acts as a neurotransmitter (Brownstain, M. et al., Endocrinology, vol. 96, pp. 1456–1461, 1975). Furthermore, it has been found to inhibit cell proliferation. Therefore, various derivatives of somatostatin have been synthesized and tried for clinical application for the purpose of inhibiting hormone hypersecretion or tumor growth.

A novel neuropeptide similar in structure to somatostatin has been reported by a team of researchers at Scrips Laboratories. It has been revealed that this peptide named rat cortistatin (the precursor thereof being referred to as preprocortistatin) is the product of a gene different from the somatostatin gene. However, cortistatin has the property to selectively shorten the REM (rapid eye movement) sleep phase during sleep and generate low-frequency waves in the cerebral cortex. Further, cortistatin impedes the effects of acetylcholine, which is itself a REM sleep inducer. It is supposed that cortistatin acts as a modulator of neural activities and sleep (L. de Lecea et al., Nature, 381, 16 May 1996).

The activities of somatostatin depend on its binding to the specific high-affinity receptors (somatostatin receptors) present on the cell membrane and the consequent transduction of its signal through the GTP-binding protein to the intracellular signal transduction system. First, the structure of somatostatin receptor subtype 1 (hereinafter sometimes referred to as SSTR1) and that of subtype 2 (hereinafter sometimes referred to as SSTR2) were determined and reported (Yamada et al., Proc. Natl. Acad. Sci. USA, vol. 89, pp. 251–255, 1992). Then, DNAs coding for subtype 3 (hereinafter sometimes referred to as SSTR3), subtype 4 (hereinafter sometimes referred to as SSTR4) and subtype 5 (hereinafter sometimes referred to as SSTR5), respectively, were cloned (SSTR3: Yamada et al., Molecular Endocrinology, vol. 6, pp. 2136–2142, 1992; SSTR4 and SSTR5: Yamada et al., Biochem. Biophys. Res. Commun., vol. 195, pp. 844–852, 1993). These so-far known five somatostatin receptor subtypes are 42–60% homologous with one another on the amino acid level.

The activities of cortistatin are also supposedly displayed upon its binding to the specific high-affinity receptors on the cell membrane and the consequent transduction of its signal through the GTP-binding protein to the intracellular signal transduction system. In fact, cortistatin-14 undergoes a displacement similar to that of somatostatin in response to the binding of [$^{125}$I]-labeled somatostatin on the membrane of the rat pituitary cell GH4 (L. de Lecea et al., Nature, 381, 16 May 1996). However, a possible difference in effect, for example on sleep, has been suggested between somatostatin-14 and cortistatin-14 intraventricularly administered to rats, and differences in affinity and site of action have been implied between the respective peptides with respect to somatostatin receptor subtypes and somatostatin receptor-like receptors. Furthermore, the probability has been pointed out that cortistatin also acts on receptors other than somatostatin receptors. For instance, GPR7 (U22491) and GPR8 (U22492) are reported to be receptors with high homology to somatostatin receptors although the binding thereof to somatostatin has not been established as yet [Genomics, 28, 84–91, (1995)]. It is considered possible that cortistatin act on such receptors as well. As mentioned above, cortistatin supposedly plays important roles in the regulation of physiological functions in vivo via specific receptors but no human-related somatostatin-like or cortistatin-like peptides are known as yet.

Attempts have been reportedly made to determine gene expression levels or discover novel genes in organs and cells by determining partial sequences (expressed sequence tags; abbreviated as ESTs) of cDNA clones randomly selected from among cDNA libraries. M. D. Adams et al. have reported a number of ESTs obtained from a brain cDNA library (Nature Genetics, vol. 4, pp. 373–380, 1993).

The novel physiologically active peptides having somatostatin-like or cortistatin-like activity are expected to enable development of novel drugs of value in the prevention or treatment of acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, bone fracture, mammary cancer, hyperphagia, polyphagia, burn healing, carcinoma of the uterine cervix, chronic lymphatic leukemia, chronic myelocytic leukemia, chronic pancreatitis, hepatic cirrhosis, colorectal cancer (carcinoma of the colon/rectum), Crohn's disease, dementia, diabetic complications, e.g. diabetic nephropathy, diabetic neuropathy, diabetic retinopathy, etc., gastritis, *Helicobacter pylori* infection, hepatic insufficiency, hepatitis A, hepatitis B, hepatitis C, other types of hepatitis, herpes simplex virus infection, varicella-zoster virus infection, Hodgkin's disease, AIDS virus infection, human papilloma virus infection, hypercalcemia, hypercholesterolemia, hyperglyceridemia, hyperlipemia, miscellaneous infectious diseases, influenza virus infection, insulin-dependent diabetes melitus (type I), invasive staphylococcal infection, malignant melanoma, cancer metastasis, multiple myeloma, allergic rhinitis, nephritis, non-Hodgkin's lymphoma, noninsulin-dependent diabetes melitus (type II), non-small-cell lung cancer, organ transplantation, osteoarthritis, osteomalacia, osteopenia, osteoporosis, ovarian cancer, osteo-Behcet's disease, peptic ulcer, peripheral vascular disease, prostatic cancer, reflux esophagitis, renal failure, rheumatoid arthritis, schizophrenia, sepsis, septic shock, severe systemic fungal infection, small-cell lung cancer, spinal injury, stomach cancer, systemic lupus erythematosus, transient cerebral ischemic attack, pulmonary tuberculosis, valvular heart disease, vascular/multiple infarction-associated dementia, wound healing, insomnia, arthritis, and neurodegenerative disease, among other diseases.

DISCLOSURE OF INVENTION

The present invention relates to novel peptides having useful physiological activities, precursors thereof, or salts thereof, DNAs coding for said peptides or precursors, recombinant vectors, transformants, a method of producing said peptides or precursors, pharmaceutical compositions containing said peptides or precursors, antibodies against said peptides or precursors, a method of screening and a kit for the screening of compounds and salts which are capable of modifying the binding of said peptides to receptors, and compounds, or salts thereof, obtained by using said screening method or screening kit.

As a result of intensive investigations made by them for solving the above problems, the present inventors succeeded in cloning a cDNA having a novel base sequence by constructing primers based on the sequence information on an EST and carrying out RT-PCR using human brain poly(A)$^+$ RNA as the template. Further, the present inventors found that a useful somatostatin-like or cortistatin-like physiologically active peptide forms from the protein encoded by the cDNA obtained in the above manner. Based on these findings, the present inventors made further investigations. As a result, they have now completed the present invention.

The present invention thus provides:
(1) A peptide comprising the amino acid sequence defined under SEQ ID NO:1 or an amino acid sequence derived therefrom by deletion, substitution or insertion of 1 to 5 amino acid residues (except for the amino acid sequence defined under SEQ ID NO:31 or SEQ ID NO:32), a precursor thereof, or a salt of said peptide or precursor;
(2) A peptide or precursor as defined above in paragraph (1) which contains the amino acid sequence defined under SEQ ID NO:1 or an amino acid sequence derived therefrom by deletion or substitution of 1 to amino acid residues;
(3) A peptide as defined above in paragraph (1) which comprises the amino acid sequence defined under SEQ ID NO:1;
(4) A peptide as defined above in paragraph (1) which comprises the amino acid sequence defined under SEQ ID NO:2;
(5) A peptide as defined above in paragraph (1) which comprises the amino acid sequence defined under SEQ ID NO:3;
(6) A peptide as defined above in paragraph (1) which comprises the amino acid sequence defined under any of SEQ ID NO:35 through SEQ ID NO:55;
(7) A precursor as defined above in paragraph (1) which comprises the amino acid sequence defined under SEQ ID NO:4, SEQ ID NO:5, SEQ ID NO:6, or SEQ ID NO:7;
(8) A peptide or precursor as defined above in paragraph (1) which has cortistatin-like or somatostatin-like activity;
(9) A DNA comprising a DNA having a nucleotide sequence coding for a peptide or precursor as defined above in paragraph (1);
(10) A DNA defined above in paragraph (9) which comprises the nucleotide sequence defined under SEQ ID NO:13;
(11) A DNA defined above in paragraph (9) which comprises the nucleotide sequence defined under SEQ ID NO:14;
(12) A DNA defined above in paragraph (9) which comprises the nucleotide sequence defined under SEQ ID NO:15;
(13) A DNA defined above in paragraph (9) which comprises the nucleotide sequence defined under any of SEQ ID NO:16 through SEQ ID NO:23;
(14) A DNA defined above in paragraph (9) which comprises the nucleotide sequence defined under any of SEQ ID NO:62 through SEQ ID NO:82;
(15) A recombinant vector comprising a DNA defined above in paragraph (9);
(16) A transformant harboring the recombinant vector defined above in paragraph (15);
(17) A method of producing the peptide defined above in paragraph (1) or a precursor thereof, or a salt of said peptide or precursor, which comprises culturing the transformant defined above in paragraph (16) to thereby cause production and accumulation of the peptide, precursor or salt defined above in paragraph (1), and harvesting the same;
(18) A pharmaceutical composition which comprises the peptide, precursor or salt defined above in paragraph (1);
(19) A pharmaceutical composition which comprises the DNA defined above in paragraph (9);
(20) A pharmaceutical composition as defined above in paragraph (18) or (19) which is an agent for the treatment or prevention of hormone-producing tumors, acromegaly, giantism, dementia or gastric ulcer, a hormone secretion inhibitor, a tumor growth inhibitor, or a neural activity or sleep modulator;
(21) An antibody against the peptide, precursor or salt defined above in paragraph (1);
(22) A method of screening for a compound, or a salt thereof, which is capable of modifying the binding of the peptide, precursor or salt defined above in paragraph (1) to a receptor to which said peptide, precursor or salt may be conjugated, or a fragment peptide of said receptor, or a salt of said receptor or fragment peptide, which method comprises, on the one hand, (i) bringing the peptide, precursor or salt defined in paragraph (1) into contact with said receptor, fragment peptide or salt to which the peptide, precursor or salt defined in paragraph (1) may be conjugated and, on the other hand, (ii) bringing the peptide, precursor or salt defined in paragraph (1) and a compound to be tested into contact with said receptor, fragment peptide or salt to which the peptide, precursor or salt defined in paragraph (1) may be conjugated, and determining and comparing the levels of binding of the peptide, precursor or salt defined in paragraph (1) to said receptor, fragment peptide or salt in and between the above cases (i) and (ii);
(23) A method of screening for a compound, or a salt thereof, which is capable of modifying the binding of the peptide, precursor or salt defined above in paragraph (1) to a receptor to which said peptide, precursor or salt may be conjugated, or a fragment peptide of said receptor, or a salt of said receptor or fragment peptide, which method comprises, on the one hand, (i) bringing the peptide, precursor or salt defined in paragraph (1) into contact with cells or a cell membrane fraction containing said receptor to which the peptide, precursor or salt defined in paragraph (1) may be conjugated and, on the other hand, (ii) bringing the peptide, precursor or salt defined in paragraph (1) and a compound to be tested into contact with the cells or cell membrane fraction containing said receptor to which the peptide, precursor or salt defined in paragraph (1) may be conjugated, and (I) determining and comparing the levels of binding of the peptide, precursor or salt defined in paragraph (1) to the cells or cell membrane fraction containing said receptor or (II) determining and comparing the cell stimulating activities mediated by said receptor in and between the above cases (i) and (ii);

(24) A screening kit for a compound, or a salt thereof, which is capable of modifying the binding of the peptide, precursor or salt defined above in paragraph (1) to a receptor for said peptide, precursor or salt, or a fragment peptide of said receptor, or a salt of said receptor or fragment peptide, which kit comprises the peptide, precursor or salt defined above in paragraph (1);

(25) A compound, or a salt thereof, which is capable of modifying the binding of the peptide, precursor or salt defined above in paragraph (1) to a receptor for said peptide, precursor or salt, or a fragment peptide of said receptor, or a salt of said receptor or fragment peptide, which has been obtained by using the screening method defined above in paragraph (22) or (23) or the screening kit defined above in paragraph (24);

(26) A pharmaceutical composition which comprises an agonist against a receptor for the peptide, precursor or salt defined above in paragraph (1) as obtained by using the screening method defined above in paragraph (22) or (23) or the screening kit defined above in paragraph (24);

(27) A pharmaceutical composition as defined above in paragraph (26) which is an agent for the treatment or prevention of hormone-producing tumors, acromegaly, giantism, dementia or gastric ulcer, a hormone secretion inhibitor, a tumor growth inhibitor, or a neural activity or sleep modulator;

(28) A pharmaceutical composition which comprises an antagonist against a receptor for the peptide, precursor or salt defined above in paragraph (1) as obtained by using the screening method defined above in paragraph (22) or (23) or the screening kit defined above in paragraph (24);

(29) A pharmaceutical composition as defined above in paragraph (28) which is an agent for the treatment or prevention of dwarfism, agalactia/hypogalactia, or diabetes, a hormone secretion promoter, or a gastrointestinal function modulator;

(30) A method of (1) treating mammals for or protecting mammals from hormone-producing tumors, acromegaly, giantism, dementia or gastric ulcer, (2) inhibiting hormone secretion or tumor growth in mammals, or (3) modulating neural activities or sleep in mammals which comprises administering an effective amount of the peptide, precursor or salt defined above in paragraph (1) to mammals;

(31) A method of (1) treating or preventing mammals from hormone-producing tumors, acromegaly, giantism, dementia or gastric ulcer, (2) inhibiting hormone secretion or tumor growth in mammals, or (3) modulating neural activities or sleep in mammals which comprises administering an effective amount of the DNA defined above in paragraph (9) to mammals;

(32) Use of the peptide, precursor or salt defined above in paragraph (1) in the production of an agent for the treatment or prevention of hormone-producing tumors, acromegaly, giantism, dementia or gastric ulcer, a hormone secretion inhibitor, a tumor growth inhibitor or a neural activity or sleep modulator;

(33) Use of the DNA defined above in paragraph (9) in the production of an agent for the treatment or prevention of hormone-producing tumors, acromegaly, giantism, dementia or gastric ulcer, a hormone secretion inhibitor, a tumor growth inhibitor, or a neural activity or sleep modulator; and

(34) A method of producing the peptide, precursor or salt defined above in paragraph (1) which comprises subjecting an amino terminus-constituting amino acid or peptide and a carboxyl terminus-constituting amino acid or peptide to condensation, if desired followed by intramolecular disulfide bond formation.

The present invention further provides:

(35) A peptide as defined in claim 1 which comprises an amino acid sequence of the formula $$X^1\text{-}X^2\text{-Asn-Phe-Phe-Trp-Lys-Thr-Phe-}X^3\text{-Ser-}X^4 \quad (I)$$
(SEQ ID NO:115)

wherein $X^1$ represents Asp-Arg-Met-Pro-Cys (SEQ ID NO:116), Arg-Met-Pro-Cys (SEQ ID NO:117), Met-Pro-Cys, Pro-Cys or Cys, $X^2$ represents Arg or Lys, $X^3$ represents Ser or Thr and $X^4$ represents Cys-Lys or Cys (except for the amino acid sequence (SEQ ID NO:118) in which $X^1$ is Pro-Cys, $X^2$ is Lys, $X^3$ is Ser and $X^4$ is Cys-Lys);

(36) A method of assaying the peptide, precursor or salt defined above in paragraph (1) which comprises bringing the antibody defined above in paragraph (21) into contact with the peptide, precursor or salt defined in paragraph (1);

(37) A method of assaying the peptide, precursor or salt defined above in paragraph (1) in a test solution which comprises reacting the antibody defined above in paragraph (21) competitively with the test solution and the peptide, precursor or salt defined in paragraph (1) and occurring in a labeled form and determining the proportion of the peptide, precursor or salt defined in paragraph (1) and occurring in labeled form that has been bound to said antibody;

(38) A method of assaying the peptide, precursor or salt defined above in paragraph (1) in a test solution which comprises reacting the test solution with the antibody defined above in paragraph (21) and insolubilized on a carrier and another antibody defined in paragraph (21) and occurring in a labeled form either simultaneously or serially and determining the activity of the label on the insolubilizing carrier;

(39) A pharmaceutical composition which comprises the antibody defined above in paragraph (21) (preferably the antibody defined in paragraph (21) which is capable of neutralizing the activities of the peptide, precursor or salt defined above in paragraph (1));

(40) A pharmaceutical composition as defined above in paragraph (39) which is an agent for the treatment or prevention of dwarfism, agalactia/hypogalactia, or diabetes, a hormone secretion promoter, or a gastrointestinal function modulator;

(41) An oligonucleotide derivative (antisense DNA), or a salt thereof, which has a nucleotide sequence complementary or substantially complementary to that of the DNA defined above in paragraph (9) and is capable of inhibiting the expression of said DNA;

(42) An oligonucleotide derivative as defined above in paragraph (41) in which the nucleotide sequence substantially complementary to that of the DNA defined in paragraph (9) is a nucleotide sequence having a homology of not less than about 70% (preferably not less than about 80%, more preferably not less than about 90%, most preferably not less than about 95%) relative to the whole or a part of the nucleotide sequence complementary to that of said DNA;

(43) A pharmaceutical composition which comprises the oligonucleotide or salt defined above in paragraph (41);

(44) A pharmaceutical composition as defined above in paragraph (43) which is an agent for the treatment or prevention of dwarfism, agalactia/hypogalactia, or diabetes, a hormone secretion promoter, or a gastrointestinal function modulator.

(45) An oligonucleotide, or a salt thereof, which comprises a nucleotide sequence complementary or substantially complementary to that of the DNA defined above in paragraph (9) and is capable of promoting the expression of said DNA;

(46) An oligonucleotide derivative as defined above in paragraph (45) in which the nucleotide sequence substantially complementary to that of the DNA defined in paragraph (9) is a nucleotide sequence having a homology of not less than about 70% (preferably not less than about 80%, more preferably not less than about 90%, most preferably not less than about 95%) relative to the whole or a part of the nucleotide sequence complementary to that of said DNA;

(47) A pharmaceutical composition which comprises the oligonucleotide or salt defined above in paragraph (45); and

(48) A pharmaceutical composition as defined above in paragraph (47) which is an agent for the treatment or prevention of hormone-producing tumors, acromegaly, giantism, dementia or gastric ulcer, a hormone secretion inhibitor, a tumor growth inhibitor, or a neural activity or sleep modulator.

BRIEF DESCRIPTION OF THE DRAWINGS

FIG. 1 shows the nucleotide sequence of the DNA SEQ ID NO: 107 obtained in Example 2 and coding for the peptide hCS-17 of the present invention and a precursor thereof.

FIG. 2 shows the nucleotide sequence of the DNA SEQ ID NO:108 obtained in, Example 2 and coding for the peptide hCS-17 of the invention and a precursor thereof, and the amino acid sequence SEQ ID NO: 109, deduced therefrom.

FIG. 3 shows the nucleotide sequence of the DNA SEQ ID NO: 110 coding for the peptide hCS-17 of the invention and a precursor thereof, and the amino acid sequence SEQ ID NO: 111 deduced therefrom. In FIG. 2, the codon coding for the 85th amino acid serine in TCC while, in FIG. 3, the corresponding codon is TCT.

In the upper section, the results obtained by using the DNA contained in the plasmid phCSP6 and coding for the peptide hCS-17 of the invention as a probe are shown. In the lower section, the results obtained by using the DNA coding for glyceraldehyde 3-phosphate dehydrogenase (G3PDH) as a probe are shown.

Figure 7:
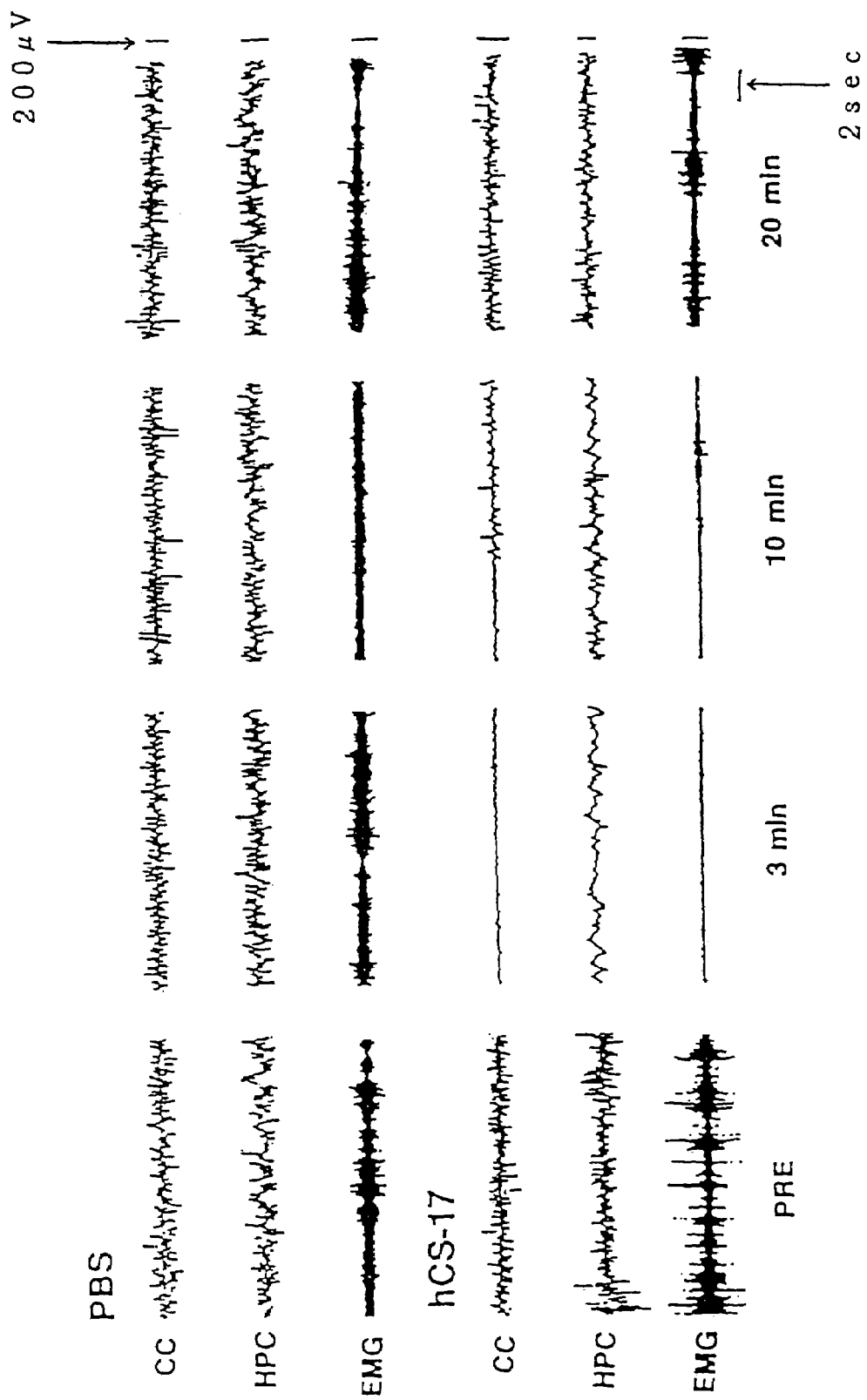

FIG. 7 shows the results of examination of the effect of the peptide hCS-17 of the invention on the rat electroencephalogram. PBS refers to the EEG pattern found after administration of phosphate-buffered physiological saline and hCS-17 refers to the EEG pattern found after administration of 1 nmol of the peptide hCS-17 of the invention to rats. CC refers to the electroencephalogram of cerebral cortex. HIP refers to the electroencephalogram of hippocampus. EMG stands for electromyogram. PRE stands for preadministration, and min stands for minutes.

Figure 8:
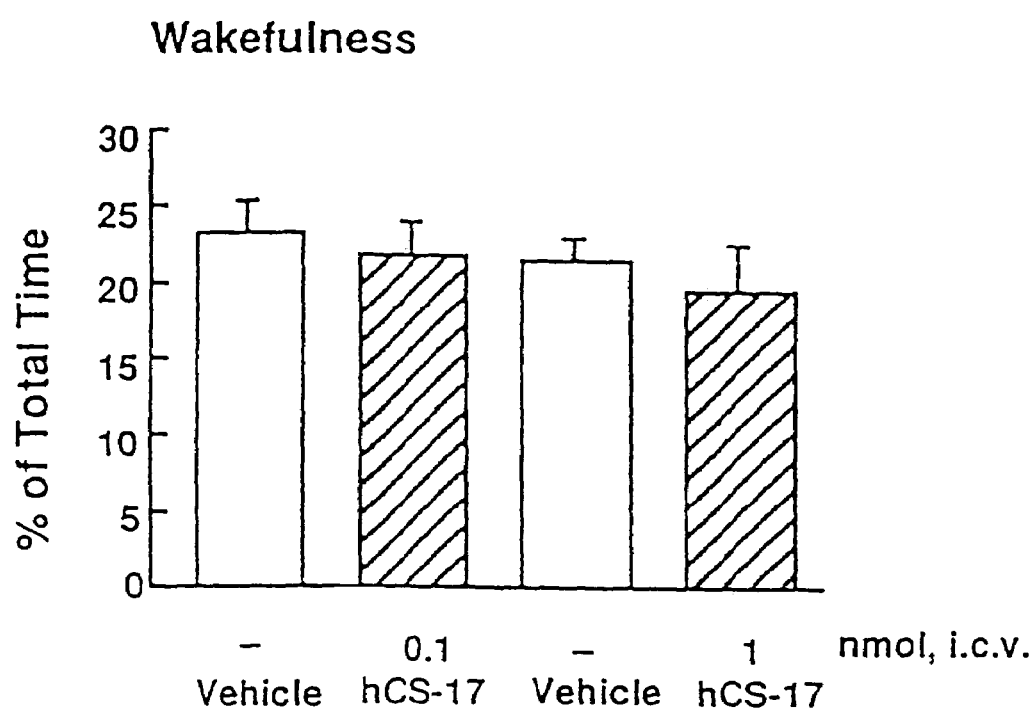

FIG. 8 shows the occupancy time of the wakefulness-indicating EEG pattern during the 4-hour total measurement period following administration of the peptide hCS-17 of the invention in rats. The ordinate represents the percent occupancy time relative to the total measurement time. "Vehicle" on the abscissa-refers to the results obtained by the administration of PBS, "hCS-17" refers to the results obtained by the administration of the mature peptide of the present invention, and the number indicates the administration concentration.

Figure 9:
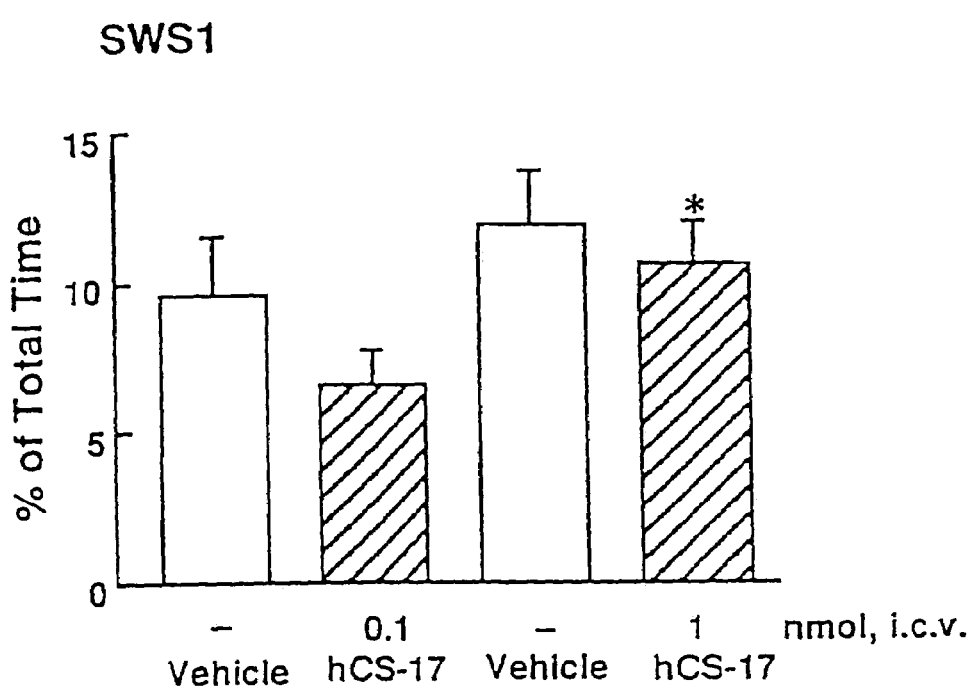

FIG. 9 shows the occupancy time of the shallow- and slow-wave sleep-indicating EEG pattern during the 4-hour total measurement period following administration of the peptide hCS-17 of the invention in rats. The ordinate denotes the percent occupancy time relative to the total measurement time. "Vehicle" on the abscissa refers to the results obtained by the administration of PBS, "hCS-17" refers to the results obtained by the administration of the mature peptide of the present invention, and the number indicates the administration concentration.

Figure 10:
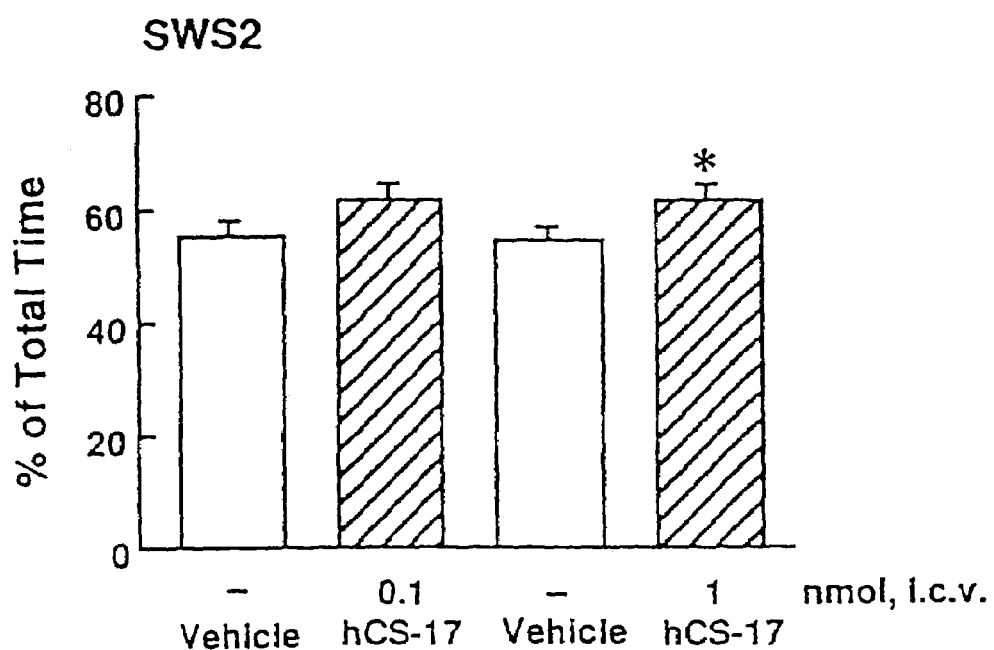

FIG. 10 shows the occupancy time of the deep- and slow-wave sleep-indicating electroencephalogram pattern during the 4-hour total measurement period following administration of the peptide hCS-17 of the invention in rats. The ordinate represents the percent occupancy time relative to the total measurement time. "Vehicle" on the abscissa refers to the results obtained by the administration of PBS, "hCS-17" refers to the results obtained by the administration of the mature peptide of the present invention, and the number indicates the administration concentration.

Figure 11:
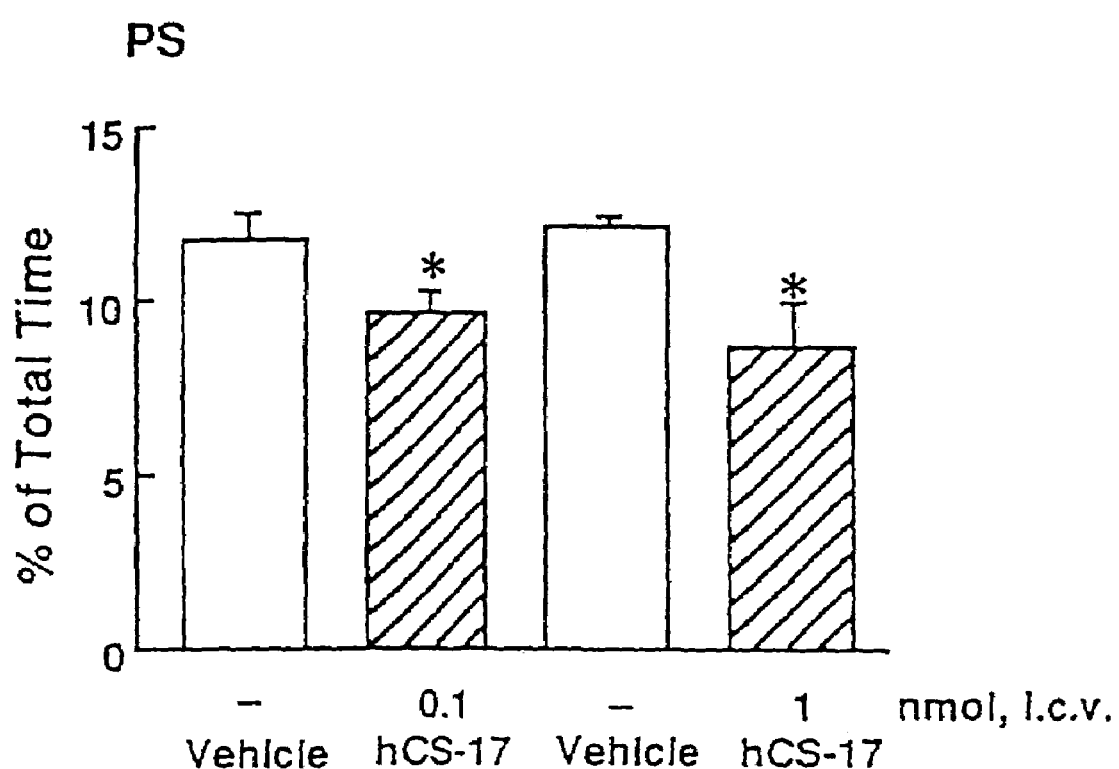

FIG. 11 shows the occupancy time of the paradoxical sleep-indicating electroencephalogram pattern during the 4-hour total measurement period following administration of the peptide hCS-17 of the invention in rats. The ordinate represents the percent occupancy time relative to the total measurement time. "Vehicle" on the abscissa refers to the results obtained by the administration of PBS, "hCS-17" refers to the results obtained by the administration of the mature peptide of the present invention, and the number indicates the administration concentration.

BEST MODE FOR CARRYING OUT THE PRESENT INVENTION

The peptides having an amino acid sequence identical or substantially equivalent thereto identical to the amino acid sequence represented by SEQ ID NO:1 may be any of the peptides derived from various tissues of man and other warm-blooded animals (e.g. guinea pig, rat, mouse, fowl, rabbit, swine, sheep, bovine, monkey, etc.). Among such tissues are cells (e.g. hepatocytes, splenocytes, nerve cells, glia cells, β cells of pancreas, myelocytes, mesangial cells, Langerhans' cells, epidermic cells, epithelial cells, endothelial cells, fibroblasts, fibrocytes, myocites, adipocytes, immune cells (e.g. macrophages, T-cells, B cells, natural killer cells, mastocytes, neutrophils, basophils, eosinophils, monocytes), megarocytes, synovial cells, chondrocytes, osteocytes, osteoblasts, osteoclasts, mammary gland cells, hepatocytes, interstitial cells, the corresponding precursor cells, stem cells, cancer cells, etc.), all tissues in which such cells exist, for example the brain, various parts of the brain (e.g. olefactory bulb, amygdaloid body, basal ganglia, hippocampus, thalamus, hypothalamus, cerebral cortex, medula oblongata, cerebellum), spinal cord, pituitary gland, stomach, pancreas, kidney, liver, gonad, thyroid, gall-bladder, bone marrow, adrenal, skin, muscle, lung, bowels (e.g. large intestine and small intestine), blood vessel, heart, thymus, spleen, submandibular gland, peripheral blood, prostate, testis, ovary, placenta, uterus, bone, joint, skeletal muscle, etc. The peptides mentioned above may also be a synthetic peptides.

Examples of the amino acid sequence which is substantially equivalent to the amino acid sequence represented by SEQ ID NO:1 are an amino acid sequence which is not less than about 90%, preferably not less than about 80%, and most preferably not less than about 95% identity to the amino acid sequence represented by SEQ ID NO:1 and so on.

Examples of the peptide of the present invention which comprises an amino acid sequence substantially equivalent to the amino acid sequence represented by SEQ ID NO:1 is a peptide having an amino acid sequence substantially equivalent to the amino acid sequence represented by SEQ ID NO:1, and having a qualitatively equivalent activity to the peptide having the amino acid sequence represented by SEQ ID NO:1.

The peptides of the present invention may be a mutein of the peptide comprising the amino acid sequence represented by SED ID NO:1 (hereinafter may be described as hCS-17).

The term "qualitatively equivalent activity" is used herein to mean substantial equivalence in qualitative terms such as a cortistatin-like or somatostatin-like activity, mentioned below. Therefore, the degree of equivalence may range, for example, from about 0.1 to about 100 times (preferably about 0.5 to 10, more preferably 0.5 to 2 times). However, differences in quantitative terms such as the potency of activity and the molecular mass of protein are immaterial.

Activities such as a cortistatin-like or somatostatin-like activity may be measured by a per se known method or its analogue method. For example, the activities may be measured by the method described in Japanese Patent Publication (Kokai) no. 116979/1996, or Nature, 381, 16 May 1996, etc.

And, the peptide of the present invention includes the so called muteins, for example, proteins comprising (1) an amino acid sequence wherein a few (1 to 5) amino acid residues are deleted from the amino acid sequence represented by SEQ ID NO:1, (2) an amino acid sequence wherein a few (1 to 5) amino acid residues are substituted with the amino acid sequence represented by SEQ ID NO:1, (3) an amino acid sequence wherein a few (1 to 5) amino acid residues are inserted into the amino acid sequence represented by SEQ ID NO:1, or (4) combinations thereof.

Preferred as the peptide of the present invention are, for example, peptides comprising an amino acid sequence of the formula $X^1$-$X^2$-Asn-Phe-Phe-Trp-Lys-Thr-Phe-$X^3$-Ser-$X^4$ (I)
(SEQ ID NO:115)

wherein $X^1$ represents Asp-Arg-Met-Pro-Cys (SEQ ID NO:116), Arg-Met-Pro-Cys (SEQ ID NO:117), Met-Pro-Cys, Pro-Cys or Cys, $X^2$ represents Arg or Lys, $X^3$ represents Ser or Thr and $X^4$ represents Cys-Lys or Cys (except for the amino acid sequence (SEQ ID NO:118) in which $X^1$ is Pro-Cys, $X^2$ is Lys, $X^3$ is Ser and $X^4$ is Cys-Lys).

As typical examples of the deletion type or/and substitution type mutein which are to be used, the following may be mentioned:

(1) A peptide comprising an amino acid sequence (SEQ ID NO:2) derived from the amino acid sequence defined under SEQ ID NO:1 by deletion of two amino acids (Asp-Arg) from the N terminus thereof (hereinafter sometimes abbreviated as hCS-15);

(2) A peptide comprising an amino acid sequence (SEQ ID NO:3) derived from the amino acid sequence defined under SEQ ID NO:1 by deletion of four amino acids (Asp-Arg-Met-Pro) (SEQ ID NO:117) from the N terminus thereof (hereinafter sometimes abbreviated as hCS-13);

(3) A peptide comprising an amino acid sequence (SEQ ID NO:35) derived from the amino acid sequence defined under SEQ ID NO:1 by deletion of one amino acid (Lys) from the C terminus thereof (hereinafter sometimes abbreviated as des $Lys^{17}$-hCS-17);

(4) A peptide comprising an amino acid sequence (SEQ ID NO:36) derived from the amino acid sequence defined under SEQ ID NO:1 by deletion of two amino acids (Asp-Arg) from the N terminus thereof and one amino acid (Lys) from the C terminus thereof (hereinafter sometimes abbreviated as des $Lys^{15}$-hCS-15);

(5) A peptide comprising an amino acid sequence (SEQ ID NO:37) derived from the amino acid sequence defined under SEQ ID NO:1 by deletion of four amino acids (Asp-Arg-Met-Pro)(SEQ ID NO:117) from the N terminus thereof and one amino acid (Lys) from the C terminus thereof (hereinafter sometimes abbreviated as des $Lys^{13}$-hCS-13);

(6) A peptide comprising an amino acid sequence (SEQ ID NO:38) derived from the amino acid sequence defined under SEQ ID NO:1 by substitution of Lys for the 6th residue Arg (hereinafter sometimes abbreviated as [$Lys^6$]hCS-17);

(7) A peptide comprising an amino acid sequence (SEQ ID NO:39) derived from the amino acid sequence defined under SEQ ID NO:1 by deletion of two amino acids (Asp-Arg) from the N terminus thereof and substitution of Lys for the 4th residue Arg (hereinafter sometimes abbreviated as [$Lys^4$]hCS-15);

(8) A peptide comprising an amino acid sequence (SEQ ID NO:40) derived from the amino acid sequence defined under SEQ ID NO:1 by deletion of four amino acids (Asp-Arg-Met-Pro)(SEQ ID NO:117) from the N terminus thereof and substitution of Lys for the 2nd residue Arg (hereinafter sometimes abbreviated as [$Lys^2$]hCS-13);

(9) A peptide comprising an amino acid sequence (SEQ ID NO:41) derived from the amino acid sequence defined under SEQ ID NO:1 by deletion of one amino acid (Lys) from the C terminus thereof and substitution of Lys for the 6th residue Arg (hereinafter sometimes abbreviated as des $Lys^{17}$-[$Lys^6$]hCS-17);

(10) A peptide comprising an amino acid sequence (SEQ ID NO:42) derived from the amino acid sequence defined under SEQ ID NO:1 by deletion of two amino acids (Asp-Arg) from the N terminus thereof and one amino acid (Lys) from the C terminus thereof and substitution of Lys for the 4th residue Arg (hereinafter sometimes abbreviated as des Lys$^{15}$-[Lys$^4$]hCS-15);

(11) A peptide comprising an amino acid sequence (SEQ ID NO:43) derived from the amino acid sequence defined under SEQ ID NO:1 by deletion of four amino acids (Asp-Arg-Met-Pro)(SEQ ID NO:117) from the N terminus thereof and one amino acid (Lys), from the C terminus thereof and substitution of Lys for the 2nd residue Arg (hereinafter sometimes abbreviated as des Lys$^{13}$-[Lys$^2$] hCS-13);

(12) A peptide comprising an amino acid sequence (SEQ ID NO:44) derived from the amino acid sequence defined under SEQ ID NO:1 by substitution of Thr for the 14th residue Ser (hereinafter sometimes abbreviated as [Thr$^{14}$] hCS-17);

(13) A peptide comprising an amino acid sequence (SEQ ID NO:45) derived from the amino acid sequence defined under SEQ ID NO:1 by deletion of two amino acids (Asp-Arg) from the N terminus thereof and substitution of Thr for the 12th residue Ser (hereinafter sometimes referred to as [Thr$^{12}$]hCS-15);

(14) A peptide comprising an amino acid sequence (SEQ ID NO:46) derived from the amino acid sequence defined under SEQ ID NO:1 by deletion of four amino acids (Asp-Arg-Met-Pro)(SEQ ID NO:117) from the N terminus thereof and substitution of Thr for the 10th residue Ser (hereinafter sometimes referred to as [Thr$^{10}$]hCS-13);

(15) A peptide comprising an amino acid sequence (SEQ ID NO:47) derived from the amino acid sequence defined under SEQ ID NO:1 by deletion of one amino acid (Lys) from the C terminus thereof and substitution of Thr for the 14th residue Ser (hereinafter sometimes referred to as des Lys$^{17}$-[Thr$^{14}$]hCS-1);

(16) A peptide comprising an amino acid sequence (SEQ ID NO:48) derived from the amino acid sequence defined under SEQ ID NO:1 by deletion of two amino acids (Asp-Arg) from the N terminus thereof and one amino acid (Lys) from the C terminus thereof and substitution of Thr for the 12th residue Ser (hereinafter sometimes referred to as des Lys$^{15}$-[Thr$^{12}$]hCS-15);

(17) A peptide comprising an amino acid sequence (SEQ ID NO:49) derived from the amino acid sequence defined under SEQ ID NO:1 by deletion of four amino acids (Asp-Arg-Met-Pro) (SEQ ID NO:117) from the N terminus thereof and the amino acid (Lys) from the C terminus thereof and substitution of Thr for the 10th residue Ser (hereinafter sometimes referred to as des Lys$^{13}$-[Thr$^{10}$] hCS-13);

(18) A peptide comprising an amino acid sequence (SEQ ID NO:50) derived from the amino acid sequence defined under SEQ ID NO:1 by substitution of Lys for the 6th residue Arg and of Thr for the 14th residue Ser (hereinafter sometimes abbreviated as [Lys$^6$,Thr$^{14}$]hCS-17);

(19) A peptide comprising an amino acid sequence (SEQ ID NO:51) derived from the amino acid sequence defined under SEQ ID NO:1 by deletion of two amino acids (Asp-Arg) from the N terminus thereof and substitution of Lys for the 4th residue Arg and of Thr for the 12th residue Ser (hereinafter sometimes abbreviated as [Lys$^4$,Thr$^{12}$] hCS-15);

(20) A peptide comprising an amino acid sequence (SEQ ID NO:52): derived from the amino acid sequence defined under SEQ ID NO:1 by deletion of four amino acids (Asp-Arg-Met-Pro) (SEQ ID NO:117) from the N terminus thereof and, substitution of Lys for the 2nd residue Arg and of Thr for the 10$^{th}$ residue Ser (hereinafter sometimes referred to as [Lys$^2$,Thr$^{10}$]hCS-13);

(21) A peptide comprising an amino acid sequence (SEQ ID NO:53) derived from the amino acid sequence defined under SEQ ID NO:1 by deletion of one amino acid (Lys) from the C terminus thereof and substitution of Lys for the 6th residue Arg and of Thr for the 14th residue Ser (hereinafter sometimes referred to as des Lys$^{17}$-[Lys$^6$, Thr$^{14}$]hCS-17);

(22) A peptide comprising an amino acid sequence (SEQ ID NO:54) derived from the amino acid sequence defined under SEQ ID NO:1 by deletion of two amino acids (Asp-Arg) from the N-terminus thereof and one amino acid (Lys) from the C terminus thereof and substitution of Lys for the 4th residue Arg and of Thr for the 12th residue Ser (hereinafter sometimes referred to as des Lys$^{15}$-[Lys$^4$, Thr$^{12}$]hCS-15);

(23) A peptide comprising an amino acid sequence (SEQ ID NO:55) derived from the amino acid sequence defined under SEQ ID NO:1 by deletion of four amino acids (Asp-Arg-Met-Pro) (SEQ ID NO:117) from the N terminus thereof and one amino acid (Lys) from the C terminus thereof and substitution of Lys for the 2nd residue Arg and of Thr for the 10th residue Ser (hereinafter sometimes referred to as des Lys$^{13}$-[Lys$^2$,Thr$^{10}$]hCS-13); etc.

It is to be noted that the peptide comprising the amino acid sequence defined under SEQ ID NO:31 (known rat-derived cortistatin; r cortistatin in FIG. 3) and the peptide comprising the amino acid sequence defined under SEQ ID NO: 32 (known rat-derived somatostatin; r somatostatin in FIG. 3) are excluded from the range of peptides of the present invention.

When the peptide of the invention has two or more cysteine residues, it is preferred that those cysteine residues form an intramolecular disulfide bond. For instance, the 5th and 16th cysteine residues in the case of hCS-17, the 3rd and 14th cysteine residues in the case of hCS-15, or the 1st and 12th cysteine residues in the case of hCS-13 may form a disulfide bond.

The peptide of the present invention further includes those peptides in which the amino group of the N-terminal amino acid residue is protected by a protective group (e.g. $C_{1-6}$ acyl, such as $C_{1-6}$ alkanoyl, for example formyl, acetyl, etc.), those peptides having a pyroglutamyl group derived from a glutamyl group resulting from in vivo cleavage on the N-terminal side, those peptides in which one or more substituents (e.g. —OH, —SH, amino, imidazole group, indole group, guanidino) on the side chains of the intramolecular amino acids are protected with appropriate protective groups (e.g. $C_{1-6}$ acyl such as $C_{1-6}$ alkanoyl, for example formyl, acetyl; $C_{1-6}$ alkyl such as methyl), complex peptides such as the so-called sugar peptides resulting from binding of a sugar chain, and the like.

The precursor of the present invention may be any peptide or protein provided that it contains the above-mentioned peptide of the present invention. For example, peptides or proteins resulting from addition of one or more (preferably about 2 to 100) amino acid residues to the N terminus or/and C terminus of the peptide of the invention are used. Among these, peptides or proteins resulting from addition of one or more (preferably about 2 to 100) amino acid residues to the N terminus of the peptide of the invention are preferred.

More specifically, those peptides resulting from addition of one or more amino acid residues (counted from the C terminus) of the amino acid sequence (composed of 88 amino acid residues) defined under SEQ ID NO:29 to the N terminus of the peptide having the amino acid sequence defined under SEQ ID NO:1, for example, are each used as the precursor of the present invention.

Thus usable are, for example:

① A precursor peptide comprising the amino acid sequence defined under SEQ ID NO:4 (composed of 29 amino acid residues) (hereinafter sometimes abbreviated as hCS-29);

② A precursor peptide comprising the amino acid sequence defined under SEQ ID NO:5 (composed of 62 amino acid residues) (hereinafter sometimes abbreviated as hCS-62);

③ A precursor peptide comprising the amino acid sequence defined under SEQ ID NO:6 (composed of 85 amino acid residues) (hereinafter sometimes abbreviated as hCS-85);

④ A precursor peptide comprising the amino acid sequence defined under SEQ ID NO:7 (composed of 105 amino acid residues (hereinafter sometimes abbreviated as hCS-105);

⑤ A precursor peptide comprising an amino acid sequence substantially the same as the amino acid sequence defined under SEQ ID NO:4, SEQ ID NO:5, SEQ ID NO:6 or SEQ ID NO:7; and the like.

As examples of the precursor peptide comprising an amino acid sequence substantially the same as the amino acid sequence defined under SEQ ID NO:4, SEQ ID NO 5, SEQ ID NO:6 or SEQ ID NO:7 which are to be used, the following may be mentioned:

(1) A peptide comprising ① an amino acid sequence derived from the amino acid sequence defined under SEQ ID NO: 4 by deletion of about 1 to 10 amino acid residues therefrom, ② an amino acid sequence derived from the amino acid sequence defined under SEQ ID NO:4 by addition of about 1 to 15 amino acid residues thereto, or ③ an amino acid sequence derived from the amino acid sequence defined under SEQ ID NO:4 by substitution of about 1 to 8 amino acid residues occurring therein by other amino acid residues;

(2) A peptide comprising ① an amino acid sequence derived from the amino acid sequence defined under SEQ ID NO: 5 by deletion of about 1 to 15 amino acid residues therefrom, ② an amino acid sequence derived from the amino acid sequence defined under SEQ ID NO:5 by addition of about 1 to 10 amino acid residues thereto, or ③ an amino acid sequence derived from the amino acid sequence defined under SEQ ID NO:5 by substitution of about 1 to 20 amino acid residues occurring therein by other amino acid residues;

(3) A peptide comprising ① an amino acid sequence derived from the amino acid sequence defined under SEQ ID NO:6 by deletion of about 1 to 10 amino acid residues therefrom, ② an amino acid sequence derived from the amino acid sequence defined under SEQ ID NO:6 by addition of about 1 to 10 amino acid residues thereto, or ③ an amino acid sequence derived from the amino acid sequence defined under SEQ ID NO:6 by substitution of about 1 to 20 amino acid residues occurring therein by other amino acid residues;

(4) A peptide comprising ① an amino acid sequence derived from the amino acid sequence defined under SEQ ID NO:7 by deletion of about 1 to 10 amino acid residues therefrom, ② an amino acid sequence derived from the amino acid sequence defined under SEQ ID NO:7 by addition of about 1 to 20 amino acid residues thereto, or ③ an amino acid sequence derived from the amino acid sequence defined under SEQ ID NO:7 by substitution of about 1 to 20 amino acid residues occurring therein by other amino acid residues; and the like.

More specifically, use is made of the following, among others:

① A precursor peptide comprising an amino acid sequence (SEQ ID NO:56) derived from the amino acid sequence defined under SEQ ID NO:4 by substitution of Lys for the 18th residue Arg (hereinafter sometimes abbreviated as [Lys$^{18}$]hCS-29);

② A precursor peptide comprising an amino acid sequence (SEQ ID NO:57) derived from the amino acid sequence defined under SEQ ID NO:4 by substitution of Thr for the 26th residue Ser (hereinafter sometimes abbreviated as [Thr$^{26}$]hCS-29);

③ A precursor peptide comprising an amino acid sequence (SEQ ID NO:58) derived from the amino acid sequence defined under SEQ ID NO:4 by substitution of Lys for the 18th residue Arg and of Thr for the 26th residue Ser (hereinafter sometimes abbreviated as [Lys$^{18}$,Thr$^{26}$]hCS-29);

④ A precursor peptide comprising an amino acid sequence (SEQ ID NO:59) derived from the amino acid sequence defined under SEQ ID NO:59 by substitution of Lys for the 18th residue Arg and deletion of the 29th residue Lys (hereinafter sometimes abbreviated as des Lys$^{29}$-[Lys$^{18}$] hCS-29);

⑤ A precursor peptide comprising an amino acid sequence (SEQ ID NO:60) derived from the amino acid sequence defined under SEQ ID NO:4 by substitution of Thr for the 26th residue Ser and deletion of the 29th residue Lys (hereinafter sometimes abbreviated as des Lys$^{29}$-[Thr$^{26}$] hCS-29);

⑥ A precursor peptide comprising an amino acid sequence (SEQ ID NO:61) derived from the amino acid sequence defined under SEQ ID NO:4 by substitution of Lys for the 18th residue Arg and of Thr for the 26th residue Ser and deletion of the 29th residue Lys (hereinafter sometimes abbreviated as des Lys$^{29}$-[Lys$^{18}$,Thr$^{26}$]hCS-29);

⑦ A precursor peptide comprising an amino acid sequence derived from the amino acid sequence defined under SEQ ID NO:4, SEQ ID NO:5, SEQ ID NO:6 or SEQ ID NO:7 by deletion of the C-terminal Lys (hereinafter sometimes abbreviated as des Lys$^{29}$ hCS-29, des Lys$^{62}$ hCS-62, des Lys$^{85}$ hCS-85 or Lys$^{105}$ hCS-105, respectively); and the like.

When the precursor peptide of the present invention has two or more cysteine residues, it is preferred that those cysteine residues form an intramolecular disulfide bond. For example, in the case of hCS-29, the cysteine residues in positions 17 and 28 may form a disulfide bond.

Like the above-mentioned peptide of the present invention, the precursor peptide of the invention further includes those peptides in which the amino group of the N-terminal amino acid residue is protected by a protective group, those peptides having a pyroglutamyl group derived from a glutamyl group resulting from in vivo cleavage on the N-terminal side, those peptides in which one or more substituents on the side chains of the intramolecular amino acids are protected with appropriate protective groups, and complex peptides such as the so-called sugar peptides resulting from binding of a sugar chain, and the like.

The peptides or precursors of this specification are represented in accordance with the conventions for description of peptides, that is the N-terminus (amino terminus) at left and the C-terminus (carboxyl terminus) at right. The peptide of the present invention including the protein containing the amino acid sequence of SEQ ID NO:1 is usually in the carboxyl (—COOH) or carboxylate (—COO⁻) form at the C-terminus but may be in the amide (—CONH$_2$) or ester (—COOR) form.

R in the ester residue includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl group which is often used for the production of esters for oral administration.

When the peptides or precursor of the present invention has a carboxyl or a carboxylate function in any position other than the C-terminus, the corresponding carboxamide or ester form is also included in the scope of the present invention. The ester mentioned just above may be any of the esters mentioned for the C-terminal carboxyl group.

The salts of the peptide or the precursor of the present invention includes salts with physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc..)

The peptide, the precursor or a salt thereof of the present invention can be produced from the tissues or cells of human or other warm-blooded animals by per se known purification technologies or, as described hereinafter, by culturing a transformant carrying a DNA encoding the protein. It can also be produced in accordance with the procedures for peptide synthesis which are described hereinafter.

When the peptide or the precursor of the present invention is produced from the tissues or cells of human or other warm-blooded animals, the tissues or cells of human or other warm-blood animals are homogenized and the peptide of the present invention is extracted by an acid, etc. The peptide can be isolated and purified from the extracted solution by a combination of chromatography such as reverse phase chromatography, ion exchange chromatography and so on.

For the synthesis of the peptide, the precursor, or their salts, or their amide form of the present invention, any of commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2', 41-dimethoxyphenyl-Fmoc-aminoethyl)phenoxy resin. Using such a resin, amino acids which may be beforehand protected at side-chain functional groups in a suitable manner can be serially condensed with the α-amino group in the order corresponding to the amino acid sequence of the objective protein by various condensation techniques which are per se known. After completion of the final condensation reaction, the protein is separated from the resin and the protective groups are removed. Then, in highly diluted solution, the intramolecular disulfide-forming reaction is carried out to provide the objective proteins or amides thereof.

Referring to the above condensation of protected amino acids, various activating agents known to be useful for protein synthesis can be utilized, and carbodiimide reagents are especially preferred. The carbodiimide reagents include are DCC, N,N'-diisopropylcarbodiimide, and N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or the conjugation thereof to the resin can be properly selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, etc.), sulfoxides (e.g. dimethyl sulfoxide, etc.), ethers (e.g. pyridine, dioxane, tetrahydrofuran, etc.), nitriles (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the condensation thoroughly sufficient. When sufficient condensation can not be achieved by repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxy-benzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower ($C_{1-6}$) alkanoyl group (e.g. acetyl, etc.), an aroyl group (e.g. benzoyl, etc.), a benzyloxycarbonyl, an ethoxycarbonyl group and so on.

The group suitable for etherification includes a benzyl group, a tetrahydropyranyl group, a t-butyl group and so on.

The protective group used for protecting the phenolic hydroxyl group of tyrosine includes Bzl, $C^{12}$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diiso-propylethylamine, triethylamine, piperidine, piperazine or the like, and reduction with sodium metal in liquid ammonia. The above deprotection by treatment with acid is generally conducted at a temperature of about −2° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be properly selected from among the known methods and groups.

An alternative method for providing the peptide or the precursor in amide form typically comprises protecting the α-carboxyl group of the C-terminal amino acid in the form of an amide, extending the peptide chain to a desired length towards the N-terminus, deprotecting the N-terminal α-amino acid of the resulting peptide chain selectively to provide an N-terminal-deprotected fragment, preparing a peptide fragment with its C-terminal carboxyl group selectively deprotected, and condensing the two fragments in a solvent such as the mixed solvent as mentioned above. The condensation reaction can be carried out in the same manner as described hereinbefore. After purification of the protected peptide thus obtained by condensation, all the protective groups are eliminated by the procedures described hereinbefore to provide the contemplated peptide in a crude form. This crude peptide is purified by suitable known purification techniques and lyophilized to provide the desired peptide amide.

A method for providing the peptide or the precursor in an ester form comprises condensing the α-carboxyl group of the C-terminal amino acid with a suitable alcohol to prepare the corresponding ester and subjecting this ester to the same procedure as described for purification of the peptide amide to provide the objective peptide ester.

The peptide, the precursor of the present invention or a salt thereof can be produced by per se known procedures for peptide synthesis. The peptide of the present invention can also be produced by cleaving the precursor of the present invention with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desire peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966
(2) Schroeder and Luebke, The Peptide, Academic Press, New York, 1965
(3) Nobuo Izumiya et al., Fundamentals and Experiments in Peptide Synthesis, Maruzen, 1975
(4) Haruaki Yajima and Shumpei Sakakibara, Biochemical Experiment Series 1, Protein Chemistry IV, 205, 1977
(5) Haruaki Yajima (ed.), Development of Drugs-Continued, 14, Peptide Synthesis, Hirokawa Shoten The peptide having more than two and even number of disulfide-bonds in the molecule can be obtained by ordinary oxidation methods. The oxidation is usually carried out by air-oxidation or iodo-oxidation of the peptide.

After the reaction, the peptide of the present invention can be isolated and purified by a combination of conventional purification techniques such as solvent extraction, distillation, column chromatography, liquid chromatography, and recrystallization. When the peptide isolated as above is in a free form, it can be converted to a suitable salt by known methods or method analogous thereto. On the other hand, when it is isolated as a salt, it can be converted to a free form or to any other salt thereof by known methods or method analogous thereto.

The precursor of the present invention is useful for producing the peptide of the present invention. Moreover, the precursor of the present invention has a substantially the same activity of the peptide of the present invention, that is cortistatin-like or somatostatin-like activity. Therefore, the precursor of the present invention has the same usefulness as of the peptide of the present invention.

Those peptide fragments, inclusive of salts thereof, which are formed on the occasion of production of the mature peptide of the present invention upon cleavage of the precursor of the invention are also physiologically useful peptides. Useful as such peptide fragments are, for example, peptides having the amino acid sequences defined under SEQ ID NO:8, SEQ ID NO:9, SEQ ID NO:10, SEQ ID NO:11 and SEQ ID NO:12, respectively, and the like. As the salts of these peptide fragments, there may be mentioned salts of the same kinds as those mentioned above regarding the salts of the peptide and precursor of the invention.

These peptide fragments and salts can be produced by cleaving the above-mentioned precursor of the invention using an appropriate peptidase, or according to the peptide synthesis technique to be mentioned later herein.

These peptide fragments and salts are also useful, for instance, as antigens for use in the production of antibodies against the precursor of the invention. These peptide fragments and salts are further important in elucidating the mechanisms of in vivo formation of the peptide of the invention. Furthermore, they have a central nervous system or reproductive function modulating effect and are useful as a central nervous system or reproductive function modulator as well.

The DNA coding for the peptide or precursor of the invention may be any DNA provided that it contains the nucleotide sequence coding for the above-mentioned peptide or precursor of the invention. It may be a genomic DNA, a genomic DNA library, a cDNA derived from the above-mentioned cells or tissue, a cDNA library derived from the above-mentioned cells or tissue, or a synthetic DNA. The vector to be used for library construction may be any of bacteriophages, plasmids, cosmids, phagemids and the like. Further, the total RNA or a mRNA fraction prepared from the above-mentioned cells or tissue may be used directly for amplification by the reverse transcriptase polymerase chain reaction (hereinafter abbreviated as RT-PCR) technique.

Specifically, the DNA coding for a peptide having the same or substantially the same amino acid sequence as the amino acid sequence defined under SEQ ID NO:1 of the invention may, for example, be ① a DNA comprising the nucleotide sequence defined under SEQ ID NO:13 or ② any DNA having a nucleotide sequence capable of hybridizing with the nucleotide sequence defined under SEQ ID NO:13 under highly stringent conditions and coding for a peptide having the same activities as those of the peptide having the amino acid sequence defined under SEQ ID NO:1 (e.g. somatostatin-like activity, cortistatin-like activity).

Useful as the DNA capable of hybridizing with the nucleotide sequence defined under SEQ ID NO:13 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:13.

More specifically, useful as the DNA coding for a peptide comprising the amino acid sequence defined under SEQ ID NO:1 is a DNA having the nucleotide sequence defined under SEQ ID NO:13, or the like.

The DNA coding for a deletion type mutein peptide of the present invention which comprises the same or substantially the same amino acid sequence as the amino acid sequence defined under SEQ ID NO:2 is, for example, ① a DNA comprising the nucleotide sequence defined under SEQ ID NO:14 or ② any DNA having a nucleotide sequence capable of hybridizing with the nucleotide sequence defined under SEQ ID NO:14 under highly stringent conditions and coding for a peptide having the same activities as those of the peptide having the amino acid sequence defined under SEQ ID NO:2 (e.g. somatostatin-like activities, cortistatin-like activities).

Useful as the DNA capable of hybridizing the nucleotide sequence defined under SEQ ID NO:14 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:14.

The DNA coding for a deletion type mutein peptide of the present invention comprising the same or substantially the same amino acid sequence as the amino acid sequence defined under SEQ ID NO:3 is, for example, ① a DNA comprising the nucleotide sequence defined under SEQ ID NO:15 or ② any DNA having a nucleotide sequence capable of hybridizing with the nucleotide sequence defined under SEQ ID NO:15 under highly stringent conditions and coding for a peptide having the same activities as those of the peptide having the amino acid sequence defined under SEQ ID NO:3 (e.g. somatostatin-like activity, cortistatin-like activity).

Useful as the DNA capable of hybridizing the nucleotide sequence defined under SEQ ID NO:15 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:15.

Hybridization can be carried out by a per se known method or a modification thereof, for example the method described in Molecular Cloning, 2nd edition, (J. Sambrook et al., Cold Spring Harbor Lab. Press, 1989). When a commercial library is used, it can be carried out following the method described in the use manual attached thereto. More preferably, it can be carried out under highly stringent conditions.

The highly stringent conditions refer, for example, to the following conditions: a sodium concentration of about 19 to 40 mM, preferably about 19 to 20 mM, and a temperature of about 50 to 70° C., preferably about 60 to 65° C. Most preferred is a sodium concentration of about 19 mM and a temperature of about 65° C.

The DNA comprising a nucleotide sequence (e.g. the nucleotide sequence defined under SEQ ID NO:33) coding for rat cortistatin having the amino acid sequence defined under SEQ ID NO:31 and the DNA comprising a nucleotide sequence (e.g. the nucleotide sequence defined under SEQ ID NO:34) coding for rat somatostatin having the amino acid sequence defined under SEQ ID NO:32 are excluded from the range of DNAs coding for the peptide of the present invention.

More specifically, the following are used, among others:

(1) A DNA comprising the nucleotide sequence (SEQ ID NO:14) defined under SEQ ID NO:14 as a DNA coding for a deletion type mutein comprising the amino acid sequence defined under SEQ ID NO:2;

(2) A DNA comprising the nucleotide sequence (SEQ ID NO:15) defined under SEQ ID NO:15 as a DNA coding for a deletion type mutein comprising the amino acid sequence defined under SEQ ID NO:3;

(3) A DNA comprising a nucleotide sequence (SEQ ID NO:62) derived from the nucleotide sequence defined under SEQ ID NO:13 by deletion of 3 nucleotides (AAA) from the 3'-end thereof as a DNA coding for a deletion type mutein comprising the amino acid sequence defined under SEQ ID NO:35;

(4) A DNA comprising a nucleotide sequence (SEQ ID NO:63) derived from the nucleotide sequence defined under SEQ ID NO:14 by deletion of 3 nucleotides (AAA) from the 3'-end thereof as a DNA coding for a deletion type mutein comprising the amino acid sequence defined under SEQ ID NO:36;

(5) A DNA comprising a nucleotide sequence (SEQ ID NO:64) derived from the nucleotide sequence defined under SEQ ID NO:15 by deletion of 3 nucleotides (AAA) from the 3'-end thereof as a DNA coding for a deletion type mutein comprising the amino acid sequence defined under SEQ ID NO:37;

(6) A DNA comprising a nucleotide sequence (SEQ ID NO:65) derived from the nucleotide sequence defined under SEQ ID NO:13 by substitution of AAR (R being G or A) for the 16th to 18th nucleotides AGG as a DNA coding for a substitution type mutein comprising the amino acid sequence defined under SEQ ID NO:38;

(7) A DNA comprising a nucleotide sequence (SEQ ID NO:66) derived from the nucleotide sequence defined under SEQ ID NO:14 by substitution of AAR (R being G or A) for the 10th to 12th nucleotides AGG as a DNA coding for a substitution type mutein comprising the amino acid sequence defined under SEQ ID NO:39;

(8) A DNA comprising a nucleotide sequence (SEQ ID NO:67) derived from the nucleotide sequence defined under SEQ ID NO:15 by substitution of AAR (R being G or A) for the 4th to 6th nucleotides AGG as a DNA coding for a substitution type mutein comprising the amino acid sequence defined under SEQ ID NO:40;

(9) A DNA comprising a nucleotide sequence (SEQ ID NO:68) derived from the nucleotide sequence defined under SEQ ID NO:13 by deletion of 3 nucleotides (AAA) from the 3'-end thereof and substitution of AAR (R being G or A) for the 16th to 18th nucleotides AGG as a DNA coding for a deletion/substitution type mutein comprising the amino acid sequence defined under SEQ ID NO:41;

(10) A DNA comprising a nucleotide sequence (SEQ ID NO:69) derived from the nucleotide sequence defined under SEQ ID NO:14 by deletion of 3 nucleotides (AAA) from the 3'-end thereof and substitution of AAR (R being G or A) for the 10th to 12th nucleotides AGG as a DNA coding for a deletion/substitution type mutein comprising the amino acid sequence defined under SEQ ID NO:42;

(11) A DNA comprising a nucleotide sequence (SEQ ID NO:70) derived from the nucleotide sequence defined under SEQ ID NO:15 by deletion of 3 nucleotides (AAA) from the 3'-end thereof and substitution of AAR (R being G or A) for the 4th to 6th nucleotides AGG as a DNA coding for a deletion/substitution type mutein comprising the amino acid sequence defined under SEQ ID NO:43;

(12) A DNA comprising a nucleotide sequence (SEQ ID NO:71) derived from the nucleotide sequence defined under SEQ ID NO:13 by substitution of ACN (N being A, C, G or T) for the 40th to 42nd nucleotides TCC as a DNA coding for a substitution type mutein comprising the amino acid sequence defined under SEQ ID NO:44;

(13) A DNA comprising a nucleotide sequence (SEQ ID NO:72) derived from the nucleotide sequence defined under SEQ ID NO:14 by substitution of ACN (N being A, C, G or T) for the 34th to 36th nucleotides TCC as a DNA coding for a substitution type mutein comprising the amino acid sequence defined under SEQ ID NO:45;

(14) A DNA comprising a nucleotide sequence (SEQ ID NO:73) derived from the nucleotide sequence defined under SEQ ID NO:15 by substitution of ACN (N being A, C, G or T) for the 28th to 30th nucleotides TCC as a DNA coding for a substitution type mutein comprising the amino acid sequence defined under SEQ ID NO:46;

(15) A DNA comprising a nucleotide sequence (SEQ ID NO:74) derived from the nucleotide sequence defined under SEQ ID NO:13 by deletion of 3 nucleotides (AAA) from the 3%-end thereof and substitution of ACN (N being A, C, G or T) for the 40th to 42nd nucleotides TCC as a DNA coding for a deletion/substitution type mutein comprising the amino acid sequence defined under SEQ ID NO:47;

(16) A DNA comprising a nucleotide sequence (SEQ ID NO:75) derived from the nucleotide sequence defined under SEQ ID NO:14 by deletion of 3 nucleotides (AAA) from the 3'-end thereof and substitution of ACN (N being A, C, G or T) for the 34th to 36th nucleotides TCC as a DNA coding for a deletion/substitution type mutein comprising the amino acid sequence defined under SEQ ID NO:48;

(17) A DNA comprising a nucleotide sequence (SEQ ID NO:76) derived from the nucleotide sequence defined under SEQ ID NO:15 by deletion of 3 nucleotides (AAA) from the 3'-end thereof and substitution of ACN (N being A, C, G or T) for the 28th to 30th nucleotides TCC as a DNA coding for a deletion/substitution type mutein comprising the amino acid sequence defined under SEQ ID NO:49;

(18) A DNA comprising a nucleotide sequence (SEQ ID NO:77) derived from the nucleotide sequence defined under SEQ ID NO:13 by substitution of AAR (R being G or A) for the 16th to 18th nucleotides AGG and of ACN (N being A, C, G or T) for the 40th to 42nd nucleotides TCC as a DNA coding for a substitution type mutein comprising the amino acid sequence defined under SEQ ID NO:50;

(19) A DNA comprising a nucleotide sequence (SEQ ID NO:78) derived from the nucleotide sequence defined under SEQ ID NO:14 by substitution of AAR (R being G or A) for the 10th to 12th nucleotides AGG and of ACN (N being A, C, G or T) for the 34th to 36th nucleotides TCC as a DNA coding for a substitution type mutein comprising the amino acid sequence defined under SEQ ID NO:51;

(20) A DNA comprising a nucleotide sequence (SEQ ID NO:79) derived from the nucleotide sequence defined under SEQ ID NO:15 by substitution of AAR (R being G or A) for the 4th to 6th nucleotides AGG and of ACN (N being A, C, G or T) for the 28th to 30th nucleotides TCC as a DNA coding for a substitution type mutein comprising the amino acid sequence defined under SEQ ID NO:52;

(21) A DNA comprising a nucleotide sequence (SEQ ID NO:80) derived from the nucleotide sequence defined under SEQ ID NO:13 by deletion of 3 nucleotides (AAA) from the 3'-end thereof and substitution of AAR (R being G or A) for the 16th to 18th nucleotides AGG and of ACN (N being A, C, G or T) for the 40th to 42nd nucleotides TCC as a DNA coding for a deletion/substitution type mutein comprising the amino acid sequence defined under SEQ ID NO:53;

(22) A DNA comprising a nucleotide sequence (SEQ ID NO:81) derived from the nucleotide sequence defined under SEQ ID NO:14 by deletion of 3 nucleotides (AAA) from the 3'-end thereof and substitution of AAR (R being G or A) for the 10th to 12th nucleotides AGG and of ACN (N being A, C, G or T) for the 34th to 36th nucleotides TCC as a DNA coding for a deletion/substitution type mutein comprising the amino acid sequence defined under SEQ ID NO:54;

(23) A DNA comprising a nucleotide sequence (SEQ ID NO:82) derived from the nucleotide sequence defined under SEQ ID NO:15 by deletion of 3 nucleotides (AAA) from the 3'-end thereof and substitution of AAR (R being G or A) for the 4th to 6th nucleotides AGG and of ACN (N being A, C, G or T) for the 28th to 30th nucleotides TCC as a DNA coding for a deletion/substitution type mutein comprising the amino acid sequence defined under SEQ ID NO:55; and the like.

The DNA coding for a precursor peptide of the present invention having the same or substantially the same amino acid sequence as the amino acid sequence defined under SEQ ID NO:4 is, for example, ① a DNA comprising the nucleotide sequence defined under SEQ ID NO:16 or SEQ ID NO:17 or ② any DNA comprising a nucleotide sequence capable of hybridizing with the nucleotide sequence defined under SEQ ID NO:16 or SEQ ID NO:17 under highly stringent conditions and coding for the precursor peptide capable of giving the above-mentioned peptide of the present invention.

Useful as the DNA capable of hybridizing with the nucleotide sequence defined under SEQ ID NO:16 or SEQ ID NO:17 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:16 or SEQ ID NO:17.

More specifically, a DNA comprising the nucleotide-sequence defined under SEQ ID NO:16 or SEQ ID NO:17, or the like is used as a DNA coding for a precursor peptide comprising the amino acid sequence defined under SEQ ID NO:4.

The DNA coding for a precursor peptide of the present invention comprising the same or substantially the same amino acid sequence as the amino acid sequence defined under SEQ ID NO:5 is, for example, ① a DNA comprising the nucleotide sequence defined under SEQ ID NO:18 or SEQ ID NO:19 or ② any DNA comprising a nucleotide sequence capable of hybridizing with the nucleotide sequence defined under SEQ ID NO:18 or SEQ ID NO:19 under highly stringent conditions and coding for the precursor peptide capable of giving the above-mentioned peptide of the present invention.

Useful as the DNA capable of hybridizing with the nucleotide sequence defined under SEQ ID NO:18 or SEQ ID NO:19 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:18 or SEQ ID NO:19.

More specifically, a DNA comprising the nucleotide sequence defined under SEQ ID NO:18 or SEQ ID NO:19, or the like is used as a DNA coding for a precursor peptide comprising the amino acid sequence defined under SEQ ID NO:5.

The DNA coding for a precursor peptide of the present invention comprising the same or substantially the same amino acid sequence as the amino acid sequence defined under SEQ ID NO: 6 is, for example, ① a DNA comprising the nucleotide sequence defined under SEQ ID NO:20 or SEQ ID NO:21 or ② any DNA having a nucleotide sequence capable of hybridizing with the nucleotide sequence defined under SEQ ID NO:20 or SEQ ID NO:21 under highly stringent conditions and coding for the precursor peptide capable of giving the above-mentioned peptide of the present invention.

Useful as the DNA capable of hybridizing with the nucleotide sequence defined under SEQ ID NO:20 or SEQ ID NO:21 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:20 or SEQ ID NO:21.

More specifically, a DNA comprising the nucleotide sequence defined under SEQ ID NO:20 or SEQ ID NO:21, or the like is used as a DNA coding for a precursor peptide comprising the amino acid sequence defined under SEQ ID NO:6.

The DNA coding for a precursor peptide of the present invention comprising the same or substantially the same amino acid sequence as the amino acid sequence defined under SEQ ID NO: 7 is, for example, ① a DNA comprising the nucleotide sequence defined under SEQ ID NO:22 or SEQ ID NO:23 or ② any DNA comprising a nucleotide sequence capable of hybridizing with the nucleotide sequence defined under SEQ ID NO:22 or SEQ ID NO:23 under highly stringent conditions and coding for the precursor peptide capable of giving the above-mentioned peptide of the present invention.

Useful as the DNA capable of hybridizing with the nucleotide sequence defined under SEQ ID NO:22 or SEQ ID NO:23 is, for example, a DNA comprising a nucleotide sequence having a homology of not less than about 70%, preferably not less than about 80%, more preferably not less than about 90%, most preferably not less than about 95%, relative to the nucleotide sequence defined under SEQ ID NO:22 or SEQ ID NO:23.

More specifically, a DNA comprising the nucleotide sequence defined under SEQ ID NO:22 or SEQ ID NO:23, or the like is used as a DNA coding for a precursor peptide comprising the amino acid sequence defined under SEQ ID NO:7.

The method of hybridization and highly stringent conditions to be used are the same as those mentioned above.

Furthermore, use is made of the following:

(1) A DNA comprising a nucleotide sequence (SEQ ID NO:83 or SEQ ID NO:84) derived from the nucleotide sequence defined under SEQ ID NO:16 or SEQ ID NO:17 by substitution of AAR (R being G or A) for the 52nd to 54th nucleotides AGG as a DNA coding for a precursor peptide comprising the amino acid sequence defined under SEQ ID NO:56;

(2) A DNA comprising a nucleotide sequence (SEQ ID NO:85 or SEQ ID NO:86) derived from the nucleotide sequence defined under SEQ ID NO:16 or SEQ ID NO:17 by substitution of ACN (N being A, C, G or T) for the 76th to 78th nucleotides TCC as a DNA coding for a precursor peptide having the amino acid sequence defined under SEQ ID NO:57;

(3) A DNA comprising a nucleotide sequence (SEQ ID NO:87 or SEQ. ID NO:88) derived from the nucleotide sequence defined under SEQ ID NO:16 or SEQ ID NO:17 by substitution of AAR (R being G or A) for the 52nd to 54th nucleotides AGG and of ACN (N being A, C, G or T) for the 76th to 78th nucleotides TCC as a DNA coding for a precursor peptide comprising the amino acid sequence defined under SEQ ID NO:58;

(4) A DNA comprising a nucleotide sequence (SEQ ID NO:89 or SEQ ID NO:90) derived from the nucleotide sequence defined under SEQ ID NO:16 or SEQ ID NO:17 by deletion of 3 nucleotides (AAA) from the 3'-end thereof and substitution of AAR (R being G or A) for the 52nd to 54th nucleotides AGG as a DNA coding for a precursor peptide comprising the amino acid sequence defined under SEQ ID NO:59;

(5) A DNA comprising a nucleotide sequence (SEQ ID NO:91 or SEQ ID NO:92) derived from the nucleotide sequence defined under SEQ ID NO:16 or SEQ ID NO:17 by deletion of 3 nucleotides (AAA) from the 3'-end thereof and substitution of ACN (N being A, C, G or T) for the 76th to 78th nucleotides TCC as a DNA coding for a precursor peptide comprising the amino acid sequence defined under SEQ ID NO: 60;

(6) A DNA comprising a nucleotide sequence (SEQ ID NO:93 or SEQ ID NO:94) derived from the nucleotide sequence defined under SEQ ID NO:16 or SEQ ID NO:17 by deletion of 3 nucleotides (AAA) from the 3'-end thereof and substitution of AAR (R being G or A) for the 52nd to 54th nucleotides AGG and of ACN (N being A, C, G or T) for the 76th to 78th nucleotides TCC as a DNA coding for a precursor peptide comprising the amino acid sequence defined under SEQ ID NO:61;

(7) A DNA comprising a nucleotide sequence derived from the nucleotide sequence defined under any of SEQ ID NO:16 through SEQ ID NO:23 by deletion of 3 nucleotides (AAA) from the 3'-end thereof as a DNA coding for a precursor peptide comprising an amino acid sequence derived from the amino acid sequence defined under SEQ ID NO:4, SEQ ID NO:5, SEQ ID NO:6 or SEQ ID NO:7 by deletion of Lys from the C terminus thereof; and the like.

The DNA coding for a peptide fragment formed on the occasion of formation of a mature peptide from the above-mentioned precursor of the present invention may be any DNA provided that it contains a nucleotide sequence coding for the above-mentioned peptide fragment. It may be a genomic DNA, a genomic DNA library, a cDNA derived from the above-mentioned cells or tissue, a cDNA library derived from the above-mentioned cells or tissue, or a synthetic DNA.

For example, a DNA comprising the nucleotide sequence defined under SEQ ID NO:24 or SEQ ID NO:25 may be used as a DNA coding for a peptide fragment comprising the amino acid sequence defined under SEQ ID NO:8; a DNA comprising the nucleotide sequence defined under SEQ ID NO:26, for example, may be used as a DNA coding for a peptide fragment comprising the amino acid sequence defined under SEQ ID NO:9; a DNA comprising the nucleotide sequence defined under SEQ ID NO:27, for instance, may be used as a DNA coding for a peptide fragment comprising the amino acid sequence defined under SEQ ID NO:10; a DNA comprising the nucleotide sequence defined under SEQ ID NO:28, for instance, may be used as a DNA coding for a peptide fragment comprising the amino acid sequence defined under SEQ ID NO:11; and a DNA comprising the nucleotide sequence defined under SEQ ID NO:29 or SEQ ID NO:30, for instance, may be used as a DNA coding for a peptide fragment comprising the amino acid sequence defined under SEQ ID NO:12.

As the means of cloning a DNA coding for the peptide or precursor of the present invention, there may be mentioned, for instance, (1) amplification of the desired DNA from the above-mentioned DNA library by the PCR technique using synthetic DNA primers having a partial nucleotide sequence of a DNA coding for the peptide or precursor of the present invention or (2) selection by hybridization of a DNA inserted into an appropriate vector with a labeled DNA fragment or synthetic DNA coding for a part or the whole region of a peptide or precursor of the present invention.

The method of hybridization is the same as mentioned above. When a commercial library is used, it can be carried out following the method described in the use manual attached thereto.

Modification (deletion, addition, substitution) of DNA nucleotide sequences can be effected by a per se known method such as the gapped duplex method or Kunkel method, or a modification thereof, using a known kit, for example Mutan™-G (Takara Shuzo) or Mutan™-K (Takara Shuzo) or the like.

The thus-cloned DNA coding for a peptide or precursor of the present invention may be used as such or after restriction enzyme digestion or linker addition as desired, as the case may be. Said DNA has ATG as a translation initiation codon at the 5'-end thereof and may have TAA, TGA or TAG as a translation termination codon at the 3'-end thereof. It is also possible to, add these translation initiation codon and translation termination codon using appropriate synthetic DNA adapters.

Expression vectors for the DNA coding for the peptide or precursor of the present invention can be produced, for example, by (a) excising the desired DNA fragment from a DNA coding for the peptide or precursor of the present invention and (b) joining said DNA fragment to an appropriate expression vector downstream of the promoter thereof.

The vector may include plasmids derived from Escherichia coli, e.g., pBR322, pBR325, pUC12, pUC13, etc.; plasmids derived from Bacillus subtilis, e.g., pUB110, pTP5, pC194, etc.; plasmids derived from yeasts e.g., pSH19, pSH15, etc.; bacteriophages such as λ-phage: animal virus such as retrovirus, vaccinia virus, etc.; insect virus; and other vecters such as pA1-11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter include SR α, SV40 promoter, LTR promoter, CMV (cytomegalovirus) promoter, HSV-TK promoter, etc., and CMV promoter and SR α promoter are preferably used.

When the host for the transformation is Escherichia coli, the promoter are preferably trp promoter, lac promoter, recA promoter, λ PL promoter, lpp promoter, T7 promoter, etc.. When the host for the transformation is Bacillus, the promoter are preferably SPO1 promoter, SPO2 promoter, penP promoter, etc.. When the host is a yeast, the promoter are preferably PHO5 promoter, PGK promoter, GAP promoter, ADH promoter, AOX1 promoter, etc. When the host is an insect cell, the promoter include polyhedrin promoter, P10 promoter, etc..

The expression vectors may, if necessary, further comprise enhancers, splicing signals, polyadenylation signals, selective markers, SV40 duplicate origin (hereinafter referred to as SV40 ori). Examples of selective markers are dihydrofolate reductase (hereinafter referred to as dhfr gene, ampicillin resistant gene (hereinafter referred to as $Amp^r$), neomycin-resistant gene (hereinafter referred to as $Neo^r$) and so on. The dhfr gene gives methotrexate (MTX) registant and Neo gives G418 resistant. Particularly, when the dhfr gene is used as a selective marker against dhfr gene-deficient chinese hamster cell line, cells transfected by the objective gene can be selected in a thymidine-free medium.

Furthermore, an appropriate signal sequence for a host can be added to the N-terminal side of the protein. When the host is Escherichia coli, the utilizable signal sequences may include PhoA signal sequence, OmpA signal sequence, etc. When the host is Bacillus, they may include α-amylase signal sequence, subtilisin signal sequence, etc. When the host is a yeast, they may include MF signal sequence, SUC2 signal sequence, etc. When the host is an animal cell, they may include insulin signal sequence, α-interferon signal sequence, antibody molecule signal sequence, etc.

A transformant or transfectant is obtained by using the vector thus constructed, which carries the DNA coding for the peptide of the present invention.

The host may be, for example, Escherichia species, Bacillus species, yeast cells, insect cells, insects, animal cells, etc.

Examples of Escherichia species include Escherichia coli K12.DH1 (Proceedings of the National Academy of Sciences of the United State of America, Vol. 60, 160(1968)), JM103 (Nucleic Acids Research, Vol. 9, 309 (1981)), JA221 (Journal of Molecular Biology, Vol. 120, 517 (1978)), HB101 (Journal of molecular Biology, Vol, 41,459(1969)), C600 [Genetics, Vol. 39, 440 (1954)), etc.

Examples of Bacillus species are, for example, Bacillus subtilis MI114 (Gene, Vol. 24, 255 (1983)), 207–21 (Journal of Biochemistry, Vol. 95, 87 (1984)), etc..

Examples of yeast cells are, for example, Saccharomyces cerevisiae AH22, AH22R⁻, NA87-11A, DKD-5D or 20B-12, Schizosachcaromyces pombe NCYC1913 or Pichia pastoris KM71, etc.

Examples of insect cells are, for example, Spodoptera frugiperda cell (Sf cell), MG1 cell derived from a center intestine of Trichoplusia ni, High Five™ cell derived from eggs of Trichoplusia ni, Mamestra brassicae-derived cell, Estigmena acrea-derived cell and so on when virus is AcNPV; and Bombyx mori N cell (BmN cell) and so on when virus is BmNPV. Examples of the Sf cell are, for example, Sf9 cell (ATCC CRL 1711), Sf21 cell [both, Vaughn J. L. et al., In Vivo, 13, 213–217(1977)] and so on.

Examples of insects include a larva of silkworm (Bombyx mori larva) (Maeda et al., Nature, 315, 592(1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr⁻) cell), mouse L cell, mouse AtT-20, mouse myeloma cell, rat GH3, humanFL, 293 cell, C127 cell, BALB3T3 cell, Sp-2/O cell, etc. Among them, CHO cell, CHO(dhfr⁻) cell, 293 cell, etc. are preferred.

Depending on host cells used, transformation is carried out using standard techniques appropriate to such cells.

Transformation of *Escherichia* species can be carried out in accordance with methods as disclosed in, for example, Proceedings of the National Academy of Sciences of the United State of America, Vol. 69, 2110 (1972), and Gene, Vol. 17, 107 (1982), etc.

Transformation of *Bacillus* species can be carried out in accordance with methods as disclosed in, for example, Molecular & General Genetics, Vol. 168, 111 (1979), etc..

Transformation of yeast cells can be carried out in accordance with methods as disclosed in, for example, Methods in Enzymology, 194, 182–187(1991), etc.

Transformation of insect cells or insects can be carried out in accordance with methods as disclosed in, for example, Bio/Technology, 6, 47–55, (1988).

Transformation of animal cells can be carried out by methods as disclosed in, for example, Cell Engineering, separate vol. 8, New Cell Engineering Experiment Protocol, 263–267(1995) (Shujun Company), Virology, Vol. 52, 456 (1973), etc..

In introducing the expression vector into cells, known methods such as a calcium phosphate method (Graham, F. L. and van der Eb, A. J.: Virology, 52, 456–467(1973)), an electroporation (Neumann, E. et al., EMBO Journal, 1,841–845(1982)), etc. may be used.

In this way, a transformant transformed with the expression vector containing the DNA coding for the peptide or precursor of the present invention is obtained.

Meanwhile, as a method of allowing stable expression of the peptide or precursor of the present invention using animal cells, there may be mentioned the method comprising selecting, by clonal selection, animal cells in which the above expression vector introduced thereinto has been integrated into a chromosome. To be concrete, transformant selection is carried out using the above-mentioned selective marker as an indicator. Further, the animal cells obtained in the above manner using the selective marker are subjected to repeated clonal selection, whereby a stable animal cell line capable of high level expression of the peptide or precursor of the present invention can be obtained. When the dhfr gene is used as the selective marker, it is also possible to obtain a higher expression animal cell line by culturing the cells while gradually raising the MTX concentration and selecting a resistant cell line and thereby intracellularly amplifying the DNA coding for the peptide or precursor of the present invention, together with the dhfr gene.

The peptide or precursor of the present invention, or a salt thereof, can be produced by culturing the transformant mentioned above under conditions enabling expression of the DNA coding for the peptide or precursor of the invention to thereby cause formation and accumulation of the peptide or precursor of the invention.

When a transformant the host of which is a strain of the genus *Escherichia* or *Bacillus* is cultured, a liquid medium is suited as the medium to be used in the cultivation, and carbon sources, nitrogen sources, inorganic and other materials necessary for the growth of said transformant are incorporated in said medium. As the carbon sources, there may be mentioned glucose, dextrin, soluble starch, sucrose and so forth. As the nitrogen sources, there may be mentioned inorganic or organic substances such as ammonium salts, nitric acid salts, corn steep liquor, peptone, casein, meat extract, soybean cake, and potato extract as well as inorganic materials such as calcium chloride, sodium dihydrogen phosphate, magnesium chloride, etc. Yeast extract, vitamins, growth factors and the like may also be added. The pH of the medium is desirably about 5 to 8.

Preferred as the medium for culturing strains of the genus *Escherichia* is, for example, M9 medium containing glucose and casamino acids (Miller, Journal of Experiments in Molecular Genetics, 431–433, Cold Spring Harbor Laboratory, New York, 1972). When necessary, an agent such as 3 β-indolylacrylic acid, for instance, may be added to said medium for efficient promoter functioning. When the host is a strain of the genus *Escherichia*, cultivation is carried out generally at about 15 to 43° C. for about 3 to 24 hours, if necessary with aeration and/or agitation.

When the host is a strain of the genus *Bacillus*, cultivation is carried out generally at about 30 to 40° C. for about 6 to 24 hours, if necessary with aeration and/or agitation.

As the medium for culturing a transformant where the host is a yeast, there may be mentioned, for example, Burkholder's minimum medium [Bostian, K. L. et al., Proc. Natl. Acad. Sci. USA, vol. 77, 4505 (1980)] and SD medium containing 0.5% casamino acids [Bitter, G. A. et al., Proc. Natl. Acad. Sci. USA, vol. 81, 5330 (1984)]. The pH of the medium is preferably adjusted to about 5 to 8. Cultivation is carried out generally at about 20° C. to 35° C. for about 24 to 72 hours, if necessary with aeration and/or agitation.

Useful as the medium for culturing a transformant where the host is an insect cell is Grace's insect medium [Grace, T. C. C., Nature, 195, 788 (1962)] supplemented with such additives as 10% inactivated bovine serum in appropriate quantities. The pH of the medium is preferably adjusted to about 6.2 to 6.4. Cultivation is carried out generally at about 27° C. for about 3 to 5 days, if necessary with aeration and/or agitation.

Useful as the medium for culturing a transformant where the host is an animal cell are, for example, MEM medium containing about 5 to 20% fetal calf serum [Science, vol. 122, 501 (1952)], DMEM medium [Virology, vol. 8, 396 (1959)], RPMI 1640 medium [The Journal of the American Medical Association, vol. 199, 519 (1967)], 199 medium [Proceedings of the Society for the Biological Medicine, vol. 73, 1 (1950)] and the like. The pH is preferably about 6 to 8. Cultivation is carried out generally at about 30° C. to 40° C. for about 15 to 72 hours, if necessary with aeration and/or agitation.

Particularly when CHO (dhfr−) cells are used with the dhfr gene as a selective marker, the use of DMEM medium containing dialyzed fetal calf serum substantially free of thymidine is preferred.

The peptide or precursor of the present invention can be isolated and purified from the culture broth, for example in the following manner.

For extracting the peptide or precursor of the invention from cultured bacterial or other cells, an appropriate method can be used which comprises, for example, collecting bacterial or other cells after cultivation by a known method, suspending them in an appropriate buffer solution and disrupting them by means of supersonic waves, lysozyme and/or freezing-thawing, for instance, followed by centrifugation or filtration to give a crude extract containing the peptide or precursor of the present invention. A protein denaturing agent such as urea or guanidine hydrochloride, and/or a surfactant such as Triton X-100™ may be contained in the buffer solution.

In cases where the peptide or precursor is excreted in the culture liquid phase, bacterial or other cells after completion of cultivation are separated from the supernatant by a per se known method and the supernatant is recovered. The peptide or precursor of the invention contained in the thus-obtained supernatant or extract can be purified by using per se known isolation/purification techniques in a suitable combination. As such known isolation/purification techniques, there may be mentioned techniques utilizing the difference in solubility, such as salting out or solvent precipitation, techniques principally utilizing the difference in molecular weight, such as dialysis, ultrafiltration, gel filtration and SDS-polyacrylamide gel electrophoresis, techniques utilizing the difference in electrostatic charge, such as ion exchange chromatography, techniques utilizing a specific affinity, such as affinity chromatography, techniques utilizing the difference in hydrophobicity, such as reversed-phase liquid chromatography, techniques utilizing the difference in isoelectric point, such as isoelectric focusing, and so on.

In cases where the peptide or the precursor of the present invention thus obtained is in a free form, the free-form peptide can be converted to a salt thereof by known methods or method analogous thereto. In case, where the peptide or the precursor thus obtained is in a salt form vice versa, the peptide salt can be converted to a free form or to any other salt thereof by known methods or method analogous thereto.

The peptide or the precursor of the present invention produced by the transformant can be arbitrarily modified or a polypeptide can be partly removed therefrom, by a suitable protein-modifying enzyme before or after the purification. The protein-modifying enzyme may include trypsin, chymotrypsin, arginyl endopeptidase, protein kinase, glycosidase, etc. The amount of the peptide or the precursor of the present invention thus obtained can be measured by an enzyme immunoassays (enzyme linked immunoassays) using specific antibodies.

The antibodies against the peptide, the precursor of the present invention, or a salt thereof are any antibodies such as polyclonal antibodies and monoclonal antibodies which can recognize the peptide, the precursor of the present invention, or a salt thereof. Among antibodies, the antibody which can neutralize the activity of the peptide, the precursor of the present invention, or a salt thereof is preferred.

The antibodies against the peptide, the precursor of the present invention, or a salt thereof (hereinafter, referred to as the peptide of the present invention) may be manufactured by methods per se known to those of skill in the art or methods similar thereto, using the peptide of the present invention as antigen. For example, monoclonal antibodies and/or polyclonal antibodies can be manufactured by the method as given below.

Preparation of Monoclonal Antibody:

(a) Preparation of Monoclonal Antibody-Producing Cells

The peptide of the present invention is administered to warm-blooded animals either solely or together with carriers or diluents to the site favorable for antibody production. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and fowls. The use of mice and rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from homogeneous or heterogeneous animals to obtain monoclonal antibody-producing hybridomas. Measurement of the antibody titer in antisera may, for example, be carried out by reacting a labeled protein, which will be mentioned later, with the antiserum followed by measuring the binding activity of the labeling agent with the antibody. The cell fusion may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are those derived from warm-blooded animals such as NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10 to 80% followed by incubating at 20 to 40° C., preferably, at 30 to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101; Nissui Seiyaku, Japan). The culture temperature is usually 20 to 40° C. and, preferably, about 37° C. The culture period is usually from five days to three weeks and, preferably, one to two weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of Polyclonal Antibody:

The polyclonal antibody of the present invention can be produced by per se known methods or methods analogous thereto. The method comprises preparing an immunogen (antigen protein) per se or a conjugate of an imunogen with a carrier protein, immunizing a warm-blooded animal in the same manner as described for the production of the monoclonal antibody, harvesting a fraction containing the antibody against the peptide of the present invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of monoclonal antibody described hereinbefore. The separation and purification of the polyclonal antibody can be carried out by the same method as that described for the separation and purification of monoclonal antibody.

The antibody against the before-mentioned parial peptide which is preduced by processing of the precursor, can be produced and used, as mentioned-above. The DNA having a nucleotide sequence complementary or substantially complementary to the DNA coding for the protein, the precursor or the partial peptide of the present invention (hereinafter referred to as the DNA of the present invention) can be any DNA having a nucleotide sequence complementary or substantially complementary to that of the DNA of the present invention and capable of suppressing expression of the DNA.

The nucleotide sequence substantially complementary to the DNA of the present invention may, for example, be a nucleotide sequence having an identity of not less than about 70%, preferably not less than about 80%, more preferably not less than about 90%, and for still better results, not less than about 95% to the total nucleotide sequence or partial nucleotide sequence of the nucleotide sequence complementary to that of the DNA of the present invention. Particularly preferred is an antisense DNA having an identity of not less than about 70%, preferably not less than about 80%, and more preferably not less than about 90%, and for still better results, not less than about 95% to the nucleotide sequence of the domain, of the complete nucleotide sequence complementary to that of the DNA of the present invention, which encodes the N-terminal region of the peptide of the present invention (e.g. the nucleotide sequence of the domain around the initiation codon). The antisense DNA can be synthesized using a known DNA synthesis hardware.

The peptide of the present invention, inclusive of a precursor thereof and a salt of said peptide or precursor, is a peptide-having useful physiological activities such as somatostatin-like and/or cortistatin-like activity. More specifically, it has (i) growth hormone secretion inhibiting activity, (ii) inhibitory activity against secretion of pituitary hormones such as thyroid stimulating hormone and prolactin, (iii) inhibitory activity against secretion of gastrointestinal hormones such as gastrin and insulin, (iv) neurotransmitter activity, (v) cell proliferation stimulating activity, (vi) inhibitory activity against acetylcholine which is a REM sleep inducer, (vii) smooth muscle contraction inhibiting activity, and so forth. Therefore, the peptide, precursor or salt of the invention can be used in various applications.

In the following, several typical uses for the peptide, precursor or salt of the present invention (hereinafter sometimes referred to as the peptide or equivalent of the invention), the DNA coding for the peptide or precursor of the present invention (hereinafter sometimes referred to as the DNA of the invention), the antibody against the peptide, precursor or salt of the present invention (hereinafter sometimes referred to as the antibody of the invention) and the oligonucleotide derivative or a salt thereof are described.

(1) Drugs for the Treatment or Prevention of Various Diseases

As mentioned above, the peptide or equivalent of the invention has (i) growth hormone secretion inhibiting activity, (ii) inhibitory activity against secretion of pituitary hormones such as thyroid stimulating hormone and prolactin, (iii) inhibitory activity against secretion of gastrointestinal hormones such as gastrin and insulin, (iv) neurotransmitter activity, (v) cell proliferation stimulating activity, (vi) inhibitory activity against acetylcholine which is a REM sleep inducer, (vii) smooth muscle contraction inhibiting activity and so on.

Therefore, the peptide or equivalent of the invention is useful as a drug for the treatment or prevention of various diseases resulting from the loss or impairment of cortistatin or somatostatin in vivo, or reduced expression of the DNA coding for cortistatin or somatostatin, among other causes.

Specifically, the peptide or equivalent of the invention is useful as a drug, for example as a therapeutic or prophylactic agent for hormone-producing tumors, acromegaly, giantism, dementia, diabetes, gastric ulcer or the like, a hormone secretion inhibitor, a tumor growth inhibitor, or a neural activity or sleep modulator.

Furthermore, the peptide or equivalent of the invention or the DNA of the invention is useful also as a drug, for example a therapeutic or prophylactic agent for various diseases such as acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, bone fracture, mammary cancer, hyperphagia, polyphagia, burn healing, carcinoma of the uterine cervix, chronic lymphatic leukemia, chronic myelocytic leukemia, chronic pancreatitis, hepatic cirrhosis, colorectal cancer (carcinoma of the colon/rectum), Crohn's disease, dementia, diabetic complications, e.g. diabetic nephropathy, diabetic neuropathy, diabetic retinopathy, etc., gastritis, *Helicobacter pylori* infection, hepatic insufficiency, hepatitis A, hepatitis B, hepatitis C, other types of heptatitis, herpes simplex virus infection, varicella-zoster virus infection, Hodgkin's disease, AIDS virus infection, human papilloma virus infection, hypercalcemia, hypercholesterolemia, hyperglyceridemia, hyperlipemia, infectious diseases, influenza virus infection, insulin-dependent diabetes melitus (type I), invasive staphylococcal infection, malignant melanoma, cancer metastasis, multiple myeloma, allergic rhinitis, nephritis, non-Hodgkin's lymphoma, non-insulin-dependent diabetes melitus (type II), non-small-cell lung cancer, organ transplantation, osteoarthritis, osteomalacia, osteopenia, osteoporosis, ovarian cancer, osteo-Behcet's disease, peptic ulcer, peripheral vascular disease, prostatic cancer, reflux esophagitis, renal failure, rheumatoid arthritis, schizophrenia, sepsis, septic shock, severe systemic fungal infection, small-cell-lung cancer, spinal injury, stomach cancer, systemic lupus erythematosus, transient cerebral ischemic attack, pulmonary tuberculosis, valvular heart disease, vascular/multiple infarction-associated dementia, wound healing, insomnia, arthritis, and neurodegenerative disease, among other diseases. In particular, the peptide or equivalent of the invention or the DNA of the invention is useful as an agent for the treatment or prevention of insomnia.

In the above-mentioned medical application of the peptide or equivalent of the invention, it can be administered orally in such dosage forms as optionally sugar-coated tablets, capsules, elixirs, microcapsules, etc., or parenterally in the form of an injection which includes sterile solutions or suspensions in water or a pharmaceutically acceptable liquid medium other than water. Such dosage forms can be prepared, for example, by admixing the peptide or equivalent of the invention with one or more members of physiologically acceptable carriers, flavoring agents, excipients, vehicles, preservatives, stabilizers, binders and so forth according to the unit formulas generally required for pharmaceutical manufacture. The active ingredient contents of these preparations are such that an appropriate dose can be obtained within an indicated range.

If one wishes to use the peptide, etc. of the present invention, one would use it in a purified form, preferably in a purity of at least 90%, more preferably at least 95%, still more preferably at least 98% and most preferably at least 99%.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical preparation such as by dissolving or suspending active ingredients, naturally occuring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80TM and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. Normally, an appropriate ample is filled in with the thus-prepared pharmaceutical composition such as an injectable liquid.

The thus-obtained preparations are safe and of low toxicity and therefore can be administered, for example, to humans and warm-blooded animals (e.g. rat, mouse, guinea pig, rabbit, chicken, sheep, swine, cattle, horse, cat, dog, monkey, etc.).

The dose of the peptide or equivalent of the invention may vary depending on the disease to be treated, the subject of administration, the route of administration and other factors. Generally, however, a daily dose of about 0.1 to 100 mg, preferably about 1.0 to 50 mg, more preferably about 1.0 to 20 mg, of said peptide or equivalent is administered orally to human adults (whose body weight is assumed to be 60 kg), for the treatment of insomnia, for instance. In the case of parenteral administration, while the amount of the peptide or equivalent of the invention per dose may vary depending on the subject of administration, the disease to be treated and other factors, the peptide or equivalent of the invention may conveniently be administered intravenously in the form of an injection to human adults (whose body weight is assumed to be 60 kg) for the treatment of insomnia, for instance, in a daily dose of about 0.01 to 30 mg, preferably about 0.1 to 20 mg, more preferably about 0.1 to 10 mg. In the case of other animal species, the dose corresponding to the above-mentioned dose for 60 kg body weight can be administered.

The vector with the DNA of the invention inserted therein is also formulated in the same manner as above and generally used parenterally.

(2) Agent for Genetic Diagnosis

An abnormality in the DNA or mRNA coding for the peptide or precursor of the invention (gene abnormality), if any, in human or other warm-blooded animals (e.g. rat, mouse, guinea pig, rabbit, chicken, sheep, swine, cattle, horse, cat, dog, monkey, etc.) can be detected by using the DNA of the invention as a probe. Therefore, said DNA is useful, for example as an agent for the genetic diagnosis of various diseases resulting from an impairment or mutation of the above-mentioned DNA or mRNA or decreased expression thereof or an increased level of said DNA or mRNA or excessive expression thereof.

The above-mentioned genetic diagnosis using the DNA of the invention can be carried out, for example, by the per se known Northern hybridization or PCR-SSCP technique [Genomics, vol. 5, pp. 874–879 (1989); Proceedings of the National Academy of Sciences of the United States of America, vol. 86, pp. 2766–2770 (1989)].

Thus, the DNA of the invention is useful as an agent for genetic diagnosis of, for example, hormone-producing tumors, acromegaly, giantism, dementia, diabetes, gastric ulcer, dwarfism, agalactia or hypogalactia, and the like and, in addition, such diseases as Alzheimer's disease, asthma, arteriosclerosis, atopic dermatitis, hyperphagia, polyphagia, chronic lymphatic leukemia, chronic myelocytic leukemia, Crohn's disease, diabetic complications, Hodgkin's disease, hypercalcemia, hypercholesterolemia, hyperglyceridemia, hyperlipemia, insulin-dependent diabetes melitus (type I), allergic rhinitis, schizophrenia, insomnia, and so forth. In particular, it is useful as an agent for genetic diagnosis of insomnia.

When reduced expression of said mRNA, for instance, is detected by Northern hybridization, the diagnosis may be such that the disease suspected be a hormone-producing tumor, acromegaly, giantism, dementia, diabetes, gastric ulcer, or insomnia, for instance, or the possibility of manifestation of such disease in the future be high.

On the other hand, when excessive expression of said mRNA is detected by Northern hybridization, the diagnosis may be such that the disease suspected is dwarfism, agalactia/hypogalactia, or diabetes, for instance, or that the possibility of manifestation of such disease in the future is high.

Further, when a DNA mutation is detected by the PCR-SSCP technique, the diagnosis may be such that the disease suspected is a hormone-producing tumor, acromegaly, giantism, dementia, diabetes, gastric ulcer, dwarfism, agalctia/hypogalactia or the like or, further, Alzheimer's disease, asthma, arteriosclerosis, atopic dermatitis, hyperphagia, polyphagia, chronic lymphatic leukemia, chronic myelocytic leukemia, Crohn's disease, diabetic complications, Hodgkin's disease, hypercalcemia, hypercholesterolemia, hyperglyceridemia, hyperlipemia, insulin-dependent diabetes melitus (type I), allergic rhinitis, schizophrenia, insomnia or the like, for instance, or that the possibility of manifestation of such disease in the future is high.

(3) Assay of the Peptide, Precursor or Salt of the Invention

The antibody of the invention, which specifically recognizes the peptide or equivalent of the invention, can be used, for example, in assaying the peptide or equivalent of the invention in test solutions, in particular by the sandwich immunoassay technique.

Thus, the present invention provides:

(i) A method of assaying the peptide or equivalent of the invention in a test solution which comprises reacting an antibody against the peptide or equivalent of the invention competitively with the test solution and the peptide or equivalent of the invention which occurs in a labeled form and determining the proportion of the labeled peptide or equivalent of the invention that has been bound to said antibody; and (ii) A method of assaying the peptide or equivalent of the invention in a test solution which comprises reacting the test solution with the antibody of the invention insolubilized on a carrier and another antibody of the invention which occurs in a labeled form either simultaneously or serially and determining the activity of the label on the insolubilizing carrier.

In the assay method mentioned above under (ii), it is desirable that one antibody be an antibody capable of recognizing the N-terminal sequence of the peptide or equivalent of the invention and the other antibody be an antibody capable of reacting with the C-terminal sequence of the peptide or equivalent of the invention.

Further, it is also possible to assay the peptide or equivalent of the invention using a monoclonal antibody against the peptide or equivalent of the invention (hereinafter referred to as monoclonal antibody of the invention) and, in addition, it is also possible to perform the detection by tissue staining, for instance. For achieving these objects, either the antibody molecule itself or a F(ab')$_2$, Fab' or Fab fraction of the antibody molecule may be used.

The method of assaying the peptide or equivalent of the invention using the antibody of the invention is not limited to any particular one but may be any assaying method that comprises detecting, by chemical or physical means, the amount of an antibody, antigen or antibody-antigen complex corresponding to the amount of the antigen (e.g. peptide amount) in a test solution and calculating the amount of said antigen using a standard curve constructed by using standard solutions containing known amounts of the antigen. Thus, for instance, the nephelometric, competitive, immunometric or sandwich technique may suitably be used. From the sensitivity and specificity viewpoint, the sandwich technique to be further mentioned later herein is particularly preferred.

As the label to be used in the assaying method using a labeled substance, there may be mentioned radioisotopes, enzymes, fluorescent substances and luminescent substances, among others. Preferred as the radioisotopes are, for example, [$^{125}$I], [$^{131}$I], [$^{3}$H], [$^{14}$C], etc. As the enzymes, those which are stable and high in specific activity are preferred and there may be mentioned, for example, β-galactosidase, β-glucosidase, alkaline phosphatase, peroxidase, malate dehydrogenase, etc. As the fluorescent substances, there may be mentioned fluorescamine, fluoresceine isothiocyanate, etc. As the luminescent substances, there may be mentioned luminol, luminol derivatives, luciferin, lucigenin, etc. Further, the biotin-avidin system may also be used for antibody- or antigen-label coupling.

In insolubilizing the antigen or antibody, physical adsorption may be utilized, and chemical binding, which is generally used for insolubilization and fixation of peptides, enzymes or the like, may also be used. As the carrier, there may be mentioned insoluble polysaccharides such as agarose, dextran and cellulose, synthetic resins such as polystyrene, polyacrylamide and silicones, or glass and the like.

According to the sandwich technique, the peptide or equivalent of the invention in the test solution can be determined by reacting the test solution with the monoclonal antibody of the invention in an insolubilized form (first reaction) and further with another monoclonal antibody of the invention in a labeled form (second reaction) and measuring the activity of the label on the carrier used for insolubilization. The first and second reactions may be carried out in the reversed order. Further, they may be carried out simultaneously or one after the other. The label and the method of insolubilization may be the same as those mentioned hereinabove. Furthermore, in performing the immunoassay by the sandwich technique, it is not always necessary that only one antibody be used for the solid phase antibody or labeled antibody. A mixture of two or more antibodies may be used for the purpose of improving the sensitivity of measurement, for instance.

In assaying the peptide or equivalent of the invention by the sandwich technique according to the invention, the monoclonal antibody to be used for the first reaction and the monoclonal antibody to be used for the second reaction are preferably antibodies differing in the site of binding to the peptide or equivalent of the invention. Thus, the antibodies to be used in the first and second reactions are such that when the antibody to be used for the second reaction recognizes a C-terminal portion of the peptide or equivalent of the invention, for instance, the antibody to be used for the first reaction should be an antibody recognizing a site other than the C-terminal portion, for example an N-terminal portion.

The monoclonal antibody of the invention can also be used in other measurement systems than the sandwich system, for example in competitive, immunometric or nephelometric systems.

The competitive technique comprises reacting the antigen in test solution and the labeled antigen competitively with the antibody, then separating the unreacted labeled antigen (F) from the labeled antigen (B) bound to the antibody (B/F separation), determining the amount of the label either on B or on F and thus assaying the antigen in the test solution. For this reaction mode, the liquid phase method using a soluble antibody as the antibody, polyethylene glycol for B/F separation, and a second antibody with respect to said antibody, among others, or the solid phase method using an insolubilized antibody as the first antibody or using a soluble first antibody, and an immobilized second antibody may be employed.

According to the immunometric technique, the antigen in test solution and an immobilized antigen are competitively reacted with a predetermined amount of a labeled antibody and then the solid and liquid phases are separated from each other, or the antigen in test solution is reacted with an excessive amount of a labeled antibody, then an insolubilized antigen is added for causing the unreacted labeled antibody to be bound to the solid phase and, thereafter, the solid and liquid phases are separated from each other. Then, the amount of the label in either phase is determined and the amount of the antigen in test solution is calculated.

Further, in nephelometry, the amount of an insoluble precipitate resulting from the antigen-antibody reaction in a gel or solution is determined. Even when the amount of the antigen in test solution is small and gives the precipitate only in a minute amount, laser nephelometry, which utilizes scattering of laser beams, can be used with advantage.

In applying these respective immunological assay techniques to the assaying method of the invention, no particular conditions or operations are required. A system of assaying the peptide or equivalent of the invention may be constructed giving ordinary technical considerations, which are evident to those skilled in the art, to those conditions and procedures which are ordinary in the respective techniques. For details of these general technical means, reference may be made to several reviews, monographs and so on.

For instance, Hiroshi Irie (ed.): "Radioimmunoassay" (published by Kodansha, 1974); Hiroshi Irie (ed.): "Radioimmunoassay, A Sequel" (published by Kodansha, 1979); Eiji Ishikawa et al. (ed.): "Koso Men-eki Sokuteiho (Enzyme Immunoassay)" (published by Igaku Shoin, 1978); Eiji Ishikawa et al. (ed.): "Koso Men-eki Sokuteiho", 2nd ed. (published by Igaku Shoin, 1982); Eiji Ishikawa et al. (ed.): "Koso Men-eki Sokuteiho", 3rd ed. (published by Igaku Shoin, 1987); Methods in Enzymology, vol. 70 (Immunochemical Techniques (Part A)), ibid., vol. 73 (Immunochemical Techniques (Part B)), ibid., vol. 74 (Immunochemical Techniques (Part C)), ibid., vol. 84 (Immunochemical Techniques (Part D: Selected Immunoassays)), ibid., vol. 92 (Immunochemical Techniques (Part E: Monoclonal Antibodies and General Immunoassay Methods)), ibid., vol. 121 (Immunochemical Techniques (Part I: Hybridoma Technology and Monoclonal Antibodies)) (published by Academic Press) and so on may be referred to.

In the above manner, the peptide or equivalent of the invention can be assayed with good sensitivity by using the antibody of the invention.

Furthermore, various diseases in which the peptide or equivalent of the invention is involved can be diagnosed by determining the concentration of the peptide or equivalent of the invention using the antibody of the invention.

More specifically, when a reduced concentration of the peptide or equivalent of the invention is detected, the diagnosis may be such that the disease suspected is a hormone-producing tumor, acromegaly, giantism, dementia, diabetes, gastric ulcer, or insomnia, for instance, or that the possibility of manifestation of such disease in the future is high.

When, on the other hand, an increased concentration of the peptide or equivalent of the invention is detected, the diaganosis may be such that the disease suspected is dwarfism, agalactia/hypogalactia, or diabetes, for instance, or that the possibility of manifestation of such disease in the future is high.

In addition, when an abnormal concentration of the peptide of the invention is detected, the diagnosis may be such that the disease suspected is acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, bone fracture, mammary cancer, hyperphagia, polyphagia, burn healing, carcinoma of the uterine cervix, chronic lymphatic leukemia, chronic myelocytic leukemia, chronic pancreatitis, hepatic cirrhosis, colorectal cancer (carcinoma of the colon/rectum), Crohn's disease, diabetic complications, e.g. diabetic nephropathy, diabetic neuropathy, diabetic retinopathy, etc., gastritis, *Helicobacter pylori* infection, hepatic insufficiency, hepatitis A, hepatitis B, hepatitis C, other types of hepatitis, herpes simplex virus infection, varicella-zoster virus infection, Hodgkin's disease, AIDS virus infection, human papilloma virus infection, hypercalcemia, hypercholesterolemia, hyperglyceridemia, hyperlipemia, miscellaneous infectious diseases, influenza virus infection, insulin-dependent diabetes melitus (type I), invasive staphylococcal infection, malignant melanoma, cancer metastasis, multiple myeloma, allergic rhinitis, nephritis, non-Hodgkin's lymphoma, noninsulin-dependent diabetes melitus (type II), non-small-cell lung cancer, organ transplantation, osteoarthritis, osteomalacia, osteopenia, osteoporosis, ovarian cancer, osteo-Behcet's disease, peptic ulcer, peripheral vascular disease, prostatic cancer, reflux esophagitis, renal failure, rheumatoid arthritis, schizophrenia, sepsis, septic shock, severe systemic fungal infection, small-cell lung cancer, spinal injury, stomach cancer, systemic lupus erythematosus, transient cerebral ischemic attack, pulmonary tuberculosis, valvular heart disease, vascular/multiple infarction-associated dementia, wound healing, arthritis, and neurodegenerative disease, among other diseases, or that the possibility of manifestation of such disease in the future is high.

The antibody of the invention can also be used for detecting the peptide or equivalent of the invention occurring in specimens derived from body fluids or tissues. Further, it can be used for preparing antibody columns for the purification of the peptide or equivalent of the invention, detecting the peptide or equivalent of the invention in each fraction during the process of purification, or analyzing the behavior of the peptide or equivalent of the invention in test cells, for instance.

(4) Screening for Candidate Medicinal Compounds

The peptide or equivalent of the invention is specifically conjugated with somatostatin receptors, receptors for the peptide or equivalent of the invention, and those receptors, such as GPR7 and GPR8, to which the peptide or equivalent of the invention may be conjugated (hereinafter collectively referred to as "receptor(s)" for short) and, therefore, by constructing a ligand-receptor binding assay system using the peptide or equivalent of the invention and said receptor, it is possible to carry out screening for candidate medicinal compounds having somatostatin-like or cortistatin-like activity, or screening for candidate medicinal compounds capable of stimulating or inhibiting the activity of the peptide or equivalent of the invention or of somatostatin or cortistatin. Thus, the present invention provides a method of screening for a compound, or a salt thereof, which is capable of modifying the binding of the peptide or equivalent of the invention to said receptor or receptors which comprises using the peptide or equivalent of the invention.

More specifically, the present invention provides:

(I) A method of screening for a compound, or a salt thereof, which is capable of modifying the binding of the peptide or equivalent of the invention to the receptor, which comprises, on the one hand, (i) bringing the peptide or equivalent of the invention into contact with said receptor, a fragment peptide derived therefrom, or a salt of said receptor or fragment peptide and, on the other hand, (ii) bringing the peptide or equivalent of the invention and a compound to be tested into contact with said receptor, fragment peptide or salt, and making a comparison between the above cases (i) and (ii); and (II) A method of screening for a compound, or a salt thereof, which is capable of modifying the binding of the peptide or equivalent of the invention to the receptor, which comprises, on the one hand, (i) bringing the peptide or equivalent of the invention into contact with cells or a cell membrane fraction, which contain or contains said receptor and, on the other hand, (ii) bringing the peptide or equivalent of the invention and a compound to be tested into contact with the cells or cell membrane fraction containing said receptor, and making a comparison between the above cases (i) and (ii).

More specifically, the screening method of the invention is characterized in that the levels of binding of the peptide or equivalent of the invention to said receptor or receptor-containing cells, or the cell stimulating activities, for instance, are determined or measured in the cases (i) and (ii) and compared therebetween.

The compound capable of modifying the binding of the peptide or equivalent of the invention to the receptors includes ① compounds binding to the receptors and showing cell stimulating activity (the so-called receptor agonists), ② compounds binding to the receptors and inhibiting the cell stimulating activity of agonists (the so-called receptor antagonists), ③ compounds increasing the binding of the peptide or equivalent of the invention to the receptors, and ④ compounds decreasing the binding of the peptide or equivalent of the invention to the receptors, among others.

More specifically, the present invention provides:

(Ia) A method of screening for a compound, or a salt thereof, which is capable of modifying the binding of a peptide or equivalent of the invention to the receptor, which comprises, on the one hand, (i) bringing the peptide or equivalent of the invention in a labeled form into contact with said receptor, a fragment peptide derived therefrom or a salt of said receptor or fragment peptide and, on the other hand, (ii) bringing the labeled peptide or equivalent of the invention and a compound to be tested into contact with said receptor, fragment peptide or salt, and determining and comparing the levels of binding of the labeled peptide or equivalent of the invention to said receptor, fragment peptide or salt in and between the above cases (i) and (ii);

(IIa) A method of screening for a compound, or a salt thereof, which is capable of modifying the binding of the peptide or equivalent of the invention to the receptor, which comprises, on the one hand, (i) bringing the peptide or equivalent of the invention in a labeled form into contact with cells or a cell membrane fraction, which contain or contains said receptor and, on the other hand, (ii) bringing the labeled peptide or equivalent of the invention and a compound to be tested into contact with said receptor-containing cells or cell membrane fraction, and determining and comparing the levels of binding of the labeled peptide or equivalent to said cells or cell membrane fraction in and between the above cases (i) and (ii):

(IIb) A method of screening for a receptor agonist which comprises bringing the peptide or equivalent of the invention into contact with cells containing the receptor and determining and comparing the thus-obtained data on cell stimulating activities mediated by said receptor (e.g. arachidonic acid release, acetylcholine release, intracellular $Ca^{2+}$ concentration change, intracellular cAMP formation, intracellular cGMP formation, inositol phosphate production, cell membrane potential change, intracellular protein phosphorylation, c-fos activation, pH decrease, cell migration activity promoting or inhibiting activity, etc., in particular intracellular cAMP formation promoting or inhibiting activity); and (IIc) A method of screening for a receptor antagonist which comprises, on the one hand, (i) bringing the peptide or equivalent of the invention into contact with cells containing the receptor and, on the other hand, (ii) brining the peptide or equivalent of the invention and a compound to be tested into contact with the receptor-containing cells, and determining and comparing the thus-obtained data on cell stimulating activities mediated by said receptor (e.g. arachidonic acid release, acetylcholine release, intracellular $Ca^{2+}$ concentration change, intracellular cAMP formation, intracellular cGMP formation, inositol phosphate production, cell membrane potential change, intracellular protein phosphorylation, c-fos activation, pH decrease, cell migration activity promoting or inhibiting activity, etc., in particular intracellular cAMP formation promoting or inhibiting activity) in and between the above cases (i) and (ii).

In the above-mentioned screening method (Ia) or (IIa), compounds capable of binding to the receptor and modifying (or inhibiting) the binding of the peptide or equivalent of the invention to the receptor can be selected as receptor agonists or receptor antagonists.

In the above-mentioned screening method (Ia) or (IIa), compounds incapable of binding to the receptor but capable of increasing the binding of the peptide or equivalent of the invention to the receptor can be selected as compounds capable of increasing the binding of the peptide or equivalent of the invention to the receptor.

In the above-mentioned screening method (Ia) or (IIa), compounds incapable of binding to the receptor but decreasing the binding of the peptide or equivalent of the invention to the receptor can be selected as compounds capable of decreasing the binding of the peptide or equivalent of the invention to the receptor.

In the above-mentioned screening method (IIb), compounds capable of binding to the receptor and inhibiting the receptor-mediated cell stimulating activity (e.g. arachidonic acid release, acetylcholine release, intracellular $Ca^{2+}$ concentration change, intracellular cAMP formation; intracellular cGMP formation, inositol phosphate production, cell membrane potential change, intracellular protein phosphorylation, c-fos activation, pH decrease, cell migration activity promoting or inhibiting activity, etc.), in particular inhibiting intracellular cAMP formation can be selected as receptor agonists.

In the above-mentioned screening method (IIc), compounds capable of binding to the receptor and inhibiting the cell stimulating activity of the peptide or equivalent of the invention can be selected as receptor antagonists.

In particular, in the screening method of the invention it is desirable to carry out the above-mentioned screening (Ia) or (IIa) and select compounds capable of inhibiting the binding of the peptide or equivalent of the invention to the receptor, then subjecting the thus-obtained compounds to the above-mentioned screening (IIb) or (IIc) and select, on the one hand, compounds having the above-mentioned cell stimulating activity as receptor agonists and, on the other hand, compounds capable of inhibiting the cell stimulating activity of the peptide or equivalent of the invention as receptor antagonists.

Among the receptors to be used in the screening method of the invention, the somatostatin receptor includes, among others, somatostatin receptor subtype 1 (SSTR1) or subtype 2 (SSTR2) (Yamada et al., Proc. Natl. Acad. Sci., USA, vol. 89, pp. 251–255, 1992), subtype 3 (SSTR3) (Yamada et al., Molecular Endocrinology, vol. 6, pp. 2136–2142, 1992), subtype 4 (SSTR4) or subtype 5 (SSTR5) (Yamada et al., Biochem. Biophys, Res. Commun., vol. 195, pp. 844–852, 1993), etc. As GPR7 or GPR8, those described in Genomics, 28, 84–91 (1995) can be used. The receptor for the peptide or equivalent of the invention can be obtained by per se known techniques for protein purification and it is also possible to obtain the desired receptor by cloning a DNA coding for said receptor by ter se known genetic engineering techniques and then causing the expression of said DNA according to the above-mentioned method of causing expression of the peptide or equivalent of the invention.

Usable as the receptor-derived fragment peptide are fragment peptides obtained by appropriate cleavage of the full-length peptide.

Usable as the receptor-containing cells are such cells as those mentioned above as the host cells for use in the expression of the peptide or equivalent of the invention. Among them, CHO cells or the like are preferred, however. The receptor-containing cells can be produced by using a DNA coding for the receptor and according to per se known techniques, for example the above-mentioned method for the expression of the peptide of the invention. The DNA coding for the receptor can be obtained by per se known genetic engineering techniques, and somatostatin receptor subtypes 1 to 5 and GPR7 or GPR 8, for instance, can be obtained according to the references cited above.

When said receptor-containing cells are used in the screening method of the invention said cells may be fixed with glutaraldehyde, formalin or the like. The fixation can be carried out according to ner se known techniques. Further, brain, hypophysis, lung and other tissues derived from various animals and membrane fractions thereof may be used as the receptor-containing cells.

The labeled peptide or equivalent of the invention is, for example, the peptide or equivalent of the invention labeled with [$^3$H], [125I], [$^{14}$C] or [$^{35}$S], or the like.

As the test compound, there may be mentioned peptides, proteins, non-peptide compounds, synthetic compounds, fermentation products, cell extracts, plant extracts, animal tissue extracts and so forth. These compounds may be novel ones or known ones.

Specifically, in carrying out the above-mentioned screening method (Ia) or (IIa), receptor standards are first prepared by suspending cells or a cell fraction, which contain or contains the receptor of the invention or the receptor or a fragment peptide thereof in a buffer suited for screening. The buffer may be any buffer that will not inhibit the binding of the peptide or equivalent of the invention to the receptor, for example phosphate buffer, Tris-hydrochloride buffer or the like, which has a pH of about 4 to 10 (desirably about 6 to 8). For reducing non-specific binding, a surfactant, such as CHAPS, Tween-80™ (Kao-Atlas), digitonin or deoxycholate, may also be added to the buffer. For inhibiting receptor or ligand decomposition by proteases, a protease inhibitor, such as PMSF, leupeptin, bacitracin, aprotinin, E-64 (product of Peptide Institute) or pepstatin, may further be added. When, on the other hand, the cells are fixed or immobilized ones, the binding of the peptide or equivalent of the invention to the receptor may be effected by using the cells in a state immobilized on incubation vessels, namely in the form of cells as grown, or cells fixed with glutaraldehyde or paraformaldehyde.

In this case, a culture medium or Hank's solution, among others, is used as said buffer. And a predetermined amount (e.g. about 10,000 cpm to 1,000,000 cpm in the case of 2,000 Ci/mmol) of the peptide or equivalent of the invention in a labeled form (e.g. [$^{125}$I]-labeled peptide or equivalent of the invention) is added to 0.01 ml to 10 ml of the receptor solution and, at the same time, $10^{-4}$ M to $10^{-10}$ M of the test compound is caused to coexist. To ascertain the non-specific binding (NSB), reaction tubes with a large excess of the peptide or equivalent of the invention added in an unlabeled form are also prepared. The reaction is carried out at about 0° C. to 50° C. desirably about 4° C. to 37° C., for about 20 minutes to 24 hours, desirably about 30 minutes to 3 hours. After the reaction, each reaction mixture is filtered through a glass fiber filter or the like and, after washing with an appropriate amount of the same buffer, the radioactivity (e.g. radioactivity of [$^{125}$I]) remaining on the glass fiber filter is measured using a liquid scintillation counter or γ-counter. For the filtration, a manifold or cell harvester may be used; the use of a cell harvester is desirable for improving the efficiency, however. When the count ($B_0$) in the absence of any antagonizing substance minus the non-specific binding (NSB), namely the count ($B_0$–NSB), is taken as 100%, a test compound showing a specific binding (B–NSB) which is not more than 50%, for instance, of the count ($B_0$–NSB) can be selected as a candidate agonist or antagonist.

In carrying out the above-mentioned screening method (IIb) or (IIc), the receptor-mediated cell stimulating activity (e.g. arachidonic acid release, acetylcholine release, intracellular $Ca^{2+}$ concentration change, intracellular cAMP formation, intracellular cGMP formation, inositol phosphate production, cell membrane potential change, intracellular protein phosphorylation, c-fos activation, pH decrease, cell migration activity promoting or inhibiting activity, etc.) can be measured using a known method or a commercial assay kit. Specifically, cells containing the receptor are first cultured on multiwell plates or the like. Prior to carrying out the screening, the medium is exchanged for a fresh medium or an approrpiate buffer showing no cytotoxicity. The test compound etc. are then added and, after a predetermined incubation period, the cells are extracted or the supernatant is recovered, and the product or products formed are assayed by the respective methods. If the detection of formation of a substance (e.g. arachidonic acid) selected as the indicator of cell stimulating activity is confounded by a decomposing enzyme present in the cells, the assay may be carried out in the presence of an inhibitor of said decomposing enzyme. As regards cAMP production inhibiting activity or the like, the activity can be detected in terms of the inhibitory activity against cells in which the basal production has been augmented with forskolin or the like.

The screening kit of the invention comprises the peptide or equivalent, preferably together with cells or a cell membrane fraction which contain or contains the receptor or the receptor or a fragment peptide thereof.

As examples of the screening kit of the invention, there may be mentioned the following:

[REAGENTS for Screening]

① Measurement Buffer and Washing Buffer

Hank's balanced salt solution (Gibco) supplemented with 0.05% bovine serum albumin (Sigma).

This is sterilized by filtration through a filter with a pore size of 0.45 μm and stored at 40° C. It may be prepared extemporaneously.

② Somatostatin Receptor Standard

Somatostatin receptor-containing CHO cells subcultured on 12-well plates at $5 \times 10^5$ cells/well and cultured under the conditions of 37° C. and 5% $CO_2$ plus 95% air for 2 days.

③ Labeled Peptide or Equivalent of the Invention

The peptide or equivalent of the invention as labeled with commercially available [$^3$H], [125I], [$^{14}$C], [$^{35}$S] or the like (e.g. [$^{125}$I]hCS-17).

It is stored in a solution state at 4° C. or −20° C. and extemporaneously diluted to 1 μM with measurement buffer.

④ Standard Solution of the Peptide or Equivalent of the Invention

The peptide or equivalent of the invention is dissolved in PBS containing 0.1% bovine serum albumin (Sigma) to 0.1 mM and stored at −20° C.

[Method of Measurement]

① Recombinant somatostatin receptor-containing CHO cells cultured on 12-well tissue culture plates are washed with two 1-ml portions of measurement buffer, and 490 μl of measurement buffer is added to each well.

② 5 μl of a 10-3 to 10-10 M solution of the test compound is added, then 5 μl of a 5 nM solution of the peptide or equivalent of the invention in a labeled form is added, and the reaction is allowed to proceed at room temperature for 1 hour. To ascertain the non-specific binding, 5 μl of a $10^{-4}$ M solution of the peptide or equivalent of the invention is added in lieu of the test compound.

③ The reaction solution is removed, and each well is washed with three 1-ml portions of washing buffer. The cell-bound labeled peptide or equivalent of the invention is dissolved using 0.5 ml of 0.2 N NaOH-1% SDS and the solution is mixed with 4 ml of a liquid scintillator A (Wako Pure Chemical Industries).

④ The radioactivity is measured using a liquid scintillation counter (Beckman) and expressed in terms of percent maximum binding (PMB) according to the formula [Mathematical Formula 1] shown below. When the label is [$^{125}$I], the radioactivity can be measured directly using a gamma counter without admixing with the liquid scitillator.

[Mathematical Formula 1]

$$PBM=[(B-NSB)/(B0-NSB)] \times 100$$

where PMB: percent maximum binding;
B: value when the test compound is added;
NSB: non-specific binding;
$B_0$: maximum binding.

As mentioned above, the peptide or equivalent of the invention is useful as a reagent for screening for a compound capable of modifying the binding of the peptide or equivalent of the invention to the receptor.

The compound, inclusive of salts thereof, obtained by using the screening method or screening kit of the invention is a compound capable of modifying the binding of the peptide or equivalent of the invention to the receptor and, more particularly, ① a compound capable of binding to the receptor to inhibit stimulation of cells by agonists (the so-called receptor agonist). ② a compound capable of binding to the receptor and inhibiting a cell stimulating activity (the so-called receptor antagonist), ③ a compound capable of increasing the binding of the peptide or equivalent of the invention to the receptor or ④ a compound capable of diminishing the binding of the peptide or equivalent of the invention to the receptor.

The receptor agonist has all or some of the physiological activities of the peptide or equivalent of the invention or somatostatin, hence is useful as a drug, which is safe and low in toxicity, depending on its physiological activities. For instance, it is useful as an inhibitor of the secretion of such hormones as growth hormone, pituitary hormones (e.g. thyroid stimulating hormone, prolactin, etc.) gastrointestinal hormones (e.g. gastrin, insulin, etc.), etc. Furthermore, it is useful as a therapeutic or prophylactic agent for hormone-producing tumors, acromegaly, gigantism, dementia, diabetes, gastric ulcer and other diseases, or as a hormone secretion inhibitor, a tumor growth inhibitor, a neural activity or sleep modulator, or the like.

On the other hand, the receptor antagonist inhibits all or some of the physiological activities of the peptide or equivalent of the invention or somatostatin, hence is useful as a safe and low-toxicity drug for inhibiting such physiological activities. For instance, it is useful as an promoter of the secretion of such hormones as growth hormone, pituitary hormones (e.g. thyroid stimulating hormone, prolactin, etc.), gastrointestinal hormones (e.g. gastrin, insulin, etc.) or the like. It is further useful as a therapeutic or prophylactic agent for dwarfism, agalactia/hypogalactia, diabetes, etc., or a modulator of the functions of digestion-related organs (e.g. function modulator for such organs as stomach, small intestine, pancreas, liver, etc.).

The compound capable of increasing the binding of the peptide or equivalent of the invention to the receptor enhances the physiological activities of the peptide or equivalent of the invention or somatostatin, hence is useful as a drug of the same nature as the above-mentioned receptor agonist.

The compound capable of diminishing the binding of the peptide or equivalent of the invention to the receptor suppresses the physiological activities of the peptide or equivalent of the invention or somatostatin, hence is useful as a drug of the same nature as the above-mentioned receptor antagonist.

In using it as the above-mentioned therapeutic or prophylactic agent, the compound obtained by using the screening method or screening kit of the invention can be used in a conventional manner. For instance, it can be made up into pharmaceutical preparations or dosage forms, such as tablets, capsules, elixirs, microcapsules, sterile solutions or suspensions, in the same manner as in the case of the above-mentioned drug composition containing the peptide or equivalent of the invention, and can be administered to human or warm-blooded animals.

The thus-obtained preparations are safe and low in toxicity, hence can be administered to human or warm-blooded animals (e.g. mouse, rat, rabbit, sheep, swine, cattle, horse, chicken, cat, dog, monkey, chimpanzee, etc.), for instance.

The dose of said compound may vary depending on the disease to be treated, the subject of administration, the route of administration and other factors. Generally, however, where the receptor agonist is orally administered for the treatment of insomnia, for instance, said receptor agonist is administered in a daily dose of about 0.1 mg to 100 mg, preferably about 1.0 to 50 mg, more preferably about 1.0 to 20 mg per adult human (assuming that the body weight is 60 kg). For nonoral administration, the unit dose of said receptor agonist also may vary depending on the subject of administration, the disease to be treated and other factors but, in the case of administration of said receptor agonist in the form of an injection to an average adult (weighing 60 kg) for the treatment of insomnia, for instance, it is advisable that said receptor agonist be administered by intravenous injection in a daily dose of about 0.01 to 30 mg, preferably about 0.1 to 20 mg, more preferably about 0.1 to 10 mg. In the case of other animals, a dose corresponding to the above-mentioned 60 kg-base dose can be administered.

On the other hand, for oral administration of the receptor antagonist for the treatment of dwarfism, said receptor antagonist is generally administered to human adults (weighing 60 kg) in a daily dose of about 0.1 mg to 100 mg, preferably about 1.0 to 50 mg, more preferably about 1.0 to 20 mg. In the case of nonoral administration, the unit dose of said receptor antagonist also may vary depending on the subject of administration, the disease to be treated and other factors. In parenteral administration, in the form of an injection, to an ordinary adult (weighing 60 kg) for the treatment of dwarfism, it is advisable that said receptor antagonist be administered by intravenous injection in a daily dose of about 0.01 to 30 mg, preferably about 0.1 to 20 mg, more preferably about 0.1 to 10 mg. In other animals, too, a dose corresponding to the above-mentioned 60 kg-base dose can be administered.

(5) Pharmaceutical Composition Containing the Oligonucleotide Derivative or a Salt Thereof The oligonucleotide derivative or a salt thereof may be classified into an oligonucleotide derivative or a salt thereof which is capable of binding to the DNA of the invention and thereby promoting the expression of the DNA or peptide or equivalent of the invention (hereinafter referred to briefly as oligonucleotide derivative A) or an oligonucleotide or a salt thereof which is capable of binding to the DNA of the invention and thereby inhibiting the expression of the DNA or peptide or equivalent of the invention (antisense DNA; hereinafter referred to briefly as oligonucleotide B).

As mentioned hereinbefore, the peptide or equivalent of the invention has (i) growth hormone secretion inhibiting activity, (ii) inhibitory activity against secretion of pituitary hormones such as thyroid stimulating hormone and prolactin, (iii) inhibitory activity against secretion of gastrointestinal hormones such as gastrin and insulin, (iv) neurotransmitter activity, (v) cell proliferation stimulating activity, (vi) inhibitory activity against activities of acetylcholine, which is a REM sleep inducer, and (vii) smooth muscle contraction inhibiting activity, among others.

Therefore, the oligonucleotide derivative A promotes the functions of the peptide or equivalent of the invention, which produces the above activities in vivo, or the functions of the DNA coding for the same, hence it is useful, for example, as an inhibitor of the secretion of certain hormones such as growth hormone, pituitary hormones (e.g. thyroid stimulating hormone, prolactin, etc.) and gastrointestinal hormones (e.g. gastrin, insulin, etc.). It can further be used as a therapeutic or prophylactic agent for hormone-producing tumors, acromegaly, gigantism, dementia, diabetes, gastric ulcer, etc., a hormone secretion inhibitor, a tumor proliferation inhibitor, a neural activity or sleep modulator, or a like drug.

On the other hand, the oligonucleotide derivative B (antisense DNA) inhibits the functions of the peptide or equivalent of the invention, which produces the above-mentioned activities in vivo, or of the DNA coding for the same, hence is useful, for example, as a promoter of the secretion of growth hormone, pituitary hormones (e.g. thyroid stimulating-hormone, prolactin, etc.), gastrointestinal hormones (e.g. gastrin, insulin, etc.) and so forth. It can further be used as a therapeutic or prophylactic agent for dwarfism, agalactia/hypogalactia, diabetes or the like, or a function modulator for digestion-related organs (e.g. a functional modulator of the stomach, small intesine, pancreas, liver, etc.) or a like drug.

For use as the above-mentioned drug, said oligonucleotide derivative or a salt thereof can be made up into pharmaceutical preparations in the same manner as the above-mentioned pharmaceutical composition containing the DNA of the invention, and can be administered to human or warm-blooded animals. For instance, said oligonucleotide derivative or a salt thereof can be administered to human or warm-blooded animals in the conventional manner either as it is or after insertion into an appropriate vector, such as a retrovirus vector, adenovirus vector or adenovirus-associated virus vector. Said oligonucleotide derivative or a salt thereof can be administered either as it is or in the form of pharmaceutical preparations containing the same together with a physiologically acceptable carrier such as an intake-promoting auxiliary, by means of a gene gun or a catheter, e.g. a hydrogel catheter.

(6) Pharmaceutical Composition Containing the Antibody of the Invention

The antibody of the invention, which is capable of neutralizing the activities of the peptide or equivalent of the invention, inhibits all or some of the physiological activities of the peptide or equivalent of the invention or of somatostatin or cortistatin, hence can be used as a drug, for example a promoter of the secretion of hormones such as growth hormone, pituitary hormones (e.g. thyroid stimulating hormone, prolactin, etc.) and gastrointestinal hormones (e.g. gastrin, insulin, etc.) and, further, as a therapeutic or prophylactic agent for dwarfism, agalactia/hypogalactia, diabetes and so on, as a function modulator for digestion-related organs (e.g. a functional modulator of the stomach, small intestine, pancreas, liver, etc.) or a like drug.

The therapeutic or prophylactic agent for the diseases mentioned above which contains the antibody of the invention can be administered orally or nonorally to human or mammals (e.g. rat, rabbit, sheep, swine, cattle, cat, dog, monkey, etc.) in the form of solutions or appropriate dosage form compositions. The dose may vary depending on the subject of administration, the disease to be treated, the symptoms or condition, the route of administration, and other factors. Generally, however, it is advisable that, in using it for the treatment or prevention of dwarfism in adults, for instance, said antibody be administered by intravenous injection in a single dose of about 0.01 to 20 mg/kg body weight, preferably about 0.1 to 10 mg/kg body weight, more preferably about 0.1 to 5 mg/kg body weight, about one to five times a day, preferably about one to three times a day. In other nonoral administration cases and in oral administration-cases, corresponding doses can be administered. In particularly severe cases, the dose may be increased according to the severity of illness.

Said antibody can be administered either as it is or in the form of a pharmaceutical composition. The pharmaceutical composition for the above-mentioned administration comprises said antibody or a salt thereof and a pharmacologically acceptable carrier, diluent or excipient. Such composition is provided as a dosage form suited for oral or nonoral administration.

Thus, for example, the composition for oral administration includes solid or liquid dosage forms, specifically tablets (inclusive of sugar-coated tablets and film-coated tablets), pills, granules, powders, capsules (inclusive of soft capsules), syrups, emulsions, suspensions, etc. Such compositions are produced by per se known techniques and contain carriers, diluents or excipients generally employed in the field of pharmacy. For example, lactose, starch, sucrose, magnesium stearate and so forth are used as carriers or excipients for tablets.

The composition for nonoral administration is, for example, an injection, suppository or the like. The injection includes such dosage forms as injections for intravenous, subcutaneous, intradermal or intramuscular administration or for drip injection, among others. Such injections are prepared according to per se known techniques, for example by dissolving, suspending or emulsifying the above-mentioned antibody or a salt thereof in a sterile aqueous or oleaginous liquid commonly used in injections. Usable as the aqueous medium for injections are, for example, physiological saline, and isotonic solutions containing glucose and other auxiliaries, among others. Appropriate dissolution promoters, such as alcohols (e.g. ethanol), polyhydric alcohols (e.g. propylene glycol, polyethylene glycol), nonionic surfactants [e.g. polysorbate 80. HCO-50 (polyoxyethylene (50 mol) adduct of hydrogenated castor oil)], etc., may be used combinedly. Usable as the oleaginous medium are, for example, sesame oil, soybean oil and the like, and benzyl benzoate, benzyl alcohol or the like may be used combinedly as a dissolution promoter. The injections prepared are generally filled into appropriate ampules. The suppository for rectal administration is prepared by admixing the above-mentioned antibody or a salt thereof with an ordinary suppository base.

The above-mentioned pharmaceutical composition for oral or nonoral administration is conveniently prepared in the form of unit dosage forms suited for the administration of the active ingredient. As examples of such unit dosage forms, there may be mentioned tablets, pills, capsules, injections (ampules) and suppositories. Generally, each unit dosage form preferably contains 5 to 500 mg, in particular 5 to 10 mg in the case of injections and 10 to 250 mg in the case of other dosage forms, of the above-mentioned antibody.

Each composition mentioned above may contain another or other active ingredients unless they show undesirable interactions when formulated with the above-mentioned antibody.

(7) Production of Nonhuman Animals Containing the DNA of the Invention

Nonhuman transgenic animals capable of expression of the peptide or equivalent of the invention can be produced using the DNA of the invention. As the nonhuman animals, there may be mentioned mammals (e.g. rat, mouse, rabbit, sheep, swine, cattle, cat, dog, monkey, etc.) and others (hereinafter referred to as animals for short). In particular, mice, rats, rabbits and the like are preferred.

For transferring the DNA of the invention to the target animal, it is generally advantageous to use said DNA as a gene construct obtained by joining the same to the downstream of a promoter capable of causing expression of said DNA in animal cells. In the case of transfer of a rabbit-derived DNA of the invention, a gene construct resulting from joining thereof to the downstream of one of various animal-derived promoters having high homology thereto and capable of causing expression of the DNA of the invention in animal cells is introduced, for example, into fertilized rabbit ova by microinjection, whereby transgenic animals carrying said DNA and producing the peptide or equivalent of the invention at high levels can be produced. Ubiquitous expression promoters such as virus-derived promoters and metallothionein promoters, for instance, can also be used as said promoter.

The transfer of the DNA of the invention in the stage of fertilized ovum cells is secured in a manner such that said DNA occurs in all embryo cells and somatic cells of the target animal. The occurrence of the peptide or equivalent of the invention in embryo cells of the animal produced after DNA transfer means that all offspring of the animal produced have the peptide or equivalent of the invention in all embryo cells and somatic cells thereof. Offsprings of this kind of animal that has inherited the gene have the peptide or equivalent of the invention in all embryo cells and somatic cells thereof.

The transgenic animals carrying the DNA of the invention, after confirmation of their stably maintaining the gene after mating, can be bred as animals carrying said DNA by passage under ordinary feeding conditions. Furthermore, homozygous animals having the introduced gene in both of homologous chromosomes can be obtained by mating male and female animals each carrying the desired DNA and, by mating these male and female homozygous animals, it is possible to effect propagation thereof by passage in a manner such that all offspring may carry said DNA.

The animals with the DNA of the invention transferred thereto, which show high expression of the peptide or equivalent of the invention, are useful as animals for screening for therapeutic or prophylactic agents for diseases caused by excessive expression of the peptide or equivalent of the invention, for instance.

The transgenic animals carrying the DNA of the invention can be used also as a source of cells for tissue culture. For instance, analyses concerning the peptide or equivalent of the invention can be performed by directly analyzing the DNA or RNA in tissues of the transgenic animals (e.g. mice) carrying the DNA of the invention or by analyzing the tissues in which the peptide of the invention expressed by the gene is present. By culturing cells of a tissue containing the peptide or equivalent of the invention by standard tissue culture techniques, it is possible to study the functions of cells derived from tissues generally difficult to culture, such as those derived from brain or peripheral tissues. By using said cells, it is also possible to select drugs capable of increasing the functions of various tissues. Further, it is possible to isolate and purify the peptide or equivalent of the invention if there is a high expression cell line.

In the present specification and drawings, the nucleotides and amino acids, when indicated by abbreviations, are indicated by the abbreviations according to the IUPAC-IUB Commission on Biochemical Nomenclature or the abbreviations conventionally used in the relevant field of art. Examples are shown below. Where optical isomers are possible with regard to amino acids, it is the L form that is meant, unless otherwise indicated.

DNA: deoxyribonucleic acid
cDNA: complementary deoxyribonucleic acid
A: adenine
T: thymine
G: guanine C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
dNTPs: mixture of dATP, dTTP, dGTP and dCTP
ATP: adenosine triphosphate
EDTA: ethylenediaminetetraacetic acid
SDS: sodium dodecyl sulfate
EIA: enzyme immunoassay
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid The substituents, protective groups and reagents frequently appearing in the present specification are shown below in terms of abbreviations.
Me: methyl group
Et: ethyl group.
Bu: butyl group
Ph: phenyl group
TC: thiazolidine-4(R)-carboxamide group
BHA: benzhydrylamine
pMBHA: p-methylbenzhydrylamine
Tos: p-toluenesulfonyl
CHO: formyl
cHex: cyclohexyl
OcHex: cyclohexyl ester
Bzl: benzyl
Bom: benzyloxymethyl
Z: benzyloxycarbonyl
Br-Z: 2-bromobenzyloxycarbonyl
Boc: t-butyloxycarbonyl
DNP: dinitrophenyl
Trt: trityl
Bum: t-butoxymethyl
DCM: dichloromethane
Fmoc: N-9-fluorenylmethoxycarbonyl
HOBt: 1-hydroxybenzotriazole
HOOBt: 3,4-dihydro-3-hydroxy-4-oxo-1,2,3-benzotriazole
DCC: N,N'-dicyclohexylcarbodiimide
TFA: trifluoroacetic acid
DIEA: diisopropylethylamine
PAM: phenylacetamidomethyl
MeBzl: 4-methylbenzyl
Cl-Z: 2-chlorobenzyloxycarbonyl
DCC: N,N'-dicyclohexylcarbodiimide
DMF: N,N-dimethylformamide
NMP: N-methyl-2-pyrrolidone
EDTA: ethylenediaminetetraacetic acid
SDS: sodium dodecyl sulfate In the present specification, the sequence identifier numbers in the sequence listing respectively refer to the following.

[SEQ ID NO:1]

The amino acid sequence of a mature peptide of the invention (from the 89th residue to the 105th residue in the amino acid sequence shown in FIG. 2; hCS-17).

[SEQ ID NO:2]

The amino acid sequence of a peptide derived from the mature peptide defined under SEQ ID NO:1 by deletion of two amino acids (Asp-Arg) from the N terminus thereof (from the 91st residue to the 105th residue in the amino acid sequence shown in FIG. 2; hCS-15).

[SEQ ID NO: 3]

The amino acid sequence of a peptide derived from the mature peptide defined under SEQ ID NO:1 by deletion of four amino acids (Asp-Arg-Met-Pro)(SEQ ID NO:117) from the N terminus thereof (from the 93rd residue to the 105th residue in the amino acid sequence shown in FIG. 2; hCS-13).

[SEQ ID NO:4]

The amino acid sequence of a precursor of the invention (from the 77th residue to the 105th residue in the amino acid sequence shown in FIG. 2; hCS-29).

[SEQ ID NO:5]

The amino acid sequence of a precursor of the invention (from the 44th residue to the 105th residue in the amino acid sequence shown in FIG. 2; hCS-62).

[SEQ ID NO:6]

The amino acid sequence of a precursor of the invention (from the 21st residue to the 105th residue in the amino acid sequence shown in FIG. 2; hCS-85).

[SEQ ID NO:7]

The amino acid sequence of a precursor of the invention (from the 1st residue to the 105th residue in the amino acid sequence shown in FIG. 2; hCS-105).

[SEQ ID NO:8]

The amino acid sequence of a fragment peptide (from the 77th residue to the 88th residue in the amino acid sequence shown in FIG. 2).

[SEQ ID NO:9]

The amino acid sequence of a fragment peptide (from the 44th residue to the 76th residue in the amino acid sequence shown in FIG. 2).

[SEQ ID NO:10]

The amino acid sequence of a fragment peptide (from the 21st residue to the 43rd residue in the amino acid sequence shown in FIG. 2).

[SEQ ID NO:11]

The amino acid sequence of a fragment-peptide (from the 1st residue to the 20th residue in the amino acid sequence shown in FIG. 2).

[SEQ ID NO:12]

The amino acid sequence of a fragment peptide (from the 1st residue to the 88th residue in the amino acid sequence shown in FIG. 2).

[SEQ ID NO:13]
A nucleotide sequence coding for the amino acid sequence defined under SEQ ID NO:1 (from the 268th to the 318th nucleotide in the nucleotide sequence shown it FIG. 2).

[SEQ ID NO:14]
A nucleotide sequence coding for the amino acid sequence defined under SEQ ID NO:2 (from the 274th to the 318th nucleotide in the nucleotide sequence shown in FIG. 2).

[SEQ ID NO:15]
A nucleotide sequence coding for the amino acid sequence defined under SEQ ID NO:3 (from the 280th to the 318th nucleotide in the nucleotide sequence shown in FIG. 2).

[SEQ ID NO:16]
A nucleotide sequence coding for the amino acid sequence defined under SEQ ID NO:4 (from the 232nd to the 318th nucleotide in the nucleotide sequence shown in FIG. 2).

[SEQ ID NO:17]
A nucleotide sequence coding for the amino acid-sequence defined under SEQ ID NO:4 (from the 229th to the 315th nucleotide in the nucleotide sequence shown in FIG. 3).

[SEQ ID NO:18]
A nucleotide sequence coding for the amino acid sequence defined under SEQ ID NO:5 (from the 133rd to the 318th nucleotide in the nucleotide sequence shown in FIG. 2).

[SEQ ID NO:19]
A nucleotide sequence coding for the amino acid sequence defined under SEQ ID NO:5 (from the 130th to the 315th nucleotide in the nucleotide sequence shown in FIG. 3).

[SEQ ID NO:20]
A nucleotide sequence coding for the amino acid sequence defined under SEQ ID NO:6 (from the 64th to the 318th nucleotide in the nucleotide sequence shown in FIG. 2).

[SEQ ID NO:21]
A nucleotide sequence coding for the amino acid sequence defined under SEQ ID NO:6 (from the 61st to the 315th nucleotide in the nucleotide sequence shown in FIG. 3).

[SEQ ID NO:22]
A nucleotide sequence coding for the amino acid sequence defined under SEQ ID NO:7 (from the 4th to the 318th nucleotide in the nucleotide sequence shown in FIG. 2).

[SEQ ID NO:23]
A nucleotide sequence coding for the amino acid sequence defined under SEQ ID NO:7 (from the 1st to the 315th nucleotide in the nucleotide sequence shown in FIG. 3).

[SEQ ID NO:24]
A nucleotide sequence coding for the amino acid sequence defined under SEQ ID NO:8 (from the 232nd to the 267th nucleotide in the nucleotide sequence shown in FIG. 2).

[SEQ ID NO:25]
A nucleotide sequence coding for the amino acid sequence defined under SEQ ID NO:8 (from the 229th to the 264th nucleotide in the nucleotide sequence shown in FIG. 3).

[SEQ ID NO:26]
A nucleotide sequence coding for the amino acid sequence defined under SEQ ID NO:9 (from the 133rd to the 231st nucleotide in the nucleotide sequence shown in FIG. 2).

[SEQ ID NO:27]
A nucleotide sequence coding for the amino acid sequence defined under SEQ ID NO:10 (from the 64th to the 132nd nucleotide in the nucleotide sequence shown in FIG. 2).

[SEQ ID NO:28]
A nucleotide sequence coding for the amino acid sequence defined under SEQ ID NO:11 (from the 4th to the 63rd nucleotide in the nucleotide sequence shown in FIG. 2).

[SEQ ID NO:29]
A nucleotide sequence coding for the amino acid sequence defined under SEQ ID NO:12 (from the 4th to the 267th nucleotide in the nucleotide sequence shown in FIG. 2).

[SEQ ID NO:30]
A nucleotide sequence coding for the amino acid sequence defined under SEQ ID NO:12 (from the 1st to the 264th nucleotide in the nucleotide sequence shown in FIG. 3).

[SEQ ID NO:31]
The amino acid sequence of known rat-derived cortistatin.

[SEQ ID NO:32]
The amino acid sequence of known rat-derived somatostatin.

[SEQ ID NO:33]
A nucleotide sequence coding for the amino acid sequence of known rat-derived cortistatin as defined under SEQ ID NO:31.

[SEQ ID NO:34]
A nucleotide sequence coding for the amino acid sequence of known rat-derived somatostatin as defined under SEQ ID NO:32.

[SEQ ID NO:35]
The amino acid sequence (16 amino acid residues) of a deletion type peptide.

[SEQ ID NO:36]
The amino acid sequence (14 amino acid residues) of a deletion type peptide.

[SEQ ID NO:37]
The amino acid sequence (12 amino acid residues) of a deletion type peptide.

[SEQ ID NO:35]
The amino acid sequence of a peptide derived from the peptide having the amino acid sequence defined under SEQ ID NO:1 by deletion of one amino acid (Lys) from the C terminus thereof (des Lys$^{17}$ hCS-17).

[SEQ ID NO:36]
The amino acid sequence of a peptide derived from the peptide having the amino acid sequence defined under SEQ ID NO:1 by deletion of two amino acids (Asp-Arg) from the N terminus thereof and of one amino acid (Lys) from the C terminus thereof (des Lys[15] hCS-15).

[SEQ ID NO:37]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and of one amino acid (Lys) from the C terminus thereof (des Lys[13] hCS-13).

[SEQ ID NO:38]
The amino acid sequence of a peptide derived from the peptide having the amino acid sequence defined under SEQ ID NO:1 by substitution of Lys for the 6th residue Arg ([Lys[6]]hCS-17).

[SEQ ID NO:39]
The amino acid sequence of a peptide derived from the peptide having the amino acid sequence defined under SEQ ID NO:1 by deletion of two amino acids (Asp-Arg) from the N-terminus thereof and substitution of Lys for the 4th residue Arg ([Lys[4]]hCS-15).

[SEQ ID NO:40]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and substitution of Lys for the 2nd residue Arg ([Lys[2]] hCS-13).

[SEQ ID NO:41]
The amino acid sequence of a peptide derived from the peptide having the amino acid sequence defined under SEQ ID NO:1 by deletion of one amino acid (Lys) from the C terminus thereof and substitution of Lys for the 6th residue Arg (des Lys[17][Lys[6]]hCS-17).

[SEQ ID NO:42]
The amino acid sequence of a peptide derived from the peptide having the amino acid sequence defined under SEQ ID NO:1 by deletion of two amino acids (Asp-Arg) from the N terminus thereof and one amino acid (Lys) from the C terminus thereof and substitution of Lys for the 4th residue Arg (des Lys [15][Lys[4]]hCS-15).

[SEQ ID NO:43]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and one amino acid (Lys) from the C terminus thereof and substitution of Lys for the 2nd residue Arg (des Lys [13][Lys[2]]hCS-13).

[SEQ ID NO:44]
The amino acid sequence of a peptide derived from the peptide having the amino acid sequence defined under SEQ ID NO:1 by substitution of Thr for the 14th residue Ser ([Thr[14]]hCS-17).

[SEQ ID NO:45]
The amino acid sequence of a peptide derived from the peptide having the amino acid sequence defined under SEQ ID NO:1 by deletion of two amino acids (Asp-Arg) from the N terminus thereof and substitution of Thr for the 12th residue Ser ([Thr[12]]hCS-15).

[SEQ ID NO:46]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and substitution of Thr for the 10th residue Ser ([Thr[10]]hCS-13).

[SEQ ID NO:47]
The amino acid sequence of a peptide derived from the peptide having the amino acid sequence defined under SEQ ID NO:1 by deletion of one amino acid (Lys) from the C terminus thereof and substitution of Thr for the 14th residue Ser (des Lys[17][Thr[14]]hCS-17).

[SEQ ID NO:48]
The amino acid sequence of a peptide derived from the peptide having the amino acid sequence defined under SEQ ID NO: 1 by deletion of two amino acids (Asp-Arg) from the N terminus thereof and one amino acid (Lys) from the C terminus thereof and substitution of Thr for the 12th residue Ser (des Lys[15][Thr[12]]hCS-15).

[SEQ ID NO:49]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and one amino acid (Lys) from the C terminus thereof and substitution of Thr for the 10th residue Ser (des Lys[13][Thr[10]]hCS-13).

[SEQ ID NO:50]
The amino acid sequence of a peptide derived from the peptide having the amino acid sequence defined under SEQ ID NO:1 by substituion of Lys for the 6th residue Arg and Thr for the 14th residue Ser ([Lys[6],Thr[14]]hCS-17).

[SEQ ID NO:51]
The amino acid sequence of a peptide derived from the peptide having the amino acid sequence defined under SEQ ID NO:1 by deletion of two amino acids (Asp-Arg) from the N terminus thereof and substitution of Lys for the 4th residue Arg and Thr for the 12th residue Ser ([Lys[4],Thr[12]]hCS-15).

[SEQ ID NO:52]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and substitution of Lys for the 2nd residue Arg and Thr for the 10th residue Ser ([Lys[2],Thr[10]]hCS-13).

[SEQ ID NO:53]
The amino acid sequence of a peptide derived from the peptide having the amino acid sequence defined under SEQ ID NO:1 by deletion of one amino acid (Lys) from the C terminus thereof and substitution of Lys for the 6th residue Arg and Thr for the 14th residue Ser (des Lys[17][Lys[6],Thr[14]] hCS-17).

[SEQ ID NO:54]
The amino acid sequence of a peptide derived from the peptide having the amino acid sequence defined under SEQ ID NO:1 by deletion of two amino acid (Asp-Arg) from the N terminus thereof and one amino acid (Lys) from the C terminus thereof and substitution of Lys for the 4th residue Arg and Thr for the 12th residue Ser (des Lys[15][Lys[4],Thr[12]] hCS-15).

[SEQ ID NO:55]
The amino acid sequence of a peptide derived from the peptide having the amino acid sequence defined under SEQ ID NO:1 by deletion of four amino acids (Asp-Arg-Met-Pro)(SEQ ID NO:117) from the N terminus thereof and one amino acid (Lys) from the C terminus thereof and substitution of Lys for the 2nd residue Arg and Thr for the 10th residue Ser (des Lys¹³[Lys²,Thr¹⁰]hCS-13).

[SEQ ID NO:56]
The amino acid sequence of a precursor peptide derived from a precursor peptide having the amino acid sequence defined under SEQ ID NO:4 by substitution of Lys for the 18th residue Arg ([Lys¹⁸]hCS-29).

[SEQ ID NO:57]
The amino acid sequence of a precursor peptide derived from a precursor peptide having the amino acid sequence defined under SEQ ID NO:4 by substitution of Thr for the 26th residue Ser ([Thr²⁶]hCS-29).

[SEQ ID NO:58]
The amino acid sequence of a precursor peptide derived from a precursor peptide having the amino acid sequence defined under SEQ ID NO:4 by substitution of Lys for the 18th residue Arg and Thr for the 26th residue Ser ([Lys¹⁸,Thr²⁶]hCS-29).

[SEQ ID NO:59]
The amino acid sequence of a pr cursor peptide derived from a precursor peptide having the amino acid sequence defined under SEQ ID NO:4 by substitution of Lys for the 18th residue Arg and deletion of the 29th residue Lys (des Lys²⁹[Lys¹⁸]hCS-29).

[SEQ ID NO:60]
The amino acid sequence of a precursor peptide derived from a precursor peptide having the amino acid sequence defined under SEQ ID NO:4 by substitution of Thr for the 26th residue Ser and deletion of the 29th residue Lys (des Lys²⁹[Thr²⁶]hCS-29).

[SEQ ID NO:61]
The amino acid sequence of a precursor peptide derived from a precursor peptide having the amino acid sequence defined under SEQ ID NO: 4 by substitution of Lys for the 18th residue Arg and Thr for the 26th residue Ser (des Lys²⁹[Lys¹⁸,Thr²⁶]hCS-29).

[SEQ ID NO:62]
The nucleotide sequence of a DNA coding for the deletion type mutein having the amino acid sequence defined under SEQ ID NO:35.

[SEQ ID NO:63]
The nucleotide sequence of a DNA coding for the deletion type mutein having the amino acid sequence defined under SEQ ID NO:36.

[SEQ ID NO:64]
The nucleotide sequence of a DNA coding for the deletion type mutein having the amino acid sequence defined under SEQ ID NO:37.

[SEQ ID NO:65]
The nucleotide sequence of a DNA coding for the deletion type mutein having the amino acid sequence defined under SEQ ID NO:38.

[SEQ ID NO:66]
The nucleotide sequence of a DNA coding for the deletion type mutein having the amino acid sequence defined under SEQ ID NO:39.

[SEQ ID NO:67]
The nucleotide sequence of a DNA coding for the deletion type mutein having the amino acid sequence defined under SEQ ID NO:40.

[SEQ ID NO:68]
The nucleotide sequence of a DNA coding for the deletion type mutein having the amino acid sequence defined under SEQ ID NO:41.

[SEQ ID NO:69]
The nucleotide sequence of a DNA coding for the deletion type mutein having the amino acid sequence defined under SEQ ID NO:42.

[SEQ ID NO:70]
The nucleotide sequence of a DNA coding for the deletion type mutein having the amino acid sequence defined under SEQ ID NO:43.

[SEQ ID NO:71]
The nucleotide sequence of a DNA coding for the deletion type mutein having the amino acid sequence defined under SEQ ID NO:44.

[SEQ ID NO:72]
The nucleotide sequence of a DNA coding for the deletion type mutein having the amino acid sequence defined under SEQ ID NO:45.

[SEQ ID NO:73]
The nucleotide sequence of a DNA coding for the deletion type mutein having the amino acid sequence defined under SEQ ID NO:46.

[SEQ ID NO:74]
The nucleotide sequence of a DNA coding for the deletion type mutein having the amino acid sequence defined under SEQ ID NO:47.

[SEQ ID NO:75]
The nucleotide sequence of a DNA coding for the deletion type mutein having the amino acid sequence defined under SEQ ID NO:48.

[SEQ ID NO:76]
The nucleotide sequence of a DNA coding for the deletion type mutein having the amino acid sequence defined under SEQ ID NO:49.

[SEQ ID NO:77]
The nucleotide sequence of a DNA coding for the deletion type mutein having the amino acid sequence defined under, SEQ ID NO:50.

[SEQ ID NO:78]
The nucleotide sequence of a DNA coding for the deletion type mutein having the amino acid sequence defined under SEQ ID NO:51.

[SEQ ID NO:79]
The nucleotide sequence of a DNA coding for the deletion type mutein having the amino acid sequence defined under SEQ ID NO:52.

[SEQ ID NO:80]
The nucleotide sequence of a DNA coding for the deletion type mutein having the amino acid sequence defined under SEQ ID NO:53.

[SEQ ID NO:81]
The nucleotide sequence of a DNA coding for the deletion type mutein having the amino acid sequence defined under SEQ ID NO:54.

[SEQ ID NO:82]
The nucleotide sequence of a DNA coding for the deletion type mutein having the amino acid sequence defined under SEQ ID NO:55.

[SEQ ID NO:83]
The nucleotide sequence of a DNA coding for the precursor peptide having the amino acid sequence defined under SEQ ID NO:56.

[SEQ ID NO:84]
The nucleotide sequence of a DNA coding for the precursor peptide having the amino acid sequence defined under SEQ ID NO:56.

[SEQ ID NO:85]
The nucleotide sequence of a DNA coding for the precursor peptide having the amino acid sequence defined under SEQ ID NO:57.

[SEQ ID NO:86]
The nucleotide sequence of a DNA coding for the precursor peptide having the amino acid sequence defined under SEQ ID NO: 57.

[SEQ ID NO:87]
The nucleotide sequence of a DNA coding for the precursor peptide having the amino acid sequence defined under SEQ ID NO: 58.

[SEQ ID NO:88]
The nucleotide sequence of a DNA coding for the precursor peptide having the amino acid sequence defined under SEQ ID NO:58.

[SEQ ID NO:89]
The nucleotide sequence of a DNA coding for the precursor peptide having the amino acid sequence defined under SEQ ID NO:59.

[SEQ ID NO:90]
The nucleotide sequence of a DNA coding for the precursor peptide having the amino acid sequence defined under SEQ ID NO:59.

[SEQ ID NO:91]
The nucleotide sequence of a DNA coding for the precursor peptide having the amino acid sequence defined under SEQ ID NO:60.

[SEQ ID NO:92]
The nucleotide sequence of a DNA coding for the precursor peptide having the amino acid sequence defined under SEQ ID NO:60.

[SEQ ID NO:93]
The nucleotide sequence of a DNA coding for the precursor peptide having the amino acid sequence defined under SEQ ID NO:61.

[SEQ ID NO:94]
The nucleotide sequence of a DNA coding for the precursor peptide having the amino acid sequence defined under SEQ ID NO:61.

[SEQ ID NO:95]
The nucleotide sequence of a primer used for the cloning of a cDNA coding for human somatostatin receptor protein subtype 1 (SSTR1).

[SEQ ID NO:96]
The nucleotide sequence of a primer used for the cloning of a cDNA coding for human somatostatin receptor protein subtype 1 (SSTR1).

[SEQ ID NO:97]
The nucleotide sequence of a primer used for the cloning of a cDNA coding for human somatostatin receptor protein subtype 2 (SSTR2).

[SEQ ID NO:98]
The nucleotide sequence of a primer used for the cloning of a cDNA coding for human somatostatin receptor protein subtype 2(SSTR2).

[SEQ ID NO:99]
The nucleotide sequence of a primer used for the cloning of a cDNA coding for human somatostatin receptor protein subtype 3 (SSTR3).

[SEQ ID NO:100]
The nucleotide sequence of a primer used for the cloning of a cDNA coding for human somatostatin receptor protein subtype 3 (SSTR3).

[SEQ ID NO:101]
The nucleotide sequence of a primer used for the cloning of a cDNA coding for human somatostatin receptor protein subtype 4 (SSTR4).

[SEQ ID NO:102]
The nucleotide sequence of a primer used for the cloning of a cDNA coding for human somatostatin receptor protein subtypes 4 (SSTR4).

[SEQ ID NO:103]
The nucleotide sequence of a primer used for the cloning of a cDNA coding for human somatostatin receptor protein subtype 5 (SSTR5).

[SEQ ID NO:104]
The nucleotide sequence of a primer used for the cloning of a cDNA coding for human somatostatin receptor protein subtype 5 (SSTR5).

[SEQ ID NO:105]
The nucleotide sequence of a primer used for the cloning of a DNA coding for a peptide of the invention.

[SEQ ID NO:106]
The nucleotide sequence of a primer used for the cloning of a DNA coding for a peptide of the invention.

The transformant *Escherichia coli* JM109/phCSP6 obtained in Example 2 mentioned later herein has been deposited with the Ministry of International Trade and Industry National Institute of Bioscience and Human Technology (NIBH) since Jun. 6, 1996 under the accession number FERN BP-5564 and with the Institute for Fermentation, Osaka (IFO) since Jun. 5, 1996 under the accession number IFO 15967.

The following reference examples and examples illustrate the present invention in further detail. They are, however, by no means limitative of the scope of the present invention. Those gene manipulation procedures described in Molecular Cloning were followed in genetically manipulating *Escherichia coli*.

REFERENCE EXAMPLE 1

Production of Human Somatostatin Receptor Protein Subtype 1 (SSTR1) Expression Cells (1) Cloning of Human Somatostatin Receptor Protein Subtype 1 (SSTR1) DNA DNA oligomers S1-1 and S1-2 were synthesized based on the nucleotide sequence of human SSTR1 cDNA as reported (Yamada et al., Proc. Natl. Acad. Sci., USA, vol. 89, pp. 251–255, 1992). The sequence of S1-1 was 5'-GGTCGAC-CTCAGCTAGGATGTTCCCCAATG-3' (SEQ ID NO: 95) and that of S1-2 was 5'-GGTCGACCCGGGCTCA-GAGCGTCGTGAT-3' (SEQ ID NO:96).

Human chromosomal DNA (Clontech, catalog No. CL6550-1) was used as the template. The DNA oligomers mentioned above (25 pmol each) were added to 0.5 ng of said DNA, and the polymerase chain reaction was carried out using 2.5 units of Pfu DNA polymerase (Stratagene). The composition of the reaction mixture was as indicated in the manual attached to the Pfu DNA polymerase.

The reaction was carried out in 35 cycles, each cycle comprising: 1 minute at 94° C., 1 minute at 63° C., and 2 minutes at 75° C. Upon 1% agarose gel electrophoresis of the reaction mixture, specific amplification of a DNA fragment having the desired size (about 1.2 kb) was confirmed. Said DNA fragment was recovered from the agarose gel in a conventional manner and joined to pUC118 cleaved at the HincII site, followed by introduction into competent cells, namely *Escherichia coli* JM109. A transformant harboring a plasmid containing said DNA fragment was selected and the nucleotide sequence of the insert DNA fragment was confirmed with an automated nucleotide sequence analyzer ALF DNA Sequencer (Pharmacia) using a fluorescent dye, upon which the amino acid sequence deduced from the nucleotide sequence was in complete agreement with the sequence described in the above-cited Yamada et al. report.

(2) Construction of a Human Somatostatin Receptor Protein Subtype 1 (SSTR1) DNA Expression Plasmid pAKKO-111 was used as the expression vector for expression in CHO cells. pAKKO-111 was constructed in the following manner. A 1.4 kb DNA fragment containing the SR α promoter and poly(A) addition signal was obtained from pTB1417 described in Japanese Kokai Tokkyo Koho H05-076385 by treatment with HindIII and ClaI. Separately, a 4.5 kb DNA fragment containing the dihydrofolate reductase (DHFR) gene was obtained from pTB348 [Naruo, K. et al., Biochem. Biophys. Res. Commun., 128, 256–264 (1985)] by treatment with ClaI and SalI. These DNA fragments were rendered blunt-ended by T4 polymerase treatment and then joined together using T4 ligase, whereby the pAKKO-111 plasmid was constructed.

Then, 5 μg of the plasmid obtained as described above in (1) and containing the human SSTR1 DNA fragment was digested with the restriction enzyme SAlI, then 1% agarose gel electrophoresis was carried out, and a 1.2 kb DNA fragment coding for human SSTR1 was recovered. And, 1 μg of the above-mentioned expression vector pAKKO-111 (5.5 kb) was digested with SalI to prepare a cloning site for the insertion of the human SSTR1 DNA fragment. Said expression vector fragment and the 1.2 kb DNA fragment were joined together using T4 DNA ligase, the reaction mixture was introduced into *Escherichia coli*, JM109 by the calcium chloride method and, from among transformants, an expression plasmid, pA1-11-SSTR1, with the human SSTR1 DNA fragment inserted in the regular order relative to the promoter was obtained. A transformant harboring this plasmid is referred to as *Escherichia coli* JM109/pA-1-11-SSTR1.

(3) Introduction of the Human Somatostatin Receptor Protein Subtype 1 (SSTR1) DNA into CHO(dhfr−) Cells and Expression Thereof CHO(dhfr−) cells ($1 \times 10^6$ cells) were cultured on HAM F12 medium containing 10% fetal bovine serum in a dish with a diameter of 8 cm for 24 hours. Into these cells was introduced 10 μg of the human SSTR1 cDNA expression plasmid pA-1-11-SSTR1 obtained as described above in (2) by the calcium phosphate method (Cell Phect Transfection Kit; Pharmacia). At 24 hours after transfection, the medium was exchanged for Dulbecco's modified Eagle's medium (DMEM) containing 10% dialyzed fetal bovine serum, and cells forming a colony on this medium (namely DHFR+ cells) were selected. Further, the cells selected were treated by the limiting dilution method for cloning from a single cell, and the somatostatin receptor protein activity was measured in the following manner. The human SSTR1 cDNA expression cell line was diluted with measurement buffer [50 mM Tris-hydrochloride, 1 mM EDTA, 5 mM magnesium chloride, 0.1% bovine serum albumin (BSA), 0.2 mg/ml bacitracin, 10 μg/ml leupeptin, 1 μg/ml pepstatin, 200 units/ml aprotinin (pH 7.5)], the number of cells was adjusted to $2 \times 10^4$ per 200 μl. The cell suspension was distributed in 200-μl portions into tubes, 2 μl of 5 nM [$^{125}$I]-somatostatin-14 (2,000 Ci/mmol, Amersham) was added to each tube, and incubation was carried out at 25° C. for 60 minutes. Separately, for non-specific binding (NSB) measurement, a tube with 2 μl of somatostatin-14 ($10^{-4}$ M) added was also incubated. Washing buffer [50 mM Tris-hydrochloride, 1 mM EDTA, 5 mM magnesium chloride (pH 7.5)] (1.5 ml) was added, followed by filtration through a GF/F glass fiber filter paper (Whatman) and washing with the same buffer (1.5 ml). The [$^{125}$I] on the filter paper was measured with a γ counter. In this manner, a cell line with high somatostatin-binding activity, SSTR1-8-3, was selected.

REFERENCE EXAMPLE 2

Production of Human Somatostatin Receptor Protein Subtype 2 (SSTR2) Expression Cells (1) Cloning of Human Somatostatin Receptor Protein Subtype 2 (SSTR2) cDNA DNA oligomers PT-1 and PT-2 were synthesized based on the nucleotide sequence of human SSTR2 cDNA as reported (Yamada et al., Proc. Natl. Acad. Sci., USA, vol. 89, pp. 251–255, 1992). PT-1 was an oligomer having a nucleotide sequence represented by 5'-GGTCGACACCATGGACATGGCG GATGAG-3' (SEQ ID NO:97) and containing a sequence recognizing the restriction enzyme SalI at the 5' terminus and a sense sequence ranging from −2 to +18 (the translation initiation site being defined as +1). ST-2 was an oligomer having a sequence represented by 5'-GGTCGACAGTTCAGATACTGGTTTGG-3' (SEQ ID NO:98) and containing a recognition sequence for the restriction enzyme SalI at the 5' terminus and an antisense sequence ranging from +1095 to +1114.

Human pituitary cDNA (Clontech, catalog number 7173-1) was used as the template. The DNA oligomers mentioned above (25 pmol each) were added to 1 ng of said cDNA, and the polymerase chain reaction was carried out using 2.5 units of Taq DNA polymerase (Takara Shuzo). The composition of the reaction mixture was as indicated in the manual attached to the Taq DNA polymerase.

The reaction was carried out in 30 cycles, each cycle comprising: 30 seconds at 94° C., 20 seconds at 52° C. and 60 seconds at 72° C. The reaction mixture was subjected to 1% agarose gel electrophoresis, whereupon specific amplification of a DNA fragment having the desired size (about 1.1 kb) was confirmed. Said DNA fragment was recovered from the agarose gel in the conventional manner and jointed to pUC118 cleaved at the HincII site, followed by introduction into competent cells, namely *Escherichia coli* JM109. Two transformant strains (No. 5 and No. 7) harboring a plasmid containing said DNA fragment were selected and analyzed by an automated nucleotide sequencer 373A (Applied Biosystems) for confirmation of the nucleotide sequence of the insert DNA fragment, whereupon one point mutation was confirmed in the sequence of a 770-base fragment between SalI-BstPI of strain No. 5 and one point mutation was confirmed in the sequence of a 360-base fragment between BstPI-SalI in strain No. 7. Therefore, the fragments remaining after removal of the BstPI-SalI fragment of strain No. 5 and of the BstPI-SalI of strain No. 7 were purified by agarose gel electrophoresis and joined together by the ligation reaction to construct a plasmid. The nucleotide sequence of the insert DNA fragment of this plasmid as confirmed was in complete agreement with the nucleotide sequence of the human SSTR2 cDNA as described in the above-cited Yamada et al. report.

(2) Construction of a Human Somatostatin Receptor Protein Subtype 2 (SSTR2) cDNA Expression Plasmid The expression vector used for expression in CHO cells was pAKKO-111 described in Reference Example 1 (1).

The human SSTR2 cDNA fragment-containing plasmid (5 µg) obtained as described above in (1) was digested with the restriction enzyme SalI and subjected to 1% agarose gel electrophoresis, and a 1.1 kb DNA fragment coding for human SSTR2 was recovered. And, 1 µg of the above-mentioned expression vector pAKKO-111 (5.5 kb) was digested with SalI for preparing a cloning site for the insertion of the human SSTR2 cDNA fragment. Said expression vector fragment and the 1.1 kb DNA fragment were joined together using T4 DNA ligase, the ligation mixture was introduced into *Escherichia coli* JM109 by the calcium chloride method and, from among transformants, an expression plasmid, pAC01 with the human SSTR2 cDNA fragment inserted in the regular order relative to the promoter was obtained. A transformant harboring this plasmid pAC01 is referred to as *Escherichia coli* JM109/pAC01.

(3). Introduction of the Human Somatostatin Receptor Protein Subtype 2 (SSTR2) cDNA into CHO(dhfr⁻) Cells and Expression Thereof CHO(dhfr⁻) cells (1×10⁶ cells) were cultured on-HAM F12 medium containing 10% fetal bovine serum in a dish with a diameter of 8 cm for 24 hours. Into these cells was introduced 10 µg of the human SSTR2 cDNA expression plasmid pAC01 obtained as described above in (2) by the calcium phosphate method (Cell Phect Transfection Kit; Pharmacia). At 24 hours after transfection, the medium was exchanged for DMEM containing 10% dialyzed fetal bovine serum, and cells forming a colony on this medium (namely DHFR⁺ cells) were selected. Further, the cells selected were treated by the limiting dilution method for cloning from a single cell, and a cell line, SSTR2-HS5-9, capable of high expression of human SSTR2 was selected.

REFERENCE EXAMPLE 3

Production of Human Somatostatin Receptor Protein Subtype 3 (SSTR3) Expression Cells (1) Cloning of Human Somatostatin Receptor Protein Subtype 3 (SSTR3) DNA DNA oligomers, S3-1 and S3-2, were synthesized based on the nucleotide sequence of human SSTR3 cDNA as reported (Yamada et al., Molecular Endocrinology, vol. 6, pp. 2136–2142, 1992). The sequence of S3-1 was 5'-GGTC-GACCTCAACCATGGACATGCTTCATC-3' (SEQ ID NO:99) and the sequence of S3-2 was 5'-GGTCGACTTTC-CCCAGGCCCCTACAGGTA-3' (SEQ ID NO:100).

Human chromosomal DNA (Clontech, catalog No. CL6550-1) was used as the template. The DNA oligomers mentioned above (25 pmol each) were added to 0.5 ng of said DNA, and the polymerase chain reaction was carried out using 2.5 units of Pfu DNA polymerase (Stratagene). The composition of the reaction mixture was as indicated in the manual attached to the Pfu DNA polymerase.

The reaction was carried out in 35 cycles each cycle comprising: 1 minute at 94° C., minute at 63° C., and 2 minutes at 75° C. Upon 1% agarose gel electrophoresis of the reaction mixture, specific amplification of a DNA fragment having the desired size (about 1.3 kb) was confirmed. The nucleotide sequence of said DNA fragment was confirmed by the method described in Reference Example 1 (1). The amino acid sequence deduced from the nucleotide sequence was in complete agreement with the sequence described in the above-cited Yamada et al. report.

(2) Construction of a Human Somatostatin Receptor Protein Subtype 3 (SSTR3) DNA Expression Plasmid The expression vector used for expression in CHO cells was pAKKO-111 described in Reference Example 1 (2). The human SSTR3 DNA fragment-containing plasmid (5 µg) obtained as described above in (1) was digested with the restriction enzyme SalI and subjected to 1% agarose gel electrophoresis, and a 1.3 kb DNA fragment coding for human SSTR3 was recovered. And, 1 µg of the above-mentioned expression vector pAKKO-111 (5.5 kb) was digested with SalI for preparing a cloning site for the insertion of the human SSTR3 DNA fragment. Said expression vector fragment and the 1.3 kb DNA fragment were joined together using T4 DNA ligase, the reaction mixture was introduced into *Escherichia coli* JM109 by the calcium chloride method and, from among transformants, an expression plasmid, pA-1-11-SSTR3 with the human SSTR3 DNA fragment inserted in the regular order relative to the promoter was obtained. A transformant harboring this plasmid pA-1-11-SSTR3 is referred to as *Escherichia coli* JM109/pA-1-11-SSTR3.

(3) Introduction of the Human Somatostatin Receptor Protein Subtype 3 (SSTR3) DNA into CHO (dhfr⁻) Cells and Expression Thereof CHO(dhfr⁻) cells (1×10⁶ cells) were cultured on HAM F12 medium containing 10% fetal bovine serum in a dish with a diameter of 8 cm for 24 hours. Into these cells was introduced 10 µg of the human SSTR3 DNA expression plasmid pA-1-11-SSTR3 obtained as described above in (2) by the calcium phosphate method (Cell Phect Transfection Kit; Pharmacia). At 24 hours after transfection, the medium was exchanged for DMEM containing 10% dialyzed fetal bovine serum, and cells forming a colony on this medium (namely DHFR⁺ cells) were selected. Further, the cells selected were treated by the limiting dilution method for cloning from a single cell, and the cells thus cloned were measured for their somatostatin receptor protein expression ability by the binding assay described in Reference Example 1 (3), and a cell line with high somatostatin-binding activity, SSTR3-15-19, was selected.

REFERENCE EXAMPLE 4

Production of Human Somatostatin Receptor Protein Subtype 4 (SSTR4) Expression Cells (1) Cloning of Human Somatostatin Receptor Protein Subtype 4 (SSTR4) DNA DNA oligomers S4-1 and S4-2 were synthesized based on the nucleotide sequence of human SSTR4 cDNA as reported (Rohrer et al., Proc. Natl. Acad. Sci., USA, vol. 90, pp. 4196–4200, 1993). The sequence of S4-1 was 5'-GGCTC-GAGTCACCATGAGCGCCCCCTCG-3' (SEQ ID NO:101) and the sequence of S4-2 was 5'-GGGCTC-GAGCTCCTCAGAAGG-TGGTGG-3' (SEQ ID NO:102).

Human chromosomal DNA (Clontech, catalog No. CL6550-1) was used as the template. The DNA oligomers mentioned above (25 pmol each) were added to 0.5 ng of said DNA, and the polymerase chain reaction was carried out using 2.5 units of Pfu DNA polymerase (Stratagene). The composition of the reaction mixture was as indicated in the manual attached to the Pfu DNA polymerase.

The reaction was carried out in 35 cycles, each cycle comprising: 1 minute at 94° C., 1 minute at 63° C., and 2 minutes at 75° C. Upon 1% agarose gel electrophoresis of the reaction mixture, specific amplification of a DNA fragment having the desired size (about 1.2 kb) was confirmed. The nucleotide sequence of said DNA fragment was confirmed by the method described in Reference Example 1 (1). The amino acid sequence deduced from the nucleotide-sequence was in complete agreement with the sequence described in the above-cited Rohrer et al. report.

(2) Construction of a Human Somatostatin Receptor Protein Subtype 4 (SSTR4) DNA Expression Plasmid The expression vector used for expression in CHO cells was pAKKO-111 described in Reference Example 1 (2).

The human SSTR4 DNA fragment-containing plasmid (5 μg) obtained as described above in (1) was digested with the restriction enzyme XhoI and subjected to 1% agarose gel electrophoresis, and a 1.2 kb DNA fragment coding for human SSTR4 was recovered. And, 1 μg of the above-mentioned expression vector pAKKO-111 (5.5 kb) was digested with SalI for preparing a cloning site for the insertion of the human SSTR4 DNA fragment. Said expression vector fragment and the 1.2 kb DNA fragment were joined together using T4 DNA ligase, the reaction mixture was introduced into *Escherichia coli* JM109 by the calcium chloride method and, from among transformants, an expression plasmid, pA-1-11-SSTR4 with the human SSTR4 DNA fragment inserted in the regular order relative to the promoter was obtained. A transformant harboring this plasmid pA-1-11-SSTR4 is referred to as *Escherichia coli* JM109/pA-1-11-SSTR4.

(3) Introduction of the Human Somatostatin Receptor Protein Subtype 4 (SSTR4) DNA into CHO (dhfr⁻) Cells and Expression Thereof CHO(dhfr⁻) cells (1×10⁶ cells) were cultured on HAM F12 medium containing 10% fetal bovine serum in a dish with a diameter of 8 cm for 24 hours. Into these cells was introduced 10 μg of the human SSTR4 DNA expression plasmid pA-1-11-SSTR4 obtained as described above in (2) by the calcium phosphate method (Cell Phect Transfection Kit; Pharmacia). At 24 hours after transfection, the medium was exchanged for DMEM containing 10% dialyzed fetal bovine serum, and cells forming a colony on this medium (namely DHFR⁺ cells) were selected. Further, the cells selected were treated by the limiting dilution method for cloning from a single cell, and the cells thus cloned were measured for their somatostatin receptor protein expression ability by the binding assay described in Reference Example 1 (3). In this manner, a cell line with high somatostatin-binding activity, SSTR4-1-2, was selected.

REFERENCE EXAMPLE 5

Production of Human Somatostatin Receptor Protein Subtype 5 (SSTR5) Expression Cells (1) Cloning of Human Somatostatin Receptor Protein Subtype 5 (SSTR5) DNA DNA oligomers S5-1 and S5-2 were synthesized based on the nucleotide sequence of human SSTR5 cDNA as reported (Yamada et al., Biocehm. Biophys. Res. Commun., vol. 195, pp. 844–852, 1993). The sequence of S5-1 was 5'-GGTC-GACCACCATGGAGCCCCTGTTCCC-3' (SEQ ID NO:103) and the sequence of S5-2 was 5'-CCGTCGA-CACTCTCACAGCTTGCTGG-3' (SEQ ID NO:104).

Human chromosomal DNA (Clontech, catalog No. CL6550-1) was used as the template. The DNA oligomers mentioned above (25 pmol each) were added to 0.5 ng of said DNA, and the polymerase chain-reaction was carried out using 2.5 units of Pfu DNA polymerase (Stratagene). The composition of the reaction mixture was as indicated in the manual attached to the Pfu DNA polymerase.

The reaction was carried out in 35 cycles, each cycle comprising: 1 minute at 94° C., 1 minute at 66° C., and 2 minutes at 75° C. Upon 1% agarose gel electrophoresis of the reaction mixture, specific amplification of a DNA fragment having the desired size (about 1.1 kb) was confirmed. The nucleotide sequence of said DNA fragment was confirmed by the method described in Reference Example 1 (1). The amino acid sequence deduced from the nucleotide sequence was in complete agreement with the sequence described in the above-cited Yamada et al. report.

(2) Construction of a Human Somatostatin Receptor Protein Subtype 5 (SSTR5) DNA Expression Plasmid The expression vector used for expression in CHO cells was pAKKO-111 described in Reference Example 1 (2).

The human SSTR5 DNA fragment-containing plasmid (5 μg) obtained as described above in (1) was digested with the restriction enzyme SalI and subjected to 1% agarose gel electrophoresis, and a 1.1 kb DNA fragment coding for human SSTR5 was recovered. And, 1 μg of the above-mentioned expression vector pAKKO-111 (5.5 kb) was digested with SalI for preparing a cloning site for the insertion of the human SSTR5 DNA fragment. Said expression vector fragment and the 1.1 kb DNA fragment were joined together using T4 DNA ligase, the reaction mixture was introduced into *Escherichia coli* JM109 by the calcium chloride method and, from among transformants, an expression plasmid, pA-1-11-SSTR5 with the human SSTR5 DNA fragment inserted in the regular order relative to the promoter was obtained. A transformant harboring this plasmid pA-1-11-SSTR5 is referred to as *Escherichia coli* JM109/pA-1-11-SSTR5.

(3) Introduction of the Human Somatostatin Receptor Protein Subtype 5 (SSTR5) DNA into CHO (dhfr⁻) Cells and Expression Thereof CHO(dhfr⁻) cells (1×10⁶ cells) were cultured on HAM F12 medium containing 10% fetal bovine serum in a dish with a diameter of 8 cm for 24 hours. Into these cells was introduced 10 μg of the human SSTR5 cDNA expression plasmid pA-1-11-SSTR5 obtained as described above in (2) by the calcium phosphate method (Cell Phect Transfection Kit; Pharmacia). At 24 hours after transfection, the medium was exchanged for DMEM containing 10% dialyzed fetal bovine serum, and cells forming a colony on this medium (namely DHFR⁺ cells) were selected. Further, the cells selected were treated by the limiting dilution method for cloning from a single cell, and the cells thus cloned were measured for their somatostatin receptor protein expression ability by the binding assay described in Reference Example 1 (3). In this manner, a cell line with high somatostatin-binding activity. SSTR5-32-4, was selected.

REFERENCE EXAMPLE 6

Preparation of Human Somatostatin Receptor-Containing CHO cell Membrane Fractions The human somatostatin receptor expressing CHO cell lines SSTR1-8-3, SSTR2-HS5-9, SSTR3-15-19, SSTR4-1-2 and SSTR5-32-4 ($10^9$ cells each) were respectively suspended in phosphate buffered physiological saline supplemented with 5 mM EDTA (PBS-EDTA) and centrifuged. To each cell pellet was added 10 ml of cell homogenation buffer (10 mM $NaHCO_3$, 5 mM EDTA, pH=7.5), followed by homogenation with a Polytron homogenizer. The homogenate was centrifuged at 400×g for 15 minutes, and the supernatant obtained was further centrifuged at 100,000×g for 1 hour to give a membrane fraction as a precipitate. This precipitate was suspended in 2 ml of assay buffer (25 mM Tris-HCl, 1 mM EDTA, 0.1% BSA, 0.25 mM phenylmethanesulfonyl fluoride (PMSF), 1 µg/ml pepstatin, 20 µg/ml leupeptin, 10 µg/ml phosphoramidon, pH=7.5) and the suspension was centrifuged at 100,000×g for 1 hour. The membrane fraction recovered as a precipitate was again suspended in 20 ml of assay buffer, and the suspension is distributed into tubes, stored at −80% and thawed each time prior to use.

EXAMPLE 1

Synthesis of cDNA from a Human Brain Poly(A) RNA Fraction and Amplification of a Physiologically Active Peptide cDNA by the RT-PCR Technique To 5 µg of a human brain poly(A)$^+$ RNA fraction purchased from Clontech was added a random DNA hexamer mixture (BRL) as the primer, and complementary DNA synthesis was carried out using Moloney murine leukemia virus-derived reverse transcriptase (BRL) and the buffer attached thereto. After the reaction, the product was extracted with phenol-chloroform (1:1) and precipitated with ethanol, and the precipitate was dissolved in 30 µl of TE (10 mM Tris-HCl (pH 7.5), 1 mM EDTA). Using 1 µl of the thus-prepared cDNA as a template, amplification was carried out by PCR using the following two primers:

5'-ACAAGATGCCATTGTCCCCGGCCTCCT-3' (SEQ ID NO:105)

5'-TTCAGGTCTGTAATTAAACTTGCGTGA-3' (SEQ ID NO:106)

The composition of the reaction mixture was as follows: synthetic DNA primers (5' primer sequence and 3' primer sequence) 10 pM each, 0.25 mM dNTPs, Ex Taq DNA polymerase 0.5 µl and the buffer attached to the enzyme 10 µl, the total reaction mixture amounting to 100 µl. Amplification was carried out, using a Thermal Cycler apparatus (Perkin Elmer), in 35 cycles each comprising: 30 seconds at 95° C., 1 minute at 65° C. and 30 seconds at 72° C. The amplification product was identified by 1.2% agarose electrophoresis and ethidium bromide staining.

EXAMPLE 2

Subcloning of the PCR Product into a Plasmid Vector and Selection of a Novel Physiologically Active Peptide Candidate Clone The reaction product after the PCR carried out in Example 1 was separated using a 1.2% agarose gel, the band was excised with a razor and, then, the DNA was recovered by SUPRECOI™ (Takara) treatment, phenol extraction and ethanol extraction. The DNA recovered was subcloned into the plasmid vector pCR™II according to the prescription of TA Cloning Kit (Invitogen). This was introduced into Escherichia coli JM109 competent cells (Takara Shuzo) and, thereafter, clones having the cDNA insert-fragment were selected in LB agar medium containing ampicillin, IPTG and X-gal and, by isolating a white-colored clone alone using a sterile toothpick, whereby a transformant, Esoherichia coli JM109/phCSP6, was obtained.

This clone was cultured overnight in ampicillin-containing LB medium and a plasmid DNA was prepared using an automated plasmid extractor (Kurabo). A portion of the DNA prepared was cleaved with EcoRI and the size of the cDNA fragment inserted therein was confirmed. Another portion of the remaining DNA was further subjected to RNase treatment, phenol/chloroform extraction and ethanol precipitation for the purpose of concentration. The reaction for nucleotide sequence determination was carried out using a DyeDeoxy Terminator Cycle Sequencing Kit (ABI) and decoding was carried out using a fluorescence-based automated sequencer. The nucleotide sequence information obtained was processed using a DNA SIS system (Hitachi System Engineering). The nucleotide sequence thus determined is shown in FIG. 1.

Figure 4:
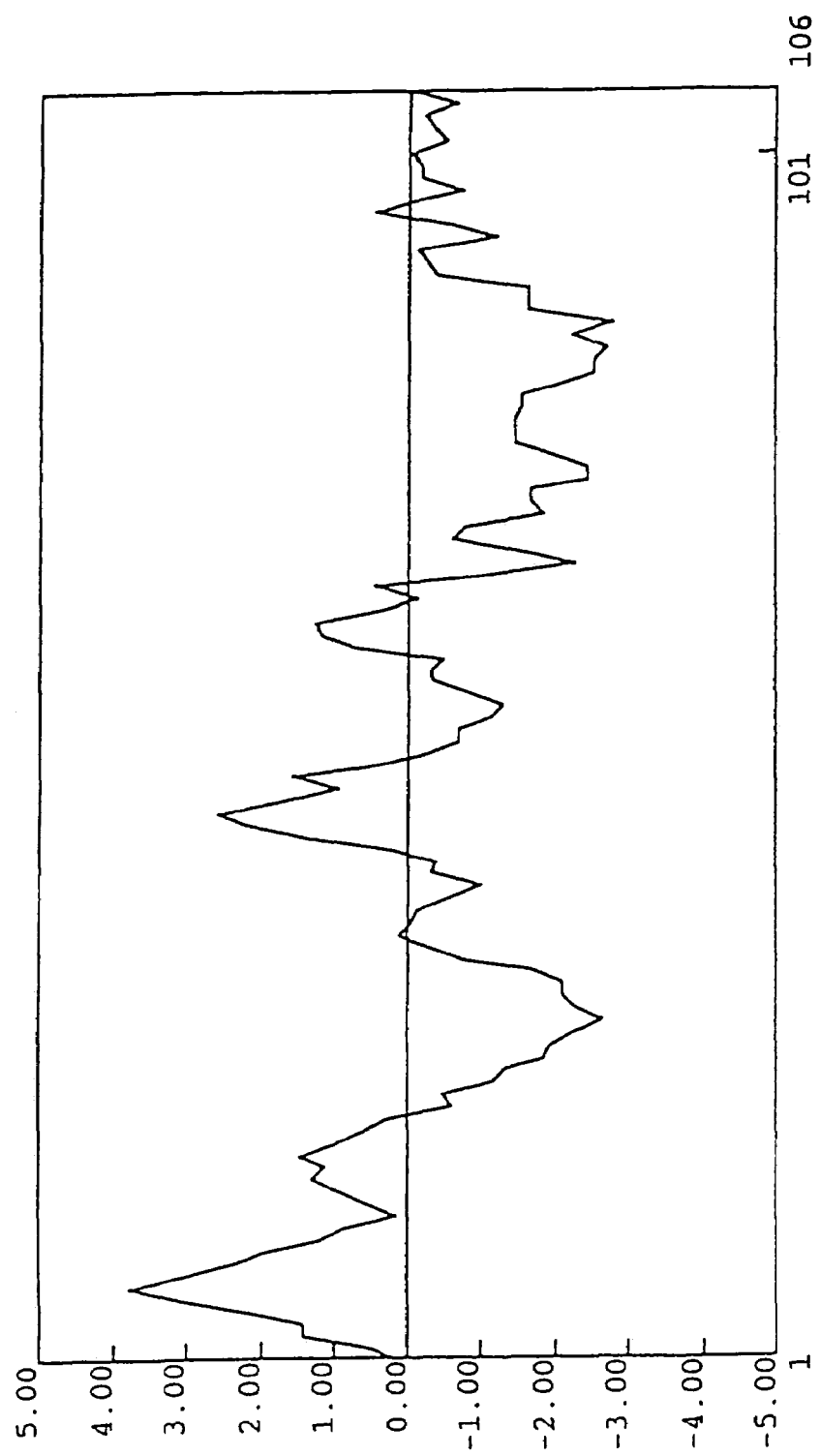
FIG. 4 shows the results of hydrophobicity plotting analysis of the amino acid sequence of the precursor of the invention shown in FIG. 2.
Figure 5:
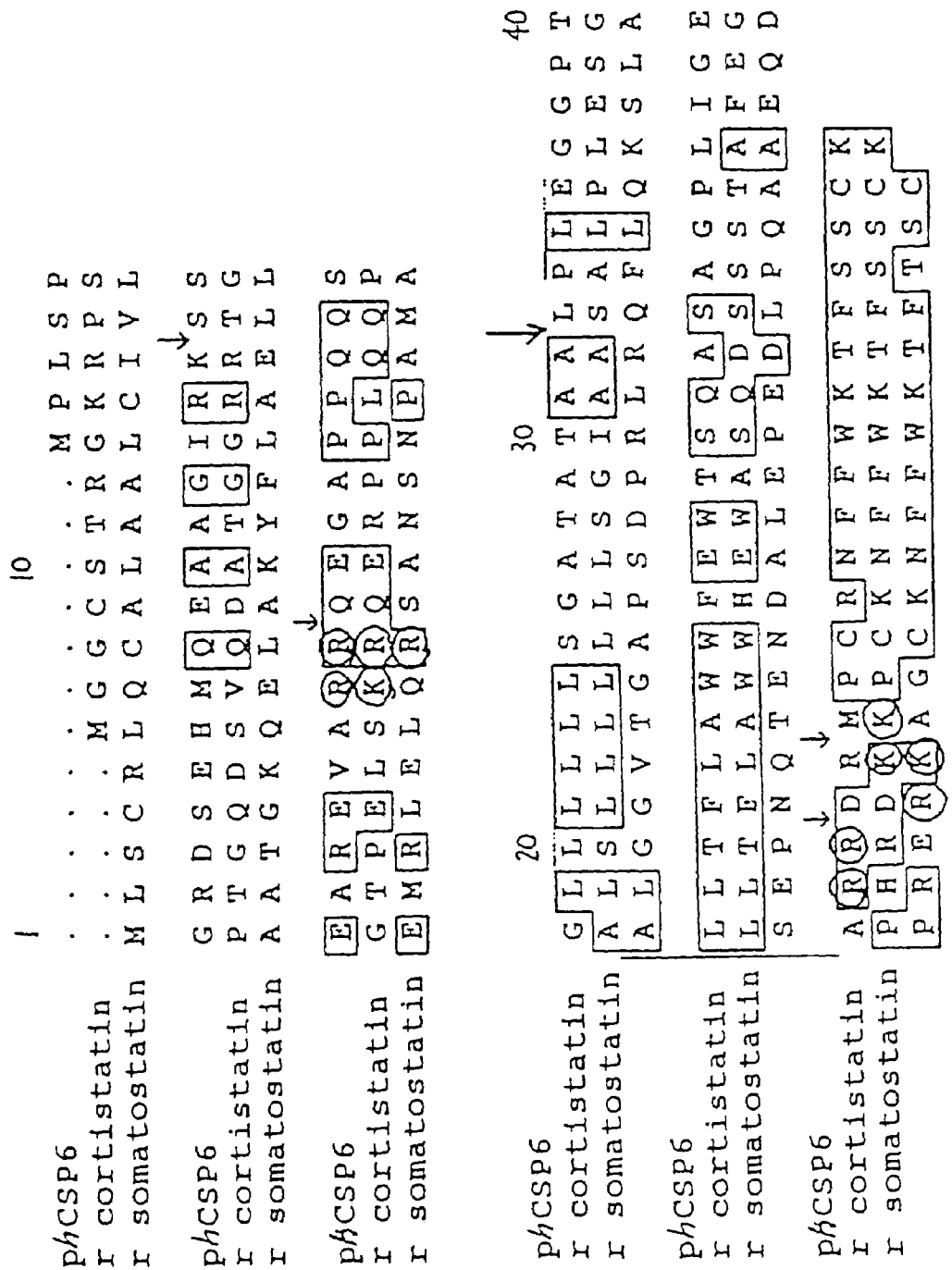
FIG. 5 shows the results of amino acid sequence comparison of the precursor (phCSP6) of the invention shown in FIG. 2 SEQ ID NO: 112 with rat cortistatin (r cortistatin; U51919) SEQ ID NO: 113 and rat somatostatin (r somatostatin; J00788) SEQ ID NO: 114.

Based on the nucleotide sequence determined (FIG. 1), homology searching was carried out and, as a result, it was found that the cDNA fragment inserted-into the plasmid harbored by the transformant Escherichia coli JM109/phCSP6 codes for a novel physiologically active peptide. Furthermore, for confirming that fact, the nucleotide sequence was converted to an amino acid sequence using a DNASIS system (Hitachi System Engineering) (FIG. 2), followed by homology searching based on hydrophobicity plotting (FIG. 4) and on the amino acid sequence, whereupon homology with rat cortistatin (U51919) and rat somatostatin (J00788) was found (FIG. 5).

The abbreviations in the above parentheses are serial numbers given on the occasion of registration of data thereon with the NBRF-PIR and generally referred to as accession numbers.

EXAMPLE 3

Synthesis of Human Peptide hCS-17 (SEQ ID NO:1):

Asp-Arg-Met-Pro-Cys-Arg-Asn-Phe-Phe-Trp-Lys-Thr-Phe-Ser-Ser-Cys-Lys

1) Synthesis of Boc-Asp(OcHex)-Arg(Tos)-Met-Pro-Cys (MeBzl)-Arg(Tos)-Asn-Phe-Phe-Trp(CHO)-Lys(Cl-Z)-Thr (Bzl)-Phe-Ser(Bzl)-Ser(Bzl)-Cys(MeBzl)-Lys(Cl-Z)-OCH2-PAM resin (SEQ ID NO:119)

The reactor of a peptide synthesizer, ABI-410A, was charged with a commercial resin, Boc-Lys(Cl-Z)-OCH$_2$PAM (0.65 mmole/gram) and, then, Boc-Cys(MeBzl), Boc-Ser(Bzl), Boc-Phe, Boc-Thr(Bzl), Boc-Lys(Cl-Z), Boc-Trp(CHO), Boc-Asn, Boc-Arg(Tos), Boc-Pro, Boc-Met, Moc-Asp(OcHex) were subjected to condensation by the Boc/HOBT/NMP technique in the order of the amino acid sequence (SEQ ID NO: 1), from the C terminus, of the human cortistatin-like peptide. The condensation reaction was checked by a ninhydrin test and, if the amino group was found unreacted, the condensation reaction was carried out again until attainment of sufficient condensation and, after introduction of all the amino acids into the resin as indicated by said sequence, 0.9235 g of the protected peptide resin was obtained.

2) The resin obtained in 1) (0.15 g) was treated with 1.7 g of para-cresol, 2.5 ml of 1,4-butanedithiol and 25 ml of hydrogen fluoride at 0° C. for 1 hour. The hydrogen fluoride and 1,4-butanedithiol were distilled off under reduced pressure, 100 ml of diethyl ether was added to the residue and, after stirring, the solid was collected on a glass filter and dried. This was suspended in 50 ml of 50% (v/v; hereinafter the same shall apply) aqueous acetic acid solution and the suspension was stirred for extraction of the peptide. The extract was separated from the resin, concentrated to about 5 ml under reduced pressure and applied to a Sephadex G-25 column (2×90 cm), followed by development with 50% acetic acid-water. The 120–170 ml fractions were combined and the solvent was distilled off. The residue is dissolved in 2 ml of 2 M aqueous ammonium acetate solution, further diluted to 400 ml by addition of deaerated distilled water, adjusted to pH 8 by addition of dilute aqueous ammonia, and oxidized by blowing air slowly into the solution at room temperature. After confirmation of disappearance of the peak of the raw material peptide by HPLC, the pH was adjusted to 4 or below by addition of acetic acid and the solution was applied to a reversed phase column (LiChroprep RP-18, 2.6×10 cm; E. Merck), and gradient elution was carried out from 0.1% trifluoroacetic acid-water to 50% aqueous acetonitrile solution containing 0.1% trifluoroacetic acid. The eluate fractions corresponding to the concentrations of 30–35% were combined and lyophilized to give 38 mg of a white powder. Then, this white powder was applied to a weakly acidic ion exchange chromatography column (Cellulofine C-500, 2.6×5 cm; Seikagaku Corp.), followed by gradient elution with ammonium acetate-water. The eluate fractions corresponding to about 0.3 M ammonium acetate were combined and lyophilized to give 18.8 mg of a powder. The product obtained was further applied to a Sephadex G-25 gel filtration column (2×90 cm) using 50% acetic acid-water and eluted with the same solvent. The 183–225 ml fractions were combined and lyophilized to give 18.24 mg of the human peptide hCS-17.

(M+H)$^+$ by mass spectrometric analysis: 2150.9460 (calculated value: 2150.9730)

Elution time in HPLC: 19.3 minutes

Column conditions:

Column: Wakosil™ 5C18 (4.6×100 mm)

Eluent: Solution A (0.1% TFA-water)
    Solution B (0.1% TFA-containing 50% acetonitrile-water; Linear concentration gradient elution (25 minutes) from solution A to Solution B Flow rate: 1.0 ml/min.

EXAMPLE 4

Synthesis of Deletion Type Human Peptide hCS-15 (SEQ ID NO:2):

Met-Pro-Cys-Arg-Asn-Phe-Phe-Trp-Lys-Thr-Phe-Ser-Ser-Cys-Lys

1) Synthesis of Boc-Met-Pro-Cys(MeBzl)-Arg(Tos)-Asn-Phe-Phe-Trp(CHO)-Lys(Cl-Z)-Thr(Bzl)-Phe-Ser(Bzl)-Ser(Bzl)-Cys(MeBzl)-Lys(Cl-Z)-OCH$_2$—PAM resin (SEQ ID NO:120)

Following the procedure of Example 3, all the necessary amino acids were introduced into the resin in the order as indicated by the sequence, to give 0.477 g of the protected peptide resin.

2) A 0.20-g portion of the resin obtained in 1) was subjected to hydrogen fluoride treatment, oxidation with air for S—S bond formation, and chromatographic purification, to give 17.7 mg of the deletion type human peptide hCS-15.

(M+H)$^+$ by mass spectrometric analysis: 1879.7610 (calculated value: 1879.7850)

Elution time in HPLC: 19.6 minutes

Column conditions:

Column: Wakosil™ 5C18 (4.6×100 mm)

Eluent: Solution A (0.1% TFA-water)
    Solution B (0.1% TFA-containing 50% acetonitrile-water; Linear concentration gradient elution (25 minutes) from solution A to Solution B Flow rate: 1.0 ml/min.

EXAMPLE 5

Synthesis of Deletion Type Human Peptide hCS-13 (SEQ ID NO:3):

Cys-Arg-Asn-Phe-Phe-Trp-Lys-Thr-Phe-Ser-Ser-Cys-Lys

1) Synthesis of Boc-Cys(MeBzl)-Arg(Tos)-Asn-Phe-Phe-Trp(CHO)-Lys(Cl-Z)-Thr(Bzl)-Phe-Ser(Bzl)-Ser(Bzl)-Cys(MeBzl)-Lys(Cl-Z)-OCH$_2$—PAM resin (SEQ ID NO:121)

Following the procedure of Example 3, all the necessary amino acids were introduced into the resin in the order as indicated by the sequence, to give 0.603 g of the protected peptide resin.

2) A 0.14-g portion of the resin obtained in 1) was subjected to hydrogen fluoride treatment, oxidation with air for S—S bond formation, and chromatographic purification, to give 17.7 mg of the deletion type human peptide hCS-13.

(M+H)$^+$ by mass spectrometric analysis: 1651.5830 (calculated value: 1651.7510)

Elution time in HPLC: 19.0 minutes

Column conditions:

Column: Wakosil™ 5C18 (4.6×100 mm)

Eluent: Solution A (0.1% TFA-water)
    Solution B (0.1% TFA-containing 50% acetonitrile-water; Linear concentration gradient elution (25 minutes) from solution A to Solution B Flow rate: 1.0 ml/min. Example 6 Synthesis of deletion type human des Lys$^{17}$ hCS-17 (SEQ ID NO:35):

Asp-Arg-Met-Pro-Cys-Arg-Asn-Phe-Phe-Trp-Lys-Thr-Phe-Ser-Ser-Cys

The above peptide can be synthesized in the same manner as in Example 3 using Boc-Cys(MeBzl)-OCH$_2$-PAM resin in lieu of the Boc-Lys(Cl-Z)-OCH$_2$-PAM resin of Example 3.

EXAMPLE 7

Synthesis of Deletion Type Human Peptide des Lys$^{15}$ hCS-15 (SEQ ID NO:36):

Met-Pro-Cys-Arg-Asn-Phe-Phe-Trp-Lys-Thr-Phe-Ser-Ser-Cys

The above peptide can be synthesized in the same manner as in Example 4 using Boc-Cys(MeBzl)-OCH$_2$-PAM resin in lieu of the Boc-Lys(Cl-Z)-OCH$_2$-PAM resin.

EXAMPLE 8

Synthesis of Deletion Type Human Peptide des Lys$^{13}$ hCS-13 (SEQ ID NO:37):

Cys-Arg-Asn-Phe-Phe-Trp-Lys-Thr-Phe-Ser-Ser-Cys

The above peptide can be synthesized in the same manner as in Example 5 using Boc-Cys(MeBzl)-OCH$_2$-PAM resin in lieu of the Boc-Lys(Cl-Z)-OCH$_2$—PAM resin.

EXAMPLE 9

Northern Hybridization of phCSP6

Figure 6:
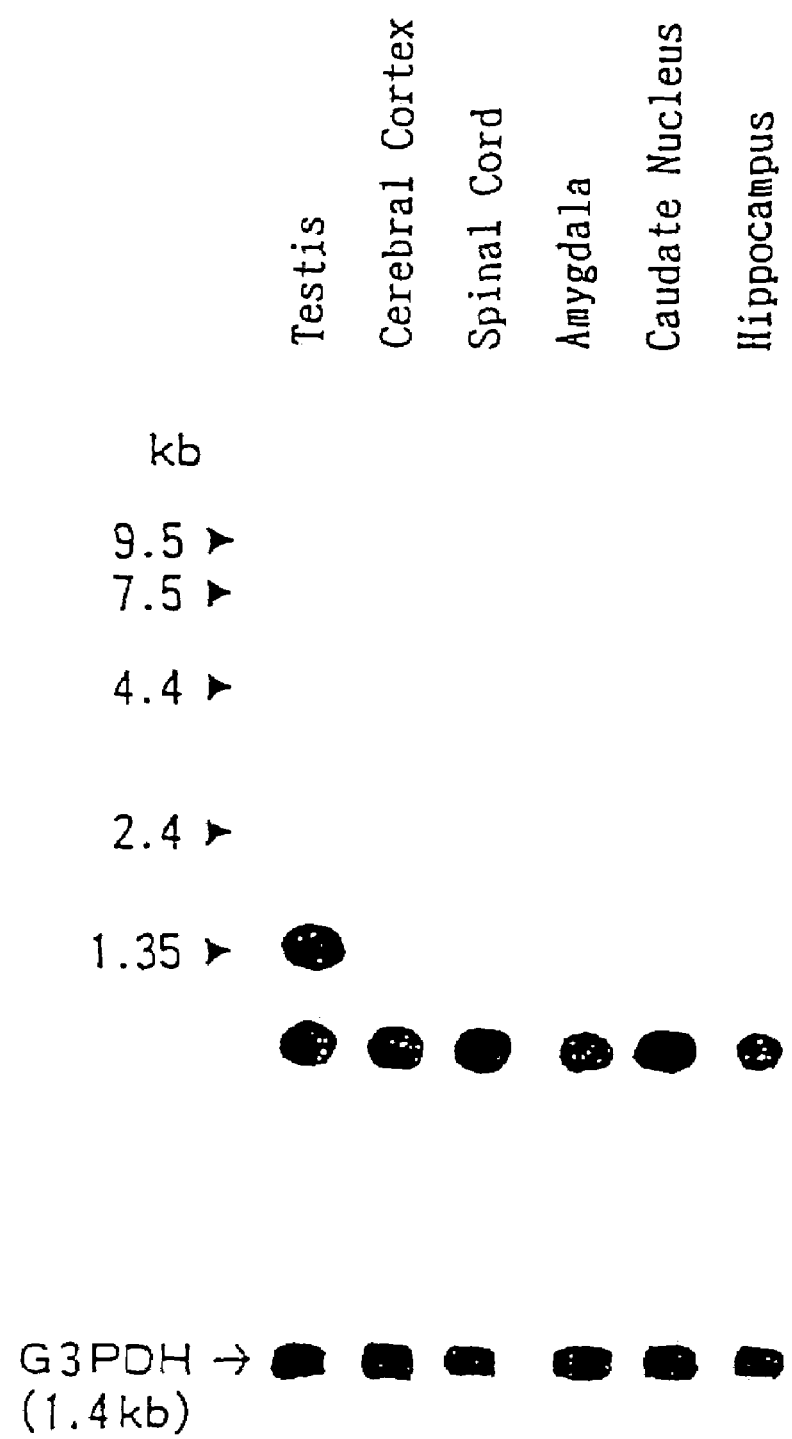
FIG. 6 shows the results of examination, by Northern hybridization, of the levels of expression of the mRNA coding for the peptide hCS-17 of the invention in various human tissues. The tissues tested were testis, cerebral cortex, spinal cord, amygdala, caudate nucleus, and hippocampus. The number (kb) on the left refers to the size of an RNA molecular weight marker.

For detecting the expression, on the mRNA level, of the novel physiologically active peptide encoded by phCSP6 in human organs, northern hybridization was carried out. The filters used for the northern blot were Human Multiple tissue Northern Blot, II, and Human Brain Multiple tissue Northern Blot II and III (CL 7760-1, CL 7759-1, CL 7755-1 and CL7750-1; Clontech). The hybridization was carried out by incubating the filters mentioned above and the probe prepared by cleaving phCSP6 with EcoRI, recovering the thus-excised fragment of about 300 bp and labeling the same by causing the same to take up [$^{32}$P]dCTP (du Pont) using a random priming DNA labeling kit (Amersham), in Express Hybri solution (Clontech) at 68° C. for 1 hour. The filters were washed with 0.1×SSC, 0.1% SDS at 50° C. and air-dried, followed by exposure thereto of X ray films (XAR5, Kodak) at −80° C. for 18 days. The results thus obtained are shown in FIG. 6. The results of northern blot obtained by using G3PDH (glyceraldehyde-3-phosphate dehydrogenase) as an internal control are also shown in FIG. 6.

From these results, it was revealed that the novel physiologically active peptide gene encoded by phCSP6 is expressed in testis, caudate nucleus, spinal cord, cerebral cortex, amygldala, hippocampus, etc.

EXAMPLE 10

Measurement of [$^{125}$I]-Somatostatin Binding Inhibition Percentages

The membrane fractions prepared in Reference Example 6 were each diluted to 3 µg/ml with assay buffer. Each dilution was distributed in 173-µl portions into tubes, and 2 µl of a solution of the test compound in dimethyl sulfoxide (DMSO) and 25 µl of 200 pM radiolabeled somatostatin ([$^{125}$I]-somatostatin; Amersham) were added simultaneously. For maximum binding measurements, reaction mixtures were prepared by adding 2 µl of DMSO and 25 µl of 200 pM [$^{125}$I]-somatostatin. Further, for non-specific binding measurements, reaction mixtures were also prepared at the same time by adding 2 µl of a 100 µM somatostatin solution in DMSO and 25 µl of 200 pM [$^{125}$I]-somatostatin. After 60 minutes of reaction at 25° C., each reaction mixture was suction-filtered using a polyethyleneimine-treated Whatman glass filter (GF-B). After filtration, the radioactivity of [$^{125}$I]-somatostatin remaining on the filter paper was measured. For each test substance, the binding inhibition percentage (%) was calculated according to the formula:

$PBM=(B-NSB)/(B_0-NSB)\times100$ (where PBM: percent maximum binding; B: radioactivity when the test sample is added; $B_0$: maximum bound radioactivity; NSB: non-specifically bound radioactivity). Further, inhibition percentages were measured varying the concentration of the test substance and the concentration of each test substance required for 50% binding inhibition ($IC_{50}$ value) was calculated by the Hill plot technique.

The $IC_{50}$ values for hCS-13, hCS-15 and hCS-17 as determined in the above manner are shown in Table 1. From Table 1, it was revealed that hCS-13, hCS-15 and hCS-17 strongly inhibit the binding of [$^{125}$I]-somatostatin against all the receptors SSTR1, SSTR2, SSTR3, SSTR4 and SSTR5.

TABLE 1

| Ligand | $IC_{50}$ (nM) | | | | |
|--------|-------|-------|-------|-------|-------|
|        | SSTR1 | SSTR2 | SSTR3 | SSTR4 | SSTR5 |
| hCS-13 | 6 | 0.3 | 0.7 | 0.5 | 0.5 |
| hCS-15 | 7 | 0.8 | 0.9 | 0.6 | 0.6 |
| hCD-17 | 7 | 0.6 | 0.6 | 0.5 | 0.4 |

EXAMPLE 11 cAMP Accumulation Inhibiting Activities of hCS15 and hCS17 in Human Somatostatin Receptor Expressing CHO Cells For measuring the intracellular accumulations of cyclic adenosine 3',5'-monophosphate (cAMP), the human somatostatin receptor expressing cell lines SSTR2-HS5-9, SSTR3-15-19, SSTR4-1-2 and SSTR5-32-4 respectively described in Reference Example 2 (3), Reference Example 3 (3), Reference Example 4 (3) and Reference Example 5 (3) were multiplied on 24-well plates until confluency. Said cells were washed with two 1-ml portions of medium A [Dulbecco-'s modified Eagle's medium (DMEM), 20 mM 2-[4-(2-hydroxyethyl)-1-piperazinyl]ethanesulfonic acid (HEPES) (pH. 7.5), 0.2% BSA, 0.2 mM 3-isobutyl-1-methylxanthine (IBMX)] and then 400 µl of medium A was added to each well and incubation was carried out at 37° C. for 1 hour. To each well were added 50 µl of a hCS-15 or hCS-17 solution (each diluted to a concentration 10 times the final concentration with medium A) and 50 µl of a forskolin solution (final concentration: 10 µM), and incubation was carried out at 37° C. for 30 minutes. The cells were washed with two 1-ml portions of medium A and then 500 µl of medium A and 100 µL of 20% aqueous perchloric acid solution were added to each well, followed by standing at 4° C. for 20 minutes for cell lysis. This lysate solution was transferred to an Eppendorf tube and centrifuged (15,000 rpm, 10 minutes), and 500 µl of the supernatant was transferred to another Eppendorf tube and neutralized with 60 mM aqueous HEPES solution containing 1.5 M potassium chloride. The amount of cAMP contained in this extract was determined using an Amersham's kit (cAMP EIA system). As a result, the intracellular cAMP accumulation upon stimulation with forskolin (10 µM) in CHO cells in which each subtype human somastatin receptor was caused to be expressed singly was found to decrease depending on the concentration of hCS-15 or hCS-177. The $ED_{50}$ values found on that occasion are shown in Table 2. It was revealed that, since, in this manner, hCS-15 and hCS-177 inhibit the adenylate cyclase activity in CHO cells expressing SSTR2, SSTR3, SSTR4 and SSTR5, they have an agonist activity against these receptors.

TABLE 2

| Peptide | $ED_{50}$ (nM) | | | |
|---------|-------|-------|-------|-------|
|         | SSTR2 | SSTR3 | SSTR4 | SSTR5 |
| hCS-15  | 7 | 1 | 0.2 | 0.2 |
| hCS-17  | 5 | 1 | 0.1 | 0.2 |

EXAMPLE 12

Effect of hCS-17 on the Rat Electroencephalogram

Using male Jcl:Wistar rats (b. wt. 300~350 g, approx.) under pentobarbital anesthesia (50 mg/kg, i.p.), the head was immobilized in a rat brain stereotaxic apparatus and the skull was drilled for placement of a screw electrode for cortical derivation and a stainless steel bipolar electrode for hippocampal derivation (A:−2.6, L:2.5, H:3.5, Pellegrino and Cushman Brain Atlas). A bipolar stainless steel needle electrode for recording an electromyogram was also inserted into the muscle layer in the dorsocervical region. All the electrodes were connected to a socket on the cranium and fixed with a dental cement. For administration of the test drug solution into the paracele, a 27-G stainless steel guide cannula was inserted in such a manner that the coordinates of its tip would be A:−0.4, L:1.7, H:1.7, and was fixed together with the EEG electrodes using a dental cement. A stilet was inserted into the guide cannula to prevent plugging of the cannula bore by tissue and blood. After postoperative recovery, the animal was submitted to the experiment. The rat was acclimatized to the experimental environment for at least 1 hour and either hCS-17 dissolved in phosphate buffered saline (PBS) or PBS was administered into the paracele via a 30-G infusion cannula. The electroencephalogram was recorded for 4 hours following administration of the test drug. The dose volume was 5 µl and the dose was 0.1 or 1 nmol. Control animals were similarly dosed with PBS. All the electrical information was recorded on a polygraph and displayed in analog and digital formats using an electroencephalogram analyzer.

The sleep-wakefulness was monitored by visual reading of the polygram and evaluated by frequency analysis and power analysis and classified into the following categories.

(1) Wakefulness:

The cortical derivation shows alpha waves (low-amplitude, fast waves) and the hippocampal derivation shows theta waves (rhythmic waves). During this time, electromyographic activity is high.

(2) SWS1 (Shallow-and-Slow Wave Sleep) and SWS2 (Deep-and-Slow Wave Sleep):

The rat assumes a sleeping posture and delta waves (spindle waves) or high-amplitude, slow-waves appear in the cerebral cortex and high-amplitude, slow-waves, appear in the hippocampal derivation. During this period, electromyographic activity is decreased (SWS1) or absent (SWS2).

(3) PS (Paradoxical Sleep):

Alpha waves (low-amplitude, fast waves) appear in the cerebral cortex and theta waves (rhythmic waves) in the hippocampal derivation. During this period, electromyographic activity is absent.

Using 5~6 rats per group, hCS-17 and PBS were respectively injected into the same rat to evaluate the relative effect on wakefulness. Analysis for statistical significance was made by paired t-test.

The typical EEG pattern immediately following injection of 1 nmol of hCS-17 is shown in FIG. 7. Immediately after administration of hCS-17, flattening of cortical and hippocampal EEG patterns occurred and persisted for 3~5 minutes. This flattening of the EEG patterns was found in 2 out of 5 animals in the 0.1 nmol group and 4 out of 6 animals in the 1 nmol group.

The percent occupancy times relative to the total EEG recording time of 4 hours are shown in FIG. 8 through FIG. 11. The hCS-17 0.1 nmol group was not different from the PBS control group in wakefulness time but showed a tendency toward decrease in SWS1 and toward increase in SWS2. PS was significantly decreased. The hCS-17 1 nmol group showed a significant decrease in SWS1, increase in SWS2, and decrease in PS.

The above results indicated that the mature peptide hCS-7 of the invention has a sleep modulating action.

INDUSTRIAL APPLICABILITY

The peptides and precursors thereof, inclusive of salts thereof, of the present invention have somatostatin-like or cortistatin-like activities, such as (i) growth hormone secretion inhibiting activity, (ii) inhibitory activity against the secretion of pituitary hormones such as thyroid stimulating hormone and prolactin, (iii) inhibitory activity against the secretion of digestive tract hormones such as gastrin and insulin, (iv) neurotransmitter activity, (v) cell proliferation activity, (vi) inhibitory activity against the activities of acetylcholine, which is a REM sleep inducer, (vii) smooth muscle contraction inhibiting activity and so on. Therefore, the peptides, precursors and salts of the invention are useful as drugs, for example as therapeutic or prophylactic agents for hormone-producing tumors, acromegaly, gigantism, dementia, diabetes, gastric ulcer and the like, hormone secretion inhibitors, tumor growth inhibitors, neural activity or sleep modulators and so forth.

The DNAs coding for the peptide or precursor of the invention are useful, for example, as agents for the gene therapy or prevention of hormone-producing tumors, acromegaly, gigantism, dementia, diabetes, gastric ulcer and the like, hormone secretion inhibitors, tumor growth inhibitors, neural activity or sleep modulators and so forth. Furthermore, the DNAs of the invention are useful as agents for the gene diagnosis of diseases such as, for example, hormone-producing tumors, acromegaly, gigantism, dementia, diabetes, gastric ulcer and the like.

The antibodies against the peptide, precursor or salt of the invention can specifically recognize the peptide, precursor or salt of the invention, hence can be used for assaying the peptide or equivalent of the invention in test solutions.

The peptides, precursors or salts of the invention are useful as reagents for screening for compounds, or salts thereof, capable of modifying the binding of the peptides, precursors or salts of the invention to the receptors.

The compounds or salts thereof as obtained by said screening are useful as drugs, for example as therapeutic or prophylactic agents for various diseases.

What is claimed is:

1. An isolated peptide comprising the amino acid sequence defined under SEQ ID NO: 1 or amino acid sequence derived therefrom by deletion, substitution or insertion of 1 to 5 amino acid residues or a salt of said peptide, wherein the peptide does not comprise the amino acid sequence of SEQ ID NO: 31 or SEQ ID NO: 32 and wherein the peptide has cortistatin or somatostatin activity.

2. A peptide as claimed in claim 1 which comprises the amino acid sequence defined under SEQ ID NO: 1 or an amino acid sequence derived therefrom by deletion or substitution of 1 to 5 amino acid residues.

3. A peptide as claimed in claim 1 which comprises the amino acid sequence defined under SEQ ID NO: 1.

4. A peptide as claimed in claim 1 which comprises the amino acid sequence defined under SEQ ID NO: 2.

5. A peptide as claimed in claim 1 which comprises the amino acid sequence defined under SEQ ID NO: 3.

6. A peptide as claimed in claim 1 which comprises the amino acid sequence defined under SEQ ID NO: 4, SEQ ID NO: 5, SEQ ID NO: 6, or SEQ ID NO: 7.

7. A pharmaceutical composition which comprises the peptide or salt claimed in claim 1.

8. A kit for screening for a compound, or a salt thereof, which is capable of modifying the binding of the peptide or salt claimed in claim 1 to a receptor for said peptide or salt, or a fragment peptide of said receptor, which kit comprises the peptide or salt claimed in claim 1.

9. An isolated peptide having the amino acid sequence defined under any of SEQ ID NO: 35 to SEQ ID NO: 38 or SEQ ID NO: 41 or a salt of said peptide, wherein the peptide has cortistatin or somatostatin activity.

10. An isolated peptide comprising the amino acid sequence defined under any one of SEQ ID NO: 1 to SEQ ID NO: 3, SEQ ID NO: 35 to SEQ ID NO: 38, SEQ ID NO: 41, SEQ ID NO: 44, SEQ ID NO: 50 and SEQ ID NO: 53 and having cortistatin or somatostatin activity.

11. An isolated peptide comprising (i) the amino acid sequence defined under any one of SEQ ID NO: 4 to SEQ ID NO: 7 or (ii) the amino acid sequence derived from the amino acid sequence defined under any one of and SEQ ID NO: 4 to SEQ ID NO: 7 by deletion of the C-terminal Lys.

* * * * *